(12) United States Patent
Adlem et al.

(10) Patent No.: US 9,914,876 B2
(45) Date of Patent: *Mar. 13, 2018

(54) BIMESOGENIC COMPOUNDS AND MESOGENIC MEDIA

(71) Applicant: Merck Patent GmbH, Darmstadt (DE)

(72) Inventors: Kevin Adlem, Bournemouth (GB); Owain Llyr Parri, Ringwood (GB); Rachel Tuffin, Chandlers Ford (GB); Patricia Eileen Saxton, Romsey (GB); Benjamin Snow, Chalfont St. Giles (GB); Mark John Goulding, Ringwood (GB); Nathan Smith, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 55 days.

This patent is subject to a terminal disclaimer.

(21) Appl. No.: 14/413,011

(22) PCT Filed: Jun. 14, 2013

(86) PCT No.: PCT/EP2013/001771
§ 371 (c)(1),
(2) Date: Jan. 6, 2015

(87) PCT Pub. No.: WO2014/005670
PCT Pub. Date: Jan. 9, 2014

(65) Prior Publication Data
US 2015/0203755 A1    Jul. 23, 2015

(30) Foreign Application Priority Data

Jul. 6, 2012 (EP) .................................. 12005047

(51) Int. Cl.
| | | |
|---|---|---|
| *G02F 1/1333* | (2006.01) | |
| *C09K 19/20* | (2006.01) | |
| *C09K 19/02* | (2006.01) | |
| *C09K 19/04* | (2006.01) | |
| *C07C 25/18* | (2006.01) | |
| *C07C 43/225* | (2006.01) | |
| *C07C 69/67* | (2006.01) | |
| *C07C 255/50* | (2006.01) | |

(52) U.S. Cl.
CPC .......... *C09K 19/2014* (2013.01); *C07C 25/18* (2013.01); *C07C 43/225* (2013.01); *C07C 69/67* (2013.01); *C07C 255/50* (2013.01); *C09K 19/0258* (2013.01); *C09K 19/04* (2013.01); *C09K 2019/0444* (2013.01)

(58) Field of Classification Search
CPC   C09K 19/2014; C09K 19/0258; C09K 19/04; C09K 2019/0444; G02F 1/1333; C07C 25/18; C07C 43/225; C07C 69/67; C07C 255/50

USPC ............. 252/299.01, 299.6, 299.63, 299.65; 428/1.1
See application file for complete search history.

(56) References Cited

U.S. PATENT DOCUMENTS

| | | | |
|---|---|---|---|
| 5,209,868 A | 5/1993 | Reiffenrath | |
| 6,210,603 B1 | 4/2001 | Kondo | |
| 7,623,214 B2 | 11/2009 | Coles et al. | |
| 8,377,519 B2 | 2/2013 | Farrand et al. | |
| 2010/0296038 A1 | 11/2010 | Farrand et al. | |
| 2014/0232977 A1 | 8/2014 | Adlem et al. | |
| 2015/0090935 A1* | 4/2015 | Adlem ................ | C09K 19/0258 252/299.6 |
| 2015/0175883 A1 | 6/2015 | Adlem et al. | |
| 2015/0175886 A1* | 6/2015 | Tuffin ................ | G02F 1/134309 349/139 |
| 2015/0203756 A1 | 7/2015 | Adlem et al. | |
| 2015/0210921 A1* | 7/2015 | Adlem ................ | C09K 19/0258 252/299.65 |
| 2015/0315470 A1* | 11/2015 | Adlem ................ | C09K 19/0258 252/299.65 |

FOREIGN PATENT DOCUMENTS

| | | |
|---|---|---|
| CN | 1934222 B | 9/2011 |
| CN | 103619992 A | 3/2014 |
| EP | 1477547 A | 11/2004 |
| EP | 1477547 A1 | 11/2004 |

(Continued)

OTHER PUBLICATIONS

International Search Report from PCT Application No. PCT/EP2013/001771 dated Sep. 9, 2013.
Office Action related to the corresponding Chinese Patent Application No. 201380035216.5 dated Dec. 1, 2015.
English language trnalsation of Office Action and Search Report corresponding to Taiwanese Patent Application No. 102124300, dated Nov. 14, 2016.
Office Action in corresponding JP Appln. No. 2015-518883 dated Mar. 8, 2017.
Yoshizawa et al., Chem. Mater. 2005, vol. 17, p. 6442-6446.
Araya et al., Journal of Materials Chemistry, 2006, vol. 16, p. 4675-4689.
Byung-Wook Jo., Bull. Korean Chem. Soc., 1990, vol. 11, p. 333-339.

(Continued)

*Primary Examiner* — Geraldina Visconti
(74) *Attorney, Agent, or Firm* — Millen White Zelano & Branigan, PC

(57) ABSTRACT

The invention relates to bimesogenic compounds of formula I

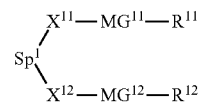

wherein $R^{11}$, $R^{12}$, $MG^{11}$, $MG^{12}$, $X^{11}$, $X^{12}$ and $Sp^1$ have the meaning given in claim 1, to the use of bimesogenic compounds of formula I in liquid crystal media and particular to flexoelectric liquid crystal devices comprising a liquid crystal medium according to the present invention.

22 Claims, No Drawings

(56) References Cited

FOREIGN PATENT DOCUMENTS

| GB | 2356629 A | 5/2001 |
|---|---|---|
| JP | H05-500204 A | 1/1993 |
| JP | H08-183749 A | 7/1996 |
| JP | H08-198785 A | 8/1996 |
| JP | H09-87210 A | 3/1997 |
| TW | 201402790 A | 1/2014 |
| TW | 201406933 A | 2/2014 |
| WO | 98/23564 A1 | 6/1998 |
| WO | 2013004333 A1 | 1/2013 |

OTHER PUBLICATIONS

Chapman et al., Mol. Cryst. Liq. Cryst., 2004, vol. 411, p. 49-56.
Kelly, Liquid Crystals, 1991, vol. 10, p. 273-287.
Yoshizawa et al., Liquid Crystals, 2007, vol. 34, p. 373-379.
English abstract translation of JP8198785A issued to Dainippon Ink & Chemicals on Aug. 6, 1996.
English abstract translation of JP8183749A issued to Dainippon Ink & Chemicals on Jul. 16, 1996.
English abstract translation of JP9087210A issued Mar. 31, 1997 to Fujimoto Yukari Sumitomo Chemical Co entitled Aromatic Compound.

* cited by examiner

BIMESOGENIC COMPOUNDS AND MESOGENIC MEDIA

The invention relates to bimesogenic compounds of formula I

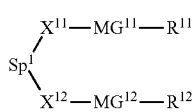

wherein $R^{11}$, $R^{12}$, $MG^{11}$, $MG^{12}$ and $Sp^1$ have the meaning given herein below, to the use of bimesogenic compounds of formula I in liquid crystal media and particular to flexoelectric liquid crystal devices comprising a liquid crystal medium according to the present invention.

Liquid Crystal Displays (LCDs) are widely used to display information. LCDs are used for direct view displays, as well as for projection type displays. The electro-optical mode which is employed for most displays still is the twisted nematic (TN)-mode with its various modifications. Besides this mode, the super twisted nematic (STN)-mode and more recently the optically compensated bend (OCB)-mode and the electrically controlled birefringence (ECB)-mode with their various modifications, as e.g. the vertically aligned nematic (VAN), the patterned ITO vertically aligned nematic (PVA)-, the polymer stabilized vertically aligned nematic (PSVA)-mode and the multi domain vertically aligned nematic (MVA)-mode, as well as others, have been increasingly used. All these modes use an electrical field, which is substantially perpendicular to the substrates, respectively to the liquid crystal layer. Besides these modes there are also electro-optical modes employing an electrical field substantially parallel to the substrates, respectively the liquid crystal layer, like e.g. the In Plane Switching (short IPS) mode (as disclosed e.g. in DE 40 00 451 and EP 0 588 568) and the Fringe Field Switching (FFS) mode. Especially the latter mentioned electro-optical modes, which have good viewing angle properties and improved response times, are increasingly used for LCDs for modern desktop monitors and even for displays for TV and for multimedia applications and thus are competing with the TN-LCDs.

Further to these displays, new display modes using cholesteric liquid crystals having a relatively short cholesteric pitch have been proposed for use in displays exploiting the so called "flexo-electric" effect. The term "liquid crystal", "mesomorphic compound" or "mesogenic compound" (also shortly referred to as "mesogen") means a compound that under suitable conditions of temperature, pressure and concentration can exist as a mesophase (nematic, smectic, etc.) or in particular as a LC phase. Non-amphiphilic mesogenic compounds comprise for example one or more calamitic, banana-shaped or discotic mesogenic groups.

Flexoelectric liquid crystal materials are known in prior art. The flexoelectric effect is described inter alia by Chandrasekhar, "Liquid Crystals", 2nd edition, Cambridge University Press (1992) and P. G. deGennes et al., "The Physics of Liquid Crystals", 2nd edition, Oxford Science Publications (1995).

In these displays the cholesteric liquid crystals are oriented in the "uniformly lying helix" arrangement (ULH), which also give this display mode its name. For this purpose, a chiral substance which is mixed with a nematic material induces a helical twist transforming the material into a chiral nematic material, which is equivalent to a cholesteric material. The term "chiral" in general is used to describe an object that is non-superimposable on its mirror image. "Achiral" (non-chiral) objects are objects that are identical to their mirror image. The terms chiral nematic and cholesteric are used synonymously in this application, unless explicitly stated otherwise. The pitch induced by the chiral substance ($P_0$) is in a first approximation inversely proportional to the concentration (c) of the chiral material used. The constant of proportionality of this relation is called the helical twisting power (HTP) of the chiral substance and defined by equation (1)

$$HTP \equiv 1/(c \cdot P_0) \quad (1)$$

wherein
c is concentration of the chiral compound.

The uniform lying helix texture is realized using a chiral nematic liquid crystal with a short pitch, typically in the range from 0.2 μm to 1 μm, preferably of 1.0 μm or less, in particular of 0.5 μm or less, which is unidirectional aligned with its helical axis parallel to the substrates, e.g. glass plates, of a liquid crystal cell. In this configuration the helical axis of the chiral nematic liquid crystal is equivalent to the optical axis of a birefringent plate.

If an electrical field is applied to this configuration normal to the helical axis the optical axis is rotated in the plane of the cell, similar as the director of a ferroelectric liquid crystal rotate as in a surface stabilized ferroelectric liquid crystal display. The flexoelectric effect is characterized by fast response times typically ranging from 6 μs to 100 μs. It further features excellent grey scale capability.

The field induces a splay bend structure in the director which is accommodated by a tilt in the optical axis. The angle of the rotation of the axis is in first approximation directly and linearly proportional to the strength of the electrical field. The optical effect is best seen when the liquid crystal cell is placed between crossed polarizers with the optical axis in the unpowered state at an angle of 22.5° to the absorption axis of one of the polarizers. This angle of 22.5° is also the ideal angle of rotation of the electric field, as thus, by the inversion the electrical field, the optical axis is rotated by 45° and by appropriate selection of the relative orientations of the preferred direction of the axis of the helix, the absorption axis of the polarizer and the direction of the electric field, the optical axis can be switched from parallel to one polarizer to the center angle between both polarizers. The optimum contrast is then achieved when the total angle of the switching of the optical axis is 45°. In that case the arrangement can be used as a switchable quarter wave plate, provided the optical retardation, i.e. the product of the effective birefringence of the liquid crystal and the cell gap, is selected to be the quarter of the wave length. In this context the wavelength referred to is 550 nm, the wavelength for which the sensitivity of the human eye is highest, unless explicitly stated otherwise.

The angle of rotation of the optical axis ($\Phi$) is given in good approximation by formula (2)

$$\tan \Phi = \overline{e} P_0 E / (2\pi K) \quad (2)$$

wherein
$P_0$ is the undisturbed pitch of the cholesteric liquid crystal,
$\overline{e}$ is the average [$\overline{e} = \frac{1}{2} (e_{splay} + e_{bend})$] of the splay flexoelectric coefficient ($e_{splay}$) and the bend flexoelectric coefficient ($e_{bend}$),
E is the electrical field strength and
K is the average [$K = \frac{1}{2} (k_{11} + k_{33})$] of the splay elastic constant ($k_{11}$) and the bend elastic constant ($K_{33}$)
and wherein
$\overline{e}/K$ is called the flexo-elastic ratio.

This angle of rotation is half the switching angle in a flexoelectric switching element.

The response time (τ) of this electro-optical effect is given in good approximation by formula (3)

$$\tau = [P_0/(2\pi)]^2 \cdot \gamma/K \quad (3)$$

wherein
γ is the effective viscosity coefficient associated with the distortion of the helix.

There is a critical field ($E_c$) to unwind the helix, which can be obtained from equation (4)

$$E_c = (\pi^2/P_0) \cdot [k_{22}/(\epsilon_0 \cdot \Delta\epsilon)]^{1/2} \quad (4)$$

wherein
$k_{22}$ is the twist elastic constant,
$\epsilon_0$ is the permittivity of vacuum and
Δ∈ is the dielectric anisotropy of the liquid crystal.

In this mode, however several problems still have to be resolved, which are, amongst others, difficulties in obtaining the required uniform orientation, an unfavorably high voltage required for addressing, which is incompatible with common driving electronics, a not really dark "off state", which deteriorates the contrast, and, last not least, a pronounced hysteresis in the electro-optical characteristics.

A relatively new display mode, the so-called uniformly standing helix (USH) mode, may be considered as an alternative mode to succeed the IPS, as it can show improved black levels, even compared to other display mode providing wide viewing angles (e.g. IPS, VA etc.).

For the USH mode, like for the ULH mode, flexoelectric switching has been proposed, using bimesogenic liquid crystal materials. Bimesogenic compounds are known in general from prior art (cf. also Hori, K., Iimuro, M., Nakao, A., Toriumi, H., J. Mol. Struc. 2004, 699, 23-29). The term "bimesogenic compound" relates to compounds comprising two mesogenic groups in the molecule. Just like normal mesogens they can form many mesophases, depending on their structure. In particular compounds of formula I induce a second nematic phase, when added to a nematic liquid crystal medium.

The term "mesogenic group" means in this context, a group with the ability to induce liquid crystal (LC) phase behaviour. The compounds comprising mesogenic groups do not necessarily have to exhibit an LC phase themselves. It is also possible that they show LC phase behaviour only in mixtures with other compounds. For the sake of simplicity, the term "liquid crystal" is used hereinafter for both mesogenic and LC materials.

However, due to the unfavorably high driving voltage required, to the relatively narrow phase range of the chiral nematic materials and to their irreversible switching properties, materials from prior art are not compatible for the use with current LCD driving schemes.

For displays of the USH and ULH mode, new liquid crystalline media with improved properties are required. Especially the birefringence (Δn) should be optimized for the optical mode. The birefringence Δn herein is defined in equation (5)

$$\Delta n = n_e - n_0 \quad (5)$$

wherein $n_e$ is the extraordinary refractive index and $n_o$ is the ordinary refractive index, and the average refractive index $n_{av.}$ is given by the following equation (6).

$$n_{av.} = [(2n_o^2 + n_e^2)/3]^{1/2} \quad (6)$$

The extraordinary refractive index $n_e$ and the ordinary refractive index $n_o$ can be measured using an Abbe refractometer. Δn can then be calculated from equation (5).

Furthermore, for displays utilizing the USH or ULH mode the optical retardation d*Δn (effective) of the liquid crystal media should preferably be such that the equation (7)

$$\sin 2(\pi \cdot d \cdot \Delta n/\lambda) = 1 \quad (7)$$

wherein
d is the cell gap and
λ is the wave length of light
is satisfied. The allowance of deviation for the right hand side of equation (7) is +/−3%.

The wave length of light generally referred to in this application is 550 nm, unless explicitly specified otherwise.

The cell gap of the cells preferably is in the range from 1 μm to 20 μm, in particular within the range from 2.0 μm to 10 μm.

For the ULH/USH mode, the dielectric anisotropy (Δ∈) should be as small as possible, to prevent unwinding of the helix upon application of the addressing voltage. Preferably Δ∈ should be slightly higher than 0 and very preferably be 0.1 or more, but preferably 10 or less, more preferably 7 or less and most preferably 5 or less. In the present application the term "dielectrically positive" is used for compounds or components with Δ∈>3.0, "dielectrically neutral" with −1.5≤Δ∈≤3.0 and "dielectrically negative" with Δ∈<−1.5. Δ∈ is determined at a frequency of 1 kHz and at 20° C. The dielectric anisotropy of the respective compound is determined from the results of a solution of 10% of the respective individual compound in a nematic host mixture. In case the solubility of the respective compound in the host medium is less than 10% its concentration is reduced by a factor of 2 until the resultant medium is stable enough at least to allow the determination of its properties. Preferably the concentration is kept at least at 5%, however, in order to keep the significance of the results a high as possible. The capacitance of the test mixtures are determined both in a cell with homeotropic and with homogeneous alignment. The cell gap of both types of cells is approximately 20 μm. The voltage applied is a rectangular wave with a frequency of 1 kHz and a root mean square value typically of 0.5 V to 1.0 V, however, it is always selected to be below the capacitive threshold of the respective test mixture.

Δ∈ is defined as ($\epsilon_\parallel - \epsilon_\perp$), whereas $E_{av.}$ is ($\epsilon_\parallel + 2\epsilon_\perp$)/3. The dielectric permittivity of the compounds is determined from the change of the respective values of a host medium upon addition of the compounds of interest. The values are extrapolated to a concentration of the compounds of interest of 100%. A typical host mixture is disclosed in H. J. Coles et al., J. Appl. Phys. 2006, 99, 034104 and has the composition given in the following table.

| Compound | Concentration |
| --- | --- |
| F-PGI-ZI-9-ZGP-F | 25% |
| F-PGI-ZI-11-ZGP-F | 25% |
| FPGI-O-5-O-PP-N | 9.5% |
| FPGI-O-7-O-PP-N | 39% |
| CD-1 | 1.5% |

Besides the above mentioned parameters, the media have to exhibit a suitably wide range of the nematic phase, a rather small rotational viscosity and an at least moderately high specific resistivity.

Similar liquid crystal compositions with short cholesteric pitch for flexoelectric devices are known from EP 0 971 016, GB 2 356 629 and Coles, H. J., Musgrave, B., Coles, M. J., and Willmott, J., J. Mater. Chem., 11, p. 2709-2716 (2001). EP 0 971 016 reports on mesogenic estradiols, which, as such, have a high flexoelectric coefficient. GB 2 356 629 suggests the use of bimesogenic compounds in flexoelectric devices. The flexoelectric effect herein has been investigated in pure cholesteric liquid crystal compounds and in mixtures of homologous compounds only so far. Most of these compounds were used in binary mixtures consisting of a chiral additive and a nematic liquid crystal material being either a simple, conventional monomesogenic material or a bimesogenic one. These materials do have several drawbacks for practical applications, like insufficiently wide temperature ranges of the chiral nematic—or cholesteric phase, too small flexoelectric ratios, small angles of rotation.

Bimesogenic compounds bearing one or two $OCF_3$— groups, corresponding to TO-GIP-O-n-O—PP—N and TO-GIP-O-n-O-PG-OT according to the abbreviations used in the instant application, are mentioned in general formulae in EP 1 477 547 A1.

One aim of the invention was to provide improved flexoelectric devices that exhibit high switching angles and fast response times. Another aim was to provide liquid crystal materials with advantageous properties, in particular for use in flexoelectric displays that enable good uniform alignment over the entire area of the display cell without the use of a mechanical shearing process, good contrast, high switching angles and fast response times also at low temperatures. The liquid crystal materials should exhibit low melting points, broad chiral nematic phase ranges, short temperature independent pitch lengths and high flexoelectric coefficients. Other aims of the present invention are immediately evident to the person skilled in the art from the following detailed description.

The inventors have found out that the above aims can be surprisingly achieved by providing bimesogenic compounds according to the present invention. These compounds, when used in chiral nematic liquid crystal mixtures, lead to low melting points, broad chiral nematic phases. In particular, they exhibit relatively high values of the elastic constant $k_{11}$, low values of the bend elastic constant $k_{33}$ and the flexoelectric coefficient.

Thus, the present invention relates to bimesogenic compounds of formula I

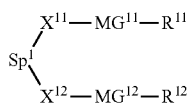
                                                       I wherein
$R^{11}$ is $OCF_3$ or $CF_3$,
$R^{12}$ is $OCF_3$, $CF_3$, H, F, Cl, CN, NCS or a straight-chain or branched alkyl group with 2 to 25 C atoms which may be unsubstituted, mono- or polysubstituted by halogen or CN, it being also possible for one or more non-adjacent $CH_2$ groups to be replaced, in each occurrence independently from one another, by —O—, —S—, —NH—, —N(CH$_3$)—, —CO—, —COO—, —OCO—, —O—CO—O—, —S—CO—, —CO—S—, —CH═CH—, —CH═CF—, —CF═CF— or —C≡C— in such a manner that oxygen atoms are not linked directly to one another, preferably a polar group, more preferably F, Cl, CN, $OCF_3$ or $CF_3$,
$MG^{11}$ and $MG^{12}$ are each independently a mesogenic group, at least one of
$MG^{11}$ and $MG^{12}$ comprises one, two or more 6-atomic rings, in case of comprising two or more 6-atomic rings at least two of these may be linked by a 2-atomic linking group, preferably selected from the group of linking groups —CO—O—, —O—CO—, —CH$_2$—O—, —O—CH$_2$—, —CF$_2$—O— and —O—CF$_2$—
$Sp^1$ is a spacer group comprising 1, 3 or 5 to 40 C atoms, wherein one or more non-adjacent and non-terminal $CH_2$ groups may also be replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH═CH— or —C≡C—, however in such a way that no two O-atoms are adjacent to one another, now two —CH═CH— groups are adjacent to each other and no two groups selected from —O—CO—, —S—CO—, —O—COO—, —CO—S—, —CO—O— and —CH═CH— are adjacent to each other, preferably —(CH$_2$)$_n$— (i.e. 1,n-alkylene with n C atoms), with n an integer, preferably from 3 to 19, more preferably from 3 to 11, most preferably an odd integer (i.e. 3, 5, 7, 9 or 11),
$X^{11}$ and $X^{12}$ are independently from one another a linking group selected from —CO—O—, —O—CO—, —CH═CH—, —C≡C—, —S—, —O— and a single bond, preferably —CO—O—, —O—CO— or a single bond, most preferably a single bond,
however under the conditions
that in —$X^{11}$-$Sp^1$-$X^{12}$— no two O-atoms are adjacent to one another, now two —CH═CH— groups are adjacent to each other and no two groups selected from —O—CO—, —S—CO—, —O—CO—, —CO—S—, —CO—O— and —CH═CH— are adjacent to each other and
that preferably compounds of the formulae
TO-GIP-O-n-O—PP—N and TO-GIP-O-n-O-PG-OT are excluded from formula I.
Preferably
—$X^{11}$-$Sp^1$-$X^{12}$— is —O—CO-$Sp^1$-O—CO—, —C≡C-$Sp^1$-C≡C— or -$Sp^1$- and
$Sp^1$ is —(CH$_2$)$_n$— with
n 1, 3 or an integer from 5 to 15, most preferably an odd (i.e. uneven) integer and,
wherein one or more H atoms in —(CH$_2$)$_n$— may independently of each other optionally be replaced by F or CH$_3$.

Preferred compounds of formula I are compounds in which
$MG^{11}$ and $MG^{12}$ are independently from one another a group of (partial) formula II

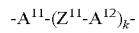
                                                     II wherein
$Z^{11}$ are, independently of each other in each occurrence, a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH═CH—, —CF═CF—, —CH═CH—COO—, —OCO—CH═CH— or —C≡C—, optionally substituted with one or more of F, S and/or Si, preferably a single bond,
$A^{11}$ and $A^{12}$ are each independently in each occurrence 1,4-phenylene, wherein in addition one or more CH groups may be replaced by N, trans-1,4-cyclo-hexylene in which, in addition, one or two non-adjacent CH$_2$ groups may be replaced by O and/or S, 1,4-cyclohexenylene, 1,4-bicyclo-(2,2,2)-octylene, piperidine-1,4-diyl, naphthalene-2,6-diyl, decahydro-naphthalene-2,6-diyl, 1,2,3,4-tetrahydro-naphthalene-2,6-diyl, cyclobutane-1,3-diyl, spiro[3.3]heptane-2,6-diyl or dispiro[3.1.3.1]decane-2,8- diyl, it being possible for all these groups to be unsubstituted, mono-, di-, tri- or tetrasubstituted with F, Cl, CN or alkyl, alkoxy, alkylcarbonyl or one or more H atoms may be substituted by F or Cl, preferably F, Cl, $CH_3$ or $CF_3$, and k is 0, 1, 2, 3 or 4, preferably 1, 2 or 3 and, most preferably 1 or 2.

Especially preferred are compounds of formula I wherein the mesogenic groups $MG^{11}$ and $MG^{12}$ at each occurrence independently from each other comprise one, two or three six-membered rings, preferably two or three six-membered rings.

A smaller group of preferred mesogenic groups of formula II is listed below. For reasons of simplicity, Phe in these groups is 1,4-phenylene, PheL is a 1,4-phenylene group which is substituted by 1 to 4 groups L, with L being preferably F, Cl, CN, OH, $NO_2$ or an optionally fluorinated alkyl, alkoxy or alkanoyl group with 1 to 7 C atoms, very preferably F, Cl, CN, OH, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$, $OC_2F_5$, in particular F, Cl, CN, $CH_3$, $C_2H_5$, $OCH_3$, $COCH_3$ and $OCF_3$, most preferably F, Cl, $CH_3$, $OCH_3$ and $COCH_3$ and Cyc is 1,4-cyclohexylene. This list comprises the subformulae shown below as well as their mirror images

| | |
|---|---|
| -Phe-Z-Phe- | II-1 |
| -Phe-Z-Cyc- | II-2 |
| -Cyc-Z-Cyc- | II-3 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| -Cyc-Z-Phe-Z-Cyc- | II-11 |
| -Phe-Z-Cyc-Z-Cyc- | II-12 |
| -Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-29 |
| -Phe-Z-Cyc-Z-PheL- | II-21 |
| -Cyc-Z-Phe-Z-PheL- | II-22 |
| -PheL-Z-Cyc-Z-PheL- | II-23 |
| -PheL-Z-PheL-Z-Cyc- | II-24 |
| -PheL-Z-Cyc-Z-Cyc- | II-25 |
| -Cyc-Z-PheL-Z-Cyc- | II-26 | wherein

Cyc is 1,4-cyclohexlene, preferably trans-1,4-cyclohexlene,

Phe is 1,4-phenylene,

PheL is 1,4-phenylene, which is substituted by one, two or three fluorine atoms, by one or two Cl atoms or by one Cl atom and one F atom, and Z has one of the meanings of $Z^{11}$ as given under partial formula II, at least one is preferably selected from —COO—, —OCO—, —O—CO—O—, —$OCH_2$—, —$CH_2O$—, —$OCF_2$— or —$CF_2O$—.

Particularly preferred are the sub-formulae II-1, II-4, II-5, II-7, II-8, II-14, II-15, II-16, II-17, II-18 and II-19.

In these preferred groups Z in each case independently has one of the meanings of $Z^{11}$ as given under formula I. Preferably one of Z is —COO—, —OCO—, —$CH_2$—O—, —O—$CH_2$—, —$CF_2$—O— or —O—$CF_2$—, more preferably —COO—, —O—$CH_2$— or —$CF_2$—O—, and the others preferably are a single bond.

Very preferably at least one of the mesogenic groups $MG^{11}$ and $MG^{12}$ is, and preferably both of them are each and independently, selected from the following formulae IIa to IIn (the two reference Nos. "II i" and "II l" being deliberately omitted to avoid any confusion) and their mirror images

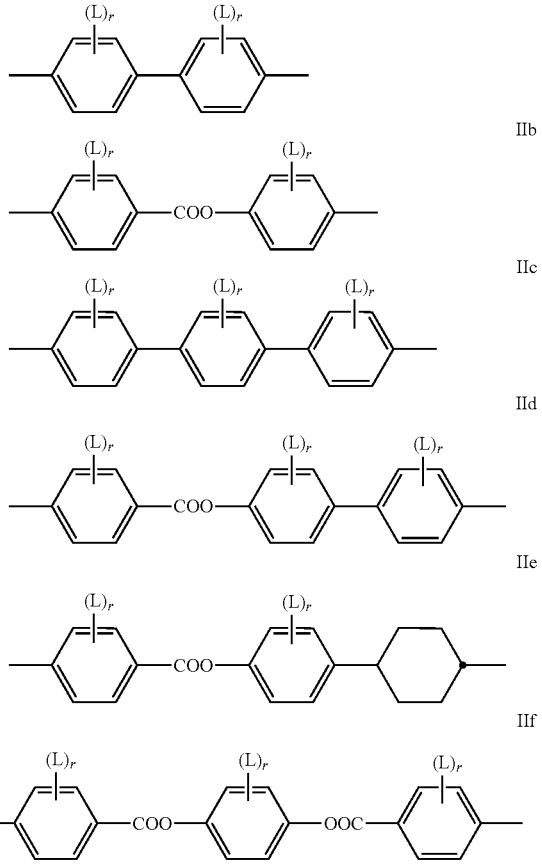

-continued

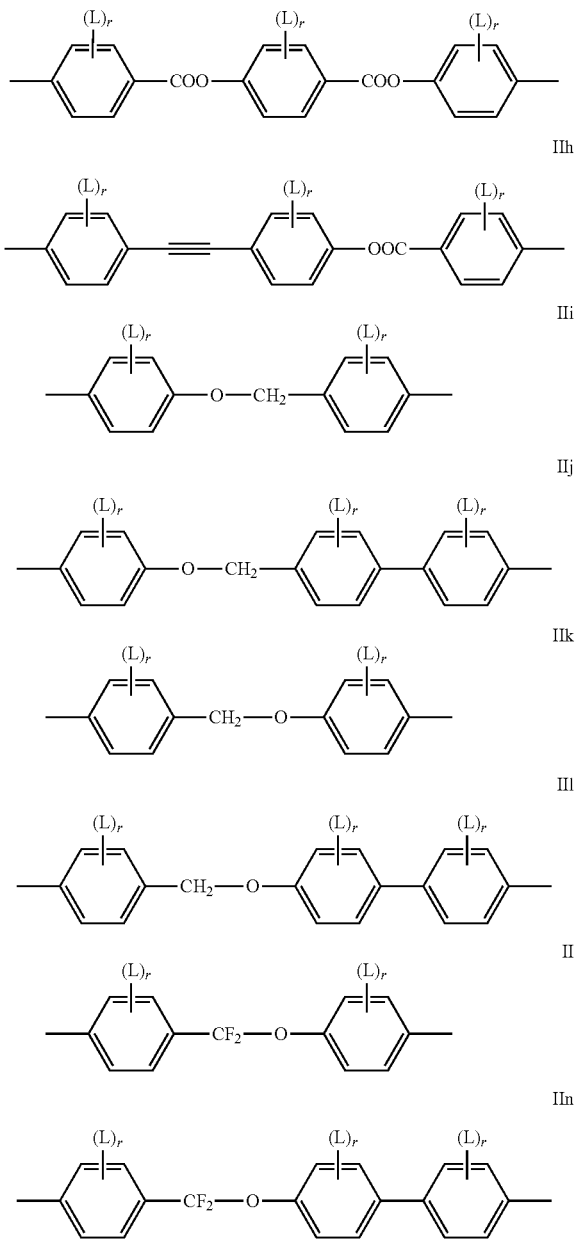

wherein

L is in each occurrence independently of each other F or Cl, preferably F and r is in each occurrence independently of each other 0, 1, 2 or 3, preferably 0, 1 or 2.

The group

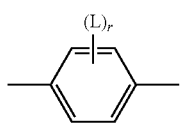

in these preferred formulae is very preferably denoting

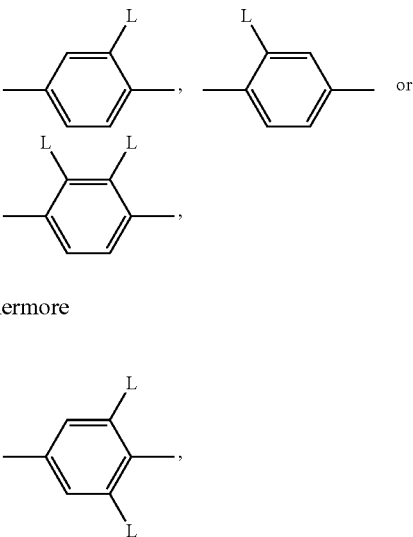

furthermore

L is in each occurrence independently of each other F or Cl, F.

In case of compounds with a unpolar group, $R^{11}$ and $R^{12}$ are preferably alkyl with up to 15 C atoms or alkoxy with 2 to 15 C atoms.

If $R^{11}$ or $R^{12}$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In case of a compounds with a terminal polar group, $R^{11}$ and $R^{12}$ are selected from CN, $NO_2$, halogen, $OCH_3$, OCN, SCN, $COR^x$, $COOR^x$ or a mono-oligo- or polyfluorinated alkyl or alkoxy group with 1 to 4 C atoms. $R^x$ is optionally fluorinated alkyl with 1 to 4, preferably 1 to 3 C atoms. Halogen is preferably F or Cl.

Especially preferably $R^{11}$ and $R^{12}$ in formula I are selected of H, F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of H, F, Cl, CN, $OCH_3$ and $OCF_3$, especially of H, F, CN and $OCF_3$.

In addition, compounds of formula I containing an achiral branched group $R^{11}$ and/or $R^{12}$ may occasionally be of importance, for example, due to a reduction in the tendency towards crystallisation. Branched groups of this type generally do not contain more than one chain branch. Preferred achiral branched groups are isopropyl, isobutyl (32 methylpropyl), isopentyl (=3-methylbutyl), isopropoxy, 2-methylpropoxy and 3-methylbutoxy.

The spacer group $Sp^1$ is preferably a linear or branched alkylene group having 1, 3 or 5 to 40 C atoms, in particular 1, 3 or 5 to 25 C atoms, very preferably 1, 3 or 5 to 15 C atoms, and most preferably 5 to 15 C atoms, in which, in addition, one or more non-adjacent and non-terminal $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

"Terminal" $CH_2$ groups are those directly bonded to the mesogenic groups. Accordingly, "non-terminal" $CH_2$ groups are not directly bonded to the mesogenic groups $MG^{11}$ and $MG^{12}$.

Typical spacer groups are for example —$(CH_2)_o$—, —$(CH_2CH_2O)_p$—$CH_2CH_2$—, with o being an integer from 5 to 40, in particular from 5 to 25, very preferably from 5 to 15, and p being an integer from 1 to 8, in particular 1, 2, 3 or 4.

Preferred spacer groups are pentylene, hexylene, heptylene, octylene, nonylene, decylene, undecylene, dodecylene, octadecylene, diethyleneoxyethylene, dimethyleneoxybutylene, pentenylene, heptenylene, nonenylene and undecenylene, for example.

Especially preferred are inventive compounds of formula I wherein Sp is denoting alkylene with 5 to 15 C atoms. Straight-chain alkylene groups are especially preferred.

Preferred are spacer groups with even numbers of a straight-chain alkylene having 6, 8, 10, 12 and 14 C atoms.

In another embodiment of the present invention are the spacer groups preferably with odd numbers of a straight-chain alkylene having 5, 7, 9, 11, 13 or 15 C atoms. Very preferred are straight-chain alkylene spacers having 7, 9, and 11 C atoms.

Especially preferred are inventive compounds of formula I wherein Sp is denoting complete deuterated alkylene with 5 to 15 C atoms. Very preferred are deuterated straight-chain alkylene groups. Most preferred are partially deuterated straight-chain alkylene groups.

Preferred are compounds of formula I wherein the mesogenic groups $R^{11}$-$MG^{11}$-$X^{11}$— and $R^{12}$-$MG^{12}$-$X^{12}$— are different from each other. In another embodiment compounds of formula I wherein $R^{11}$-$MG^{11}$-$X^{11}$— and $R^{12}$-$MG^{12}$-$X^{12}$— in formula I are identical to each other.

Preferred compounds of formula I are selected from the group of compounds of formulae IA to IK, preferably of formula ID

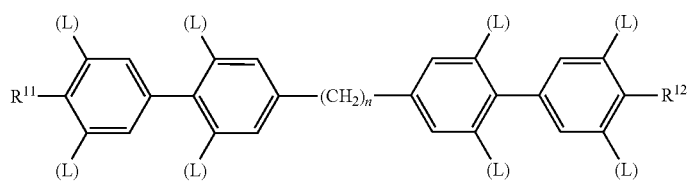

IA

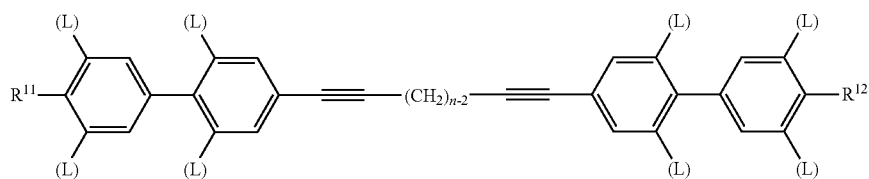

IB

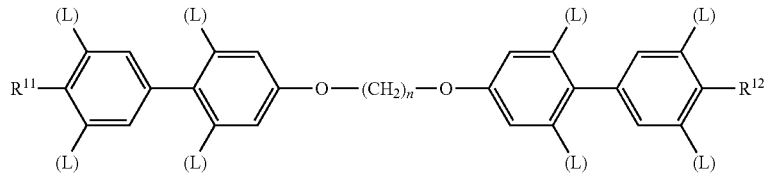

IC

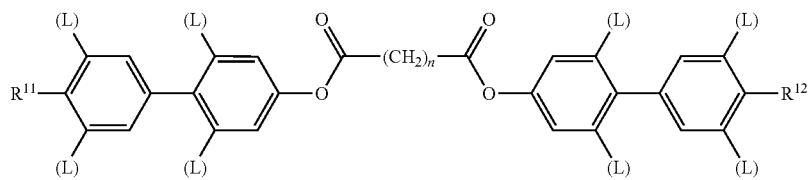

ID

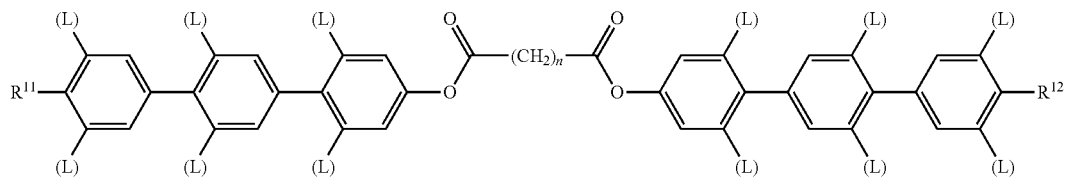

IE

-continued

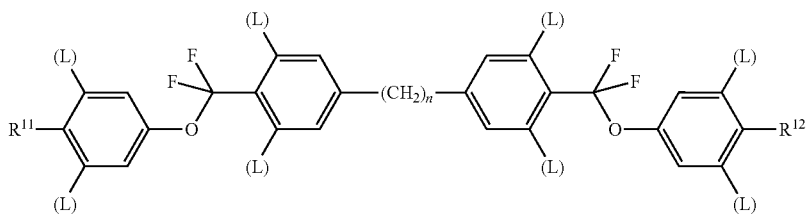

IF

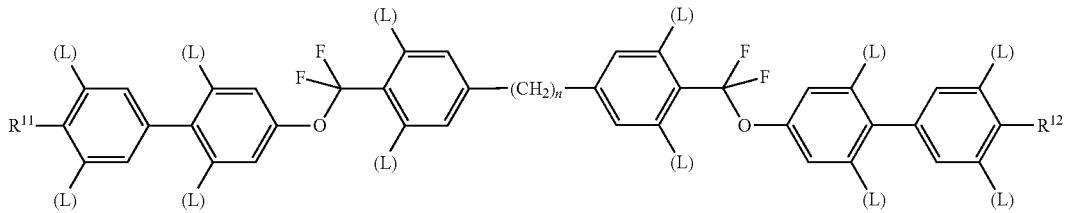

IG

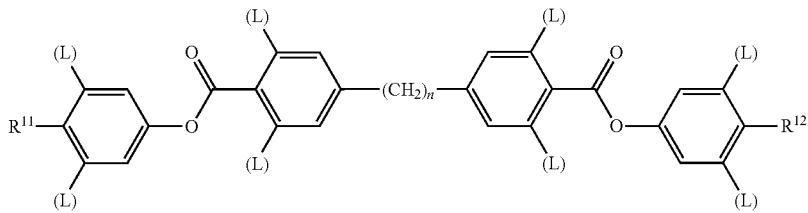

IH

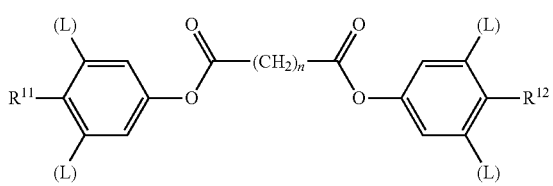

IJ

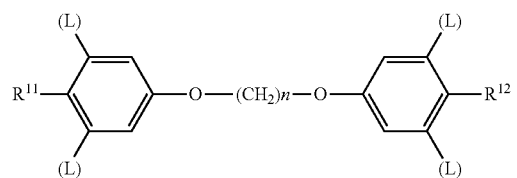

IK wherein $R^{11}$ and $R^{12}$ are independently from each other as defined above, including the preferred meanings of these groups, preferably $R^{11}$ is $OCF_3$, preferably $R^{12}$ is $OCF_3$, $CF_3$, F or CN, preferably $OCF_3$ or CN and most preferably CN and wherein L is in each occurrence independently of each other F, Cl or preferably F or Cl, most preferably F.

Particularly preferred compounds are selected from the group of formulae given above, which bear 0, 2 or 4 F atoms in lateral positions (i.e. as L).

In a preferred embodiment of the present invention $R^{11}$ is $OCF_3$ and $R^{12}$ is $OCF_3$, F or CN, preferably $OCF_3$ or CN and most preferably CN.

The compounds of formula I can be synthesized according to or in analogy to methods which are known per se and which are described in standard works of organic chemistry such as, for example, Houben-Weyl, Methoden der organischen Chemie, Thieme-Verlag, Stuttgart. A preferred method of preparation can be taken from the following synthesis schemes.

The compounds of formula I are preferably accessible according to the following general reaction schemes.

Reaction Scheme I

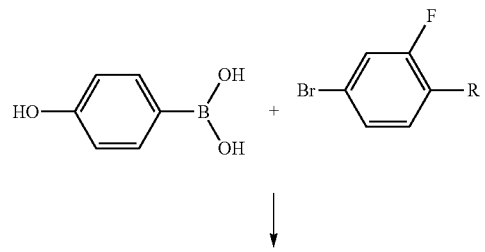

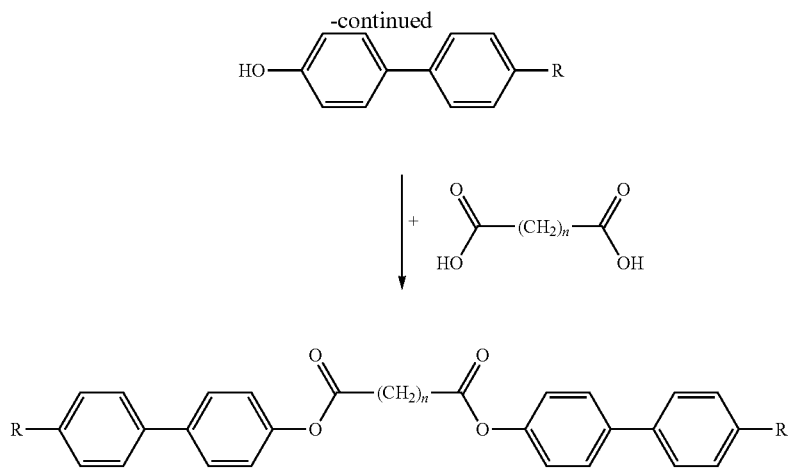

wherein n is an integer of 3 or from 5 to 15, preferably 5, 7 or 9, R independently in each occurrence has one of the meanings given for $R^{11}$ and in the second occurrence alternatively may have one of the additional meanings given for $R^{12}$ including the preferred meanings of these groups, and the conditions of the successive reactions are as follows:

a) $Pd(PPh_3)_2Cl_2$, NaCO3, THF, under reflux
b) DCC, DMAP, DCM, 25° C.

All phenylene moieties shown in this scheme and in the following schemes may independently of each other be optionally bearing one, two or three, preferably one or two, F atoms or one Cl atom or one Cl and one F atom.

An exemplary reaction scheme for the preparation of such a fluorinated compound bearing two $OCF_3$ end group is shown in the following scheme.

wherein n is an integer of 3 or from 5 to 15, preferably 5, 7 or 9 and the conditions of the successive reactions are as follows:

a) $Pd(PPh_3)_2Cl_2$, NaCO3, THF, under reflux;
b) DCC, DMAP, DCM, 25° C.

An exemplary reaction scheme for the preparation of non-symmetric fluorinated compound comprising one fluorinated phenylene ring and bearing two different end groups, one $OCF_3$ and one CN group, is shown in the following scheme.

Reaction Scheme II

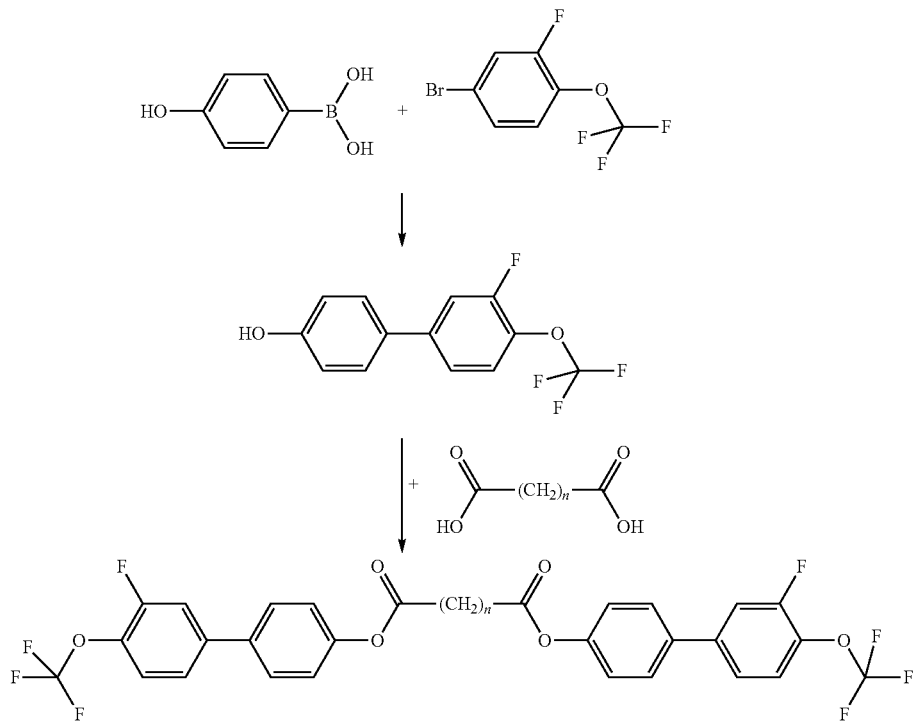

Reaction Scheme III
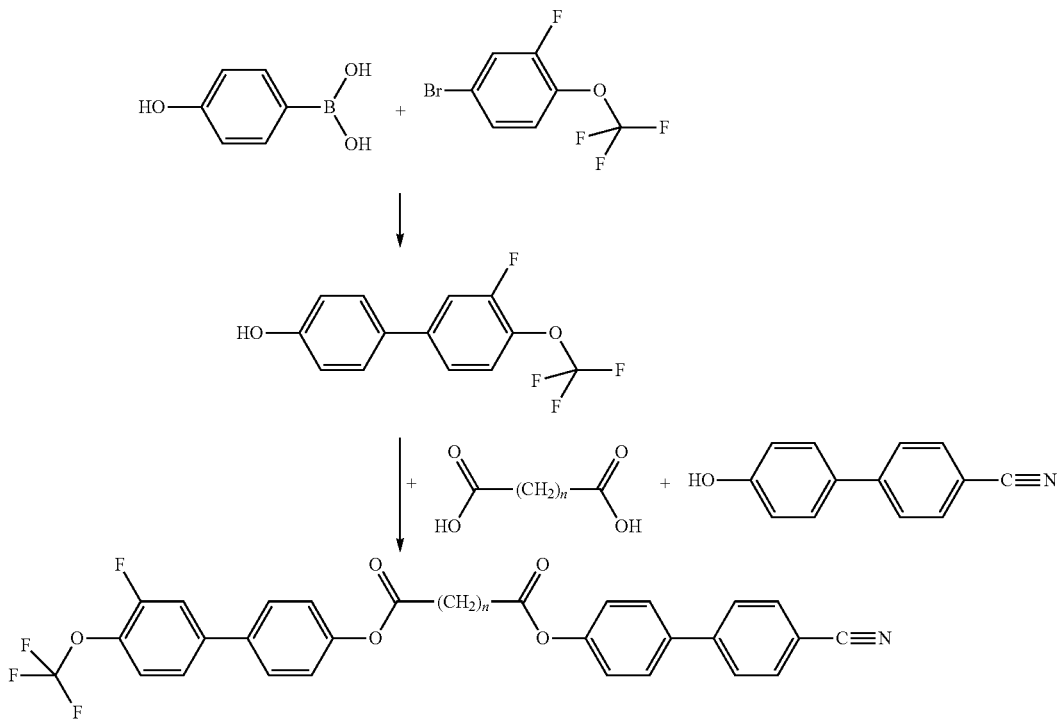
wherein n is an integer of 3 or from 5 to 15, preferably 5, 7 or 9 and the conditions of the successive reactions are as follows:
a) Pd(PPh$_3$)$_2$Cl$_2$, NaCO3, THF, under reflux;
b) DCC, DMAP, DCM, 25° C.
Reaction Scheme IV
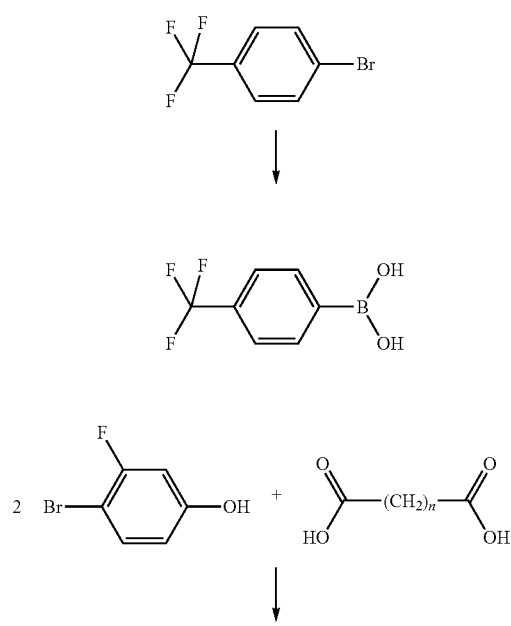

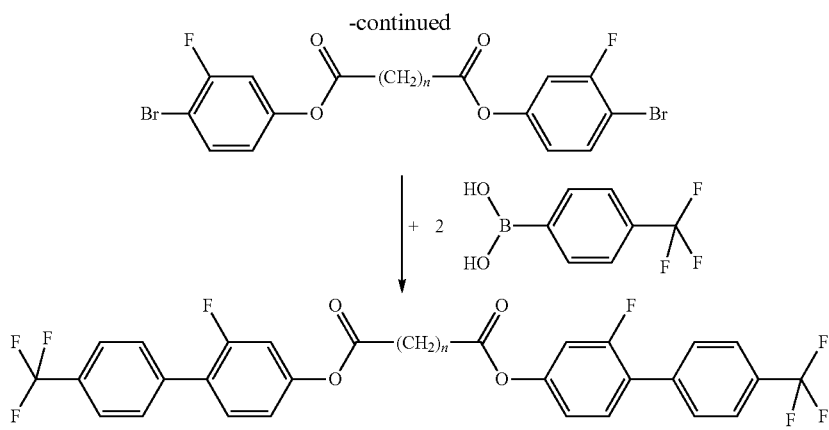

wherein n is an integer of 3 or from 5 to 15, preferably 5, 7 or 9 and the conditions of the successive reactions are as follows:

a) Mg, THF, (MeO)$_3$B;
b) DCC, DMAP, DCM, 25° C.; and
c) Pd(PPh$_3$)$_2$Cl$_2$, NaCO3, THF, under reflux.

Reaction Scheme V

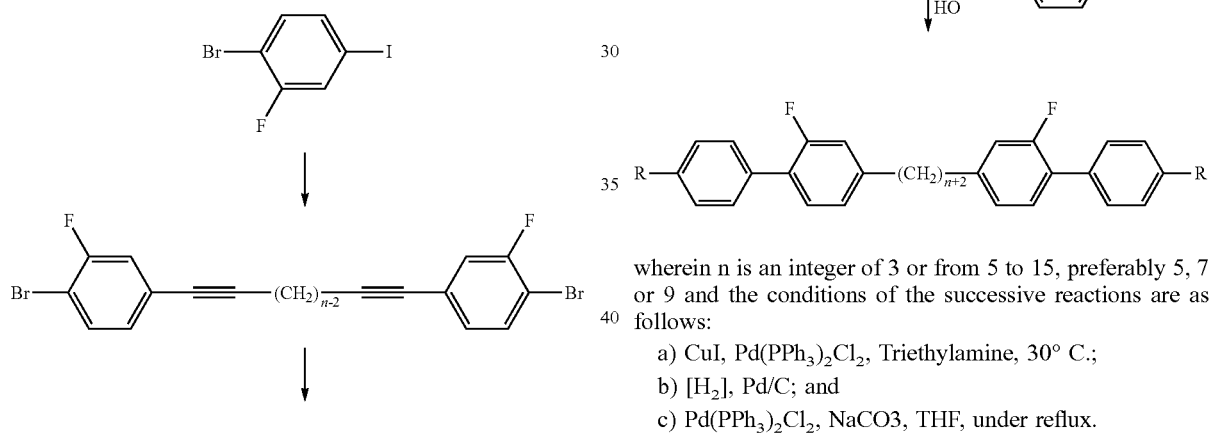

-continued wherein n is an integer of 3 or from 5 to 15, preferably 5, 7 or 9 and the conditions of the successive reactions are as follows:

a) CuI, Pd(PPh$_3$)$_2$Cl$_2$, Triethylamine, 30° C.;
b) [H$_2$], Pd/C; and
c) Pd(PPh$_3$)$_2$Cl$_2$, NaCO3, THF, under reflux.

Reaction Scheme VI

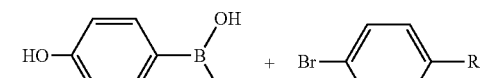

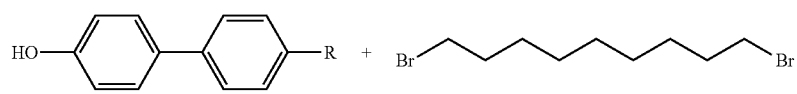

-continued

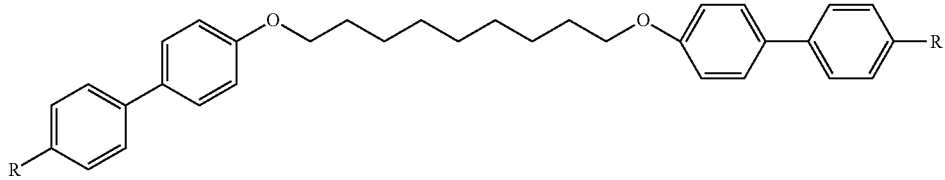

wherein n is an integer of 3 or from 5 to 15, preferably 5, 7 or 9 and the conditions of the successive reactions are as follows:
  a) Pd(PPh$_3$)$_2$Cl$_2$, NaCO3, THF, under reflux; and
  b) K$_2$CO$_3$, butanone, 80° C.

Another object of the invention is the use of bimesogenic compounds of formula I in liquid crystalline media.

Compounds of formula I, when added to a nematic liquid crystalline mixture, producing a phase below the nematic. In this context, a first indication of the influence of bimeso- Reaction Scheme VII

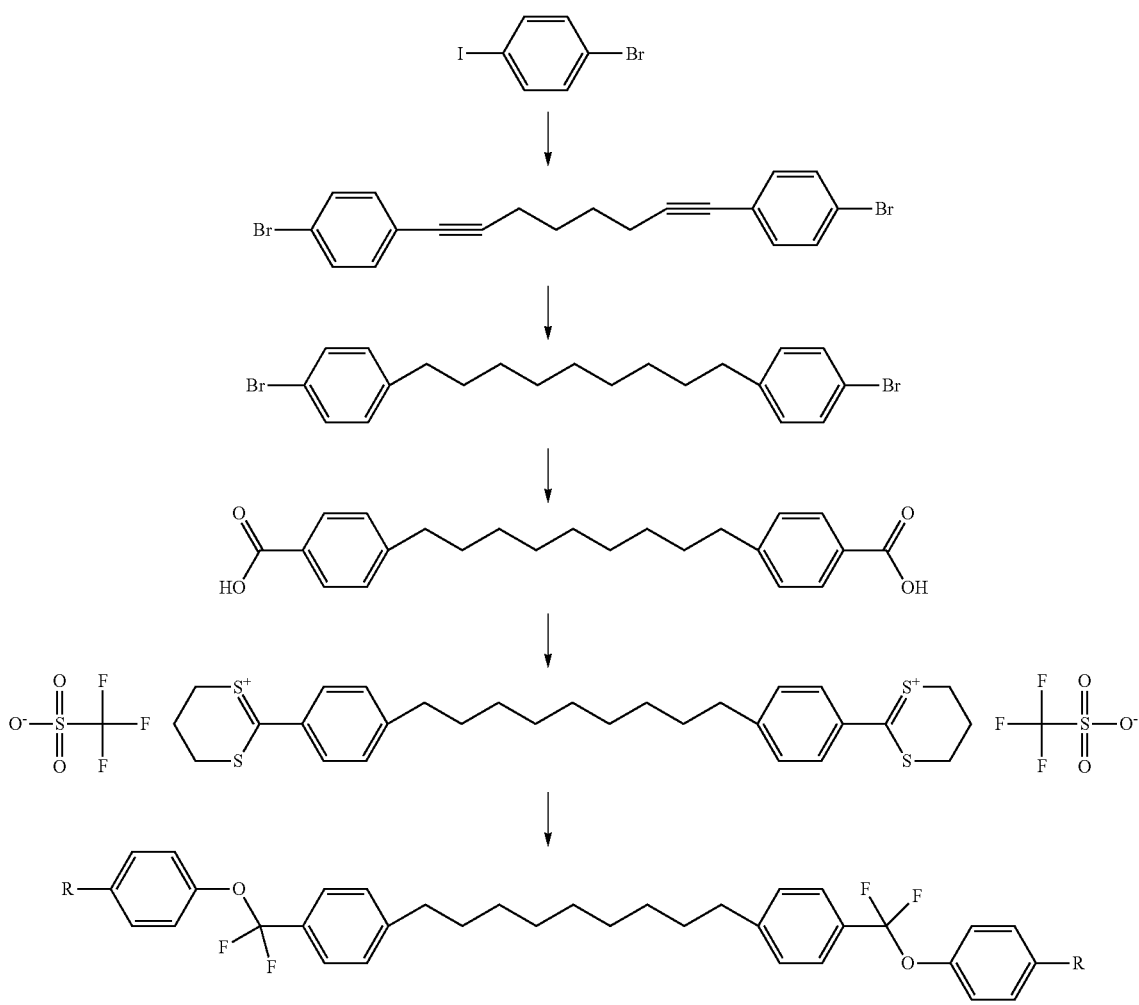

wherein R is as defined under scheme, and the chain length of the central linking group, i.e. the number of methylen groups, may 3 or 5 to 15, preferably 3, 5, 7 or 9 and the conditions of the successive reactions are as follows:
  a) CuI, Pd(PPh$_3$)$_2$Cl$_2$, Triethylamine, 30° C.;
  b) [H$_2$], Pd/C;
  c) n-BuLi, THF, −70 0° C., CO$_2$;
  d) HSC$_3$H$_6$SH, CF$_3$SO$_3$H, 130° C.; and
  e) N(C$_2$H$_5$)$_3$, 3HF.N(C$_2$H$_5$)$_3$, −70° C.

genic compounds on nematic liquid crystal mixtures was reported by Barnes, P. J., Douglas, A. G., Heeks, S. K., Luckhurst, G. R., Liquid Crystals, 1993, Vol. 13, No. 4, 603-613. This reference exemplifies highly polar alkyl spacered dimers and perceives a phase below the nematic, concluding it is a type of smectic.

A photo evidence of an existing mesophase below the nematic phase was published by Henderson, P. A., Niemeyer, O., Imrie, C. T. in Liquid Crystals, 2001, Vol. 28, No. 3, 463-472, which was not further investigated.

In Liquid Crystals, 2005, Vol. 32, No. 11-12, 1499-1513 Henderson, P. A., Seddon, J. M. and Imrie, C. T. reported, that the new phase below the nematic belonged in some special examples to a smectic C phase. A additional nematic phase below the first nematic was reported by Panov, V. P., Ngaraj, M., Vij, J. K., Panarin, Y. P., Kohlmeier, A., Tamba, M. G., Lewis, R. A. and Mehl, G. H. in Phys. Rev. Lett. 2010, 105, 1678011-1678014.

In this context, liquid crystal mixtures comprising the new and inventive bimesogenic compounds of formula I show also a novel mesophase that is being assigned as a second nematic phase. This mesophase exists at a lower temperature than the original nematic liquid crystalline phase and has been observed in the unique mixture concepts presented by this application.

Accordingly, the bimesogenic compounds of formula I according to the present invention allow the second nematic phase to be induced in nematic mixtures that do not have this phase normally. Furthermore, varying the amounts of compounds of formula I allow the phase behaviour of the second nematic to be tailored to the required temperature.

The invention thus relates to a liquid-crystalline medium which comprises at least one compound of the formula I.

Some preferred embodiments of the mixtures according to the invention are indicated below.

Preferred are compounds of formula I wherein the mesogenic groups $MG^{11}$ and $MG^{12}$ at each occurrence independently from each other comprise one, two or three six-membered rings, preferably two or three six-membered rings.

Particularly preferred are the partial formulae II-1, II-4, II-6, II-7, II-13, II-14, II-15, II-16, II-17 and I-18.

Preferably $R^{11}$ and $R^{12}$ in formula I are selected of H, F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of H, F, Cl, CN, $OCH_3$ and $OCF_3$, especially of H, F, CN and $OCF_3$.

Typical spacer groups ($Sp^1$) are for example $—(CH_2)_o—$, $—(CH_2CH_2O)_p—CH_2CH_2—$, with o being 1, 3 or an integer from 5 to 40, in particular from 1, 3 or 5 to 25, very preferably from 5 to 15, and p being an integer from 1 to 8, in particular 1, 2, 3 or 4.

Preferred are compounds of formula I wherein $R^{11}$-$MG^{11}$-$X^{11}$— and $R^{12}$-$MG^{12}$-$X^{12}$— in formula I are identical.

The media according to the invention preferably comprise one, two, three, four or more, preferably one, two or three, compounds of the formula I.

The amount of compounds of formula I in the liquid crystalline medium is preferably from 1 to 50%, in particular from 5 to 40%, very preferably 10 to 30% by weight of the total mixture.

In a preferred embodiment the liquid crystalline medium according to the present invention comprises additionally one or more compounds of formula III, like those or similar to those known from GB 2 356 629.

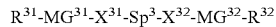

wherein $R^{31}$ and $R^{32}$ are each independently H, F, Cl, CN, NCS or a straight-chain or branched alkyl group with 1 to 25 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —O—CO—O—, —S—CO—,
—CO—S—, —CH═CH—, —CH═CF—, —CF═CF— or —C≡C— in such a manner that oxygen atoms are not linked directly to one another, $MG^{31}$ and $MG^{32}$ are each independently a mesogenic group, $Sp^3$ is a spacer group comprising 5 to 40 C atoms, wherein one or more non-adjacent $CH_2$ groups may also be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH═CH— or —C≡C—, and $X^{31}$ and $X^{32}$ are each independently —O—, —S—, —CO—, —COO—, —OCO—, —O—CO—O—, —CO—NH—, —NH—CO—, —$CH_2CH_2$—, —$OCH_2$—, —$CH_2O$—, —$SCH_2$—, —$CH_2S$—, —CH═CH—, —CH═CH—COO—, —OCO—CH═CH—, —C≡C— or a single bond, and with the condition that compounds of formula I are excluded.

The mesogenic groups $MG^{31}$ and $MG^{32}$ are preferably selected of formula II.

Especially preferred are compounds of formula III wherein $R^{31}$-$MG^{31}$-$X^{31}$— and $R^{32}$-$MG^{32}$-$X^{32}$— are identical.

Another preferred embodiment of the present invention relates to compounds of formula III wherein $R^{31}$-$MG^{31}$-$X^{31}$— and $R^{32}$-$MG^{32}$-$X^{32}$— are different.

Especially preferred are compounds of formula III wherein the mesogenic groups $MG^{31}$ and $MG^{32}$ comprise one, two or three six-membered rings very preferably are the mesogenic groups selected from formula II as listed below.

For $MG^{31}$ and $MG^{32}$ in formula III are particularly preferred are the subformulae II-1, II-4, II-6, II-7, II-13, II-14, II-15, II-16, II-17 and II-18. In these preferred groups Z in each case independently has one of the meanings of $Z^1$ as given in formula II. Preferably Z is —COO—, —OCO—, —$CH_2CH_2$—, —C≡C— or a single bond.

Very preferably the mesogenic groups $MG^{31}$ and $MG^{32}$ are selected from the formulae IIa to IIo and their mirror images.

In case of compounds with a unon-polar group, $R^{31}$ and $R^{32}$ are preferably alkyl with up to 15 C atoms or alkoxy with 2 to 15 C atoms.

If $R^{31}$ or $R^{32}$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In case of a compounds with a terminal polar group, $R^{31}$ and $R^{32}$ are selected from CN, $NO_2$, halogen, $OCH_3$, OCN, SCN, $COR^x$, $COOR^x$ or a mono-oligo- or polyfluorinated alkyl or alkoxy group with 1 to 4 C atoms. $R^x$ is optionally fluorinated alkyl with 1 to 4, preferably 1 to 3 C atoms. Halogen is preferably F or Cl.

Especially preferably $R^{31}$ and $R^{32}$ in formula III are selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of F, Cl, CN, $OCH_3$ and $OCF_3$.

As for the spacer group $Sp^3$ in formula III all groups can be used that are known for this purpose to the skilled in the art. The spacer group Sp is preferably a linear or branched alkylene group having 5 to 40 C atoms, in particular 5 to 25 C atoms, very preferably 5 to 15 C atoms, in which, in addition, one or more non-adjacent $CH_2$ groups may be replaced by —O—, —S—, —NH—, —N(CH₃)—, —CO—, —O—CO—, —S—CO—, —O—COO—, —CO—S—, —CO—O—, —CH(halogen)-, —CH(CN)—, —CH═CH— or —C≡C—.

Typical spacer groups are for example —(CH₂)$_o$—, —(CH₂CH₂O)$_p$—CH₂CH₂—, —CH₂CH₂—S—CH₂CH₂— or —CH₂CH₂—NH—CH₂CH₂—, with o being an integer from 5 to 40, in particular from 5 to 25, very preferably from 5 to 15, and p being an integer from 1 to 8, in particular 1, 2, 3 or 4.

Preferred spacer groups are pentylene, hexylene, heptylene, octylene, nonylene, decylene, undecylene, dodecylene, octadecylene, diethyleneoxyethylene, dimethyleneoxybutylene, pentenylene, heptenylene, nonenylene and undecenylene, for example.

Especially preferred are inventive compounds of formula III wherein $Sp^3$ is denoting alkylene with 5 to 15 C atoms. Straight-chain alkylene groups are especially preferred.

In another preferred embodiment of the invention the chiral compounds of formula III comprise at least one spacer group $Sp^1$ that is a chiral group of the formula IV.

$X^{31}$ and $X^{32}$ in formula III denote preferably —O—, —CO—, —COO—, —OCO—, —O—CO—O— or a single bond. Particularly preferred are the following compounds selected from formulae III-1 to III-4:

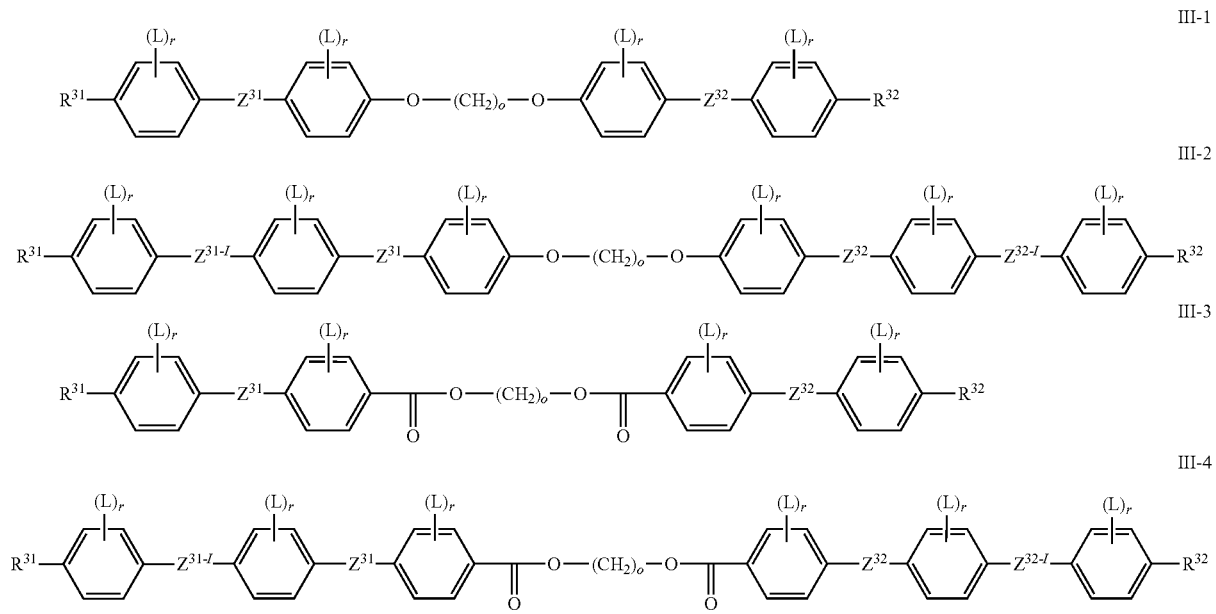

wherein $R^{31}$, $R^{32}$ have the meaning given under formula III, $Z^{31}$ and $Z^{31-I}$ are defined as $Z^{31}$ and $Z^{32}$ and $Z^{32-I}$ are respectively the reverse groups of $Z^{31}$ and $Z^{32-I}$ in formula III and o and r are independently at each occurrence as defined above, including the preferred meanings of these groups and wherein L is in each occurrence independently of each other preferably F, Cl, CN, OH, NO₂ or an optionally fluorinated alkyl, alkoxy or alkanoyl group with 1 to 7 C atoms, very preferably F, Cl, CN, OH, NO₂, CH₃, C₂H₅, OCH₃, OC₂H₅, COCH₃, COC₂H₅, COOCH₃, COOC₂H₅, CF₃, OCF₃, OCHF₂, OC₂F₅, in particular F, Cl, CN, CH₃, C₂H₅, OCH₃, COCH₃ and OCF₃, most preferably F, Cl, CH₃, OCH₃ and COCH₃ and from which compounds of formula I are excluded.

Particularly preferred mixtures according to the invention comprise one or more compounds of the formulae III-1a to III-1e and III-3a to III-3b.

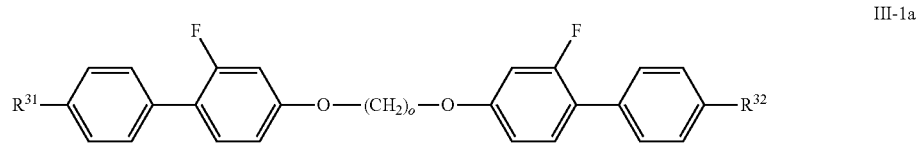

-continued

III-1b
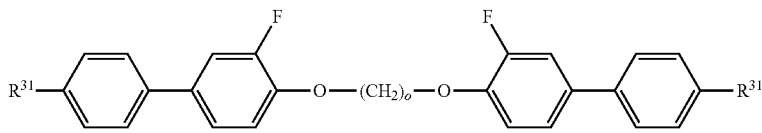

III-1c
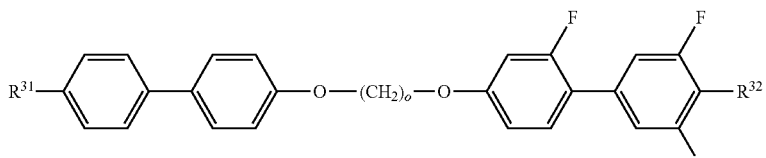

III-1d
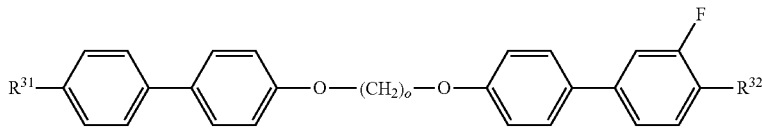

III-1e
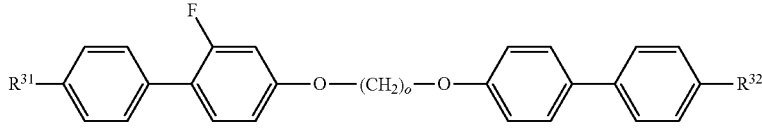

III-3a
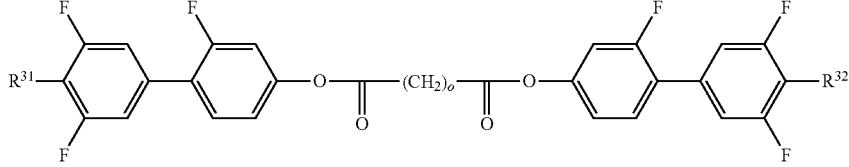

III-3b
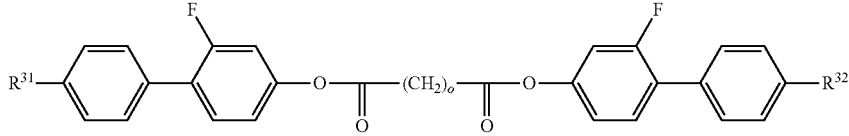

wherein the parameters are as defined above.

In a preferred embodiment of the invention the liquid crystalline medium is consisting of 2 to 25, preferably 3 to 15 compounds of formula III.

The amount of compounds of formula III in the liquid crystalline medium is preferably from 10 to 95%, in particular from 15 to 90%, very preferably 20 to 85% by weight of the total mixture.

Preferably, the proportion of compounds of the formulae III-1a and/or III-1b and/or III-1c and/or III-1e and or III-3a and/or III-3b in the medium as a whole is preferably at least 70% by weight.

Particularly preferred media according to the invention comprise at least one or more chiral dopants which themselves do not necessarily have to show a liquid crystalline phase and give good uniform alignment themselves.

Especially preferred are chiral dopants selected from formula IV

IV
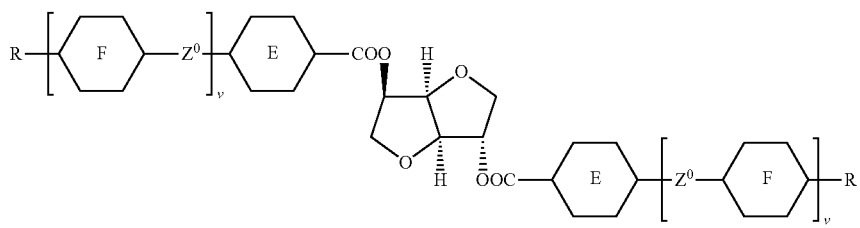

and formula V

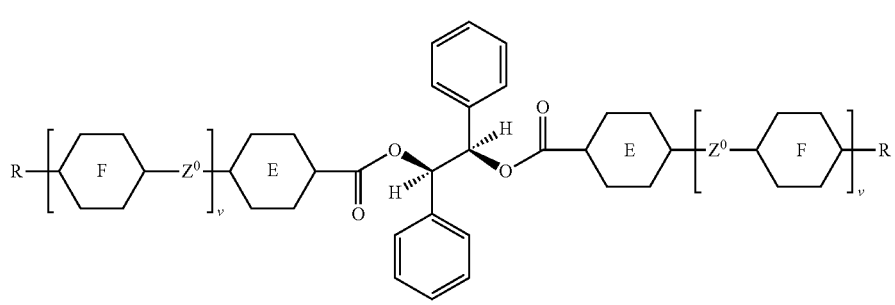

including the respective (S,S) enantiomer, wherein E and F are each independently 1,4-phenylene or trans-1,4-cyclohexylene, v is 0 or 1, $Z^0$ is —COO—, —OCO—, —CH$_2$CH$_2$— or a single bond, and R is alkyl, alkoxy or alkanoyl with 1 to 12 C atoms.

The compounds of formula IV and their synthesis are described in WO 98/00428. Especially preferred is the compound CD-1, as shown in table D below. The compounds of formula V and their synthesis are described in GB 2,328,207.

Especially preferred are chiral dopants with a high helical twisting power (HTP), in particular those disclosed in WO 98/00428.

Further typically used chiral dopants are e.g. the commercially available R/S-5011, CD-1, R/S-811 and CB-15 (from Merck KGaA, Darmstadt, Germany).

The above mentioned chiral compounds R/S-5011 and CD-1 and the compounds of formula IV and V exhibit a very high helical twisting power (HTP), and are therefore particularly useful for the purpose of the present invention.

The liquid crystalline medium preferably comprises preferably 1 to 5, in particular 1 to 3, very preferably 1 or 2 chiral dopants, preferably selected from the above formula IV, in particular CD-1, and/or formula V and/or R-5011 or S-5011, very preferably the chiral compound is R-5011, S-5011 or CD-1.

The amount of chiral compounds in the liquid crystalline medium is preferably from 1 to 20%, in particular from 1 to 15%, very preferably 1 to 10% by weight of the total mixture.

Further preferred are liquid crystalline media comprising one or more additives selected from the following formula VI

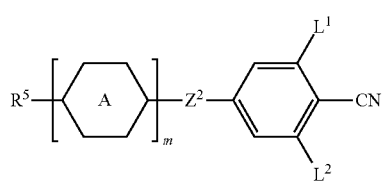

VI wherein $R^5$ is alkyl, alkoxy, alkenyl or alkenyloxy with up to 12 C atoms, is

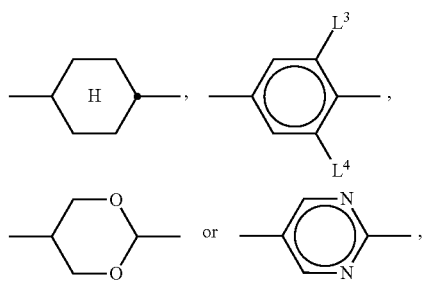

$L^1$ through $L^4$ are each independently H or F, $Z^2$ is —COO—, —CH$_2$CH$_2$— or a single bond, m is 1 or 2

Particularly preferred compounds of formula VI are selected from the following formulae

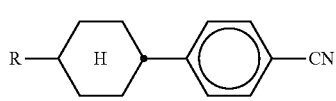

VIa

VIb

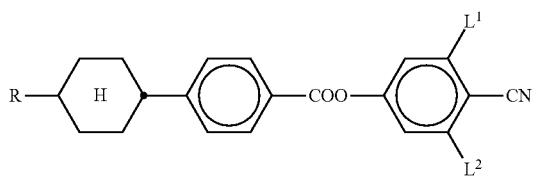

VIc

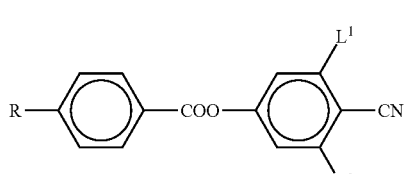

-continued

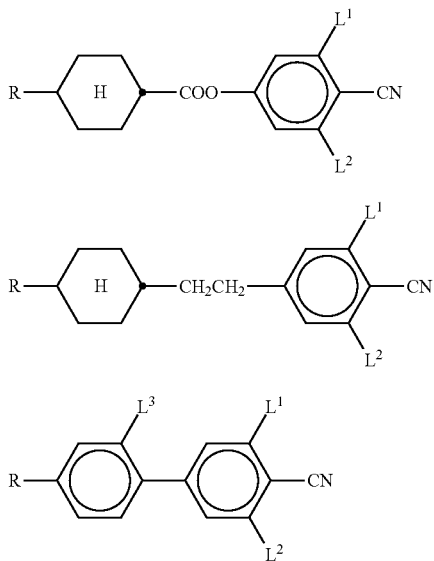

wherein, R has one of the meanings of $R^5$ above and $L^1$, $L^2$ and $L^3$ have the above meanings.

The liquid crystalline medium preferably comprises preferably 1 to 5, in particular 1 to 3, very preferably 1 or 2, preferably selected from the above formulae VIa to VIf, very preferably from formulae VIf.

The amount of suitable additives of formula VI in the liquid crystalline medium is preferably from 1 to 20%, in particular from 1 to 15%, very preferably 1 to 10% by weight of the total mixture.

The liquid crystal media according to the present invention may contain further additives in usual concentrations. The total concentration of these further constituents is in the range of 0.1% to 10%, preferably 0.1% to 6%, based on the total mixture. The concentrations of the individual compounds used each are preferably in the range of 0.1% to 3%. The concentration of these and of similar additives is not taken into consideration for the values and ranges of the concentrations of the liquid crystal components and compounds of the liquid crystal media in this application. This also holds for the concentration of the dichroic dyes used in the mixtures, which are not counted when the concentrations of the compounds respectively the components of the host medium are specified. The concentration of the respective additives is always given relative to the final doped mixture.

The liquid crystal media according to the present invention consists of several compounds, preferably of 3 to 30, more preferably of 4 to 20 and most preferably of 4 to 16 compounds. These compounds are mixed in conventional way. As a rule, the required amount of the compound used in the smaller amount is dissolved in the compound used in the greater amount. In case the temperature is above the clearing point of the compound used in the higher concentration, it is particularly easy to observe completion of the process of dissolution. It is, however, also possible to prepare the media by other conventional ways, e.g. using so called pre-mixtures, which can be e.g. homologous or eutectic mixtures of compounds or using so called multi-bottle-systems, the constituents of which are ready to use mixtures themselves.

Particularly preferred mixture concepts are indicated below: (the acronyms used are explained in Table A).

The mixtures according to the invention preferably comprise
one or more compounds of formula I in a total concentration in the range from 1 to 50%, in particular from 5 to 40%, very preferably 10 to 30% by weight of the total mixture
and/or
one or more compounds of formula III in a total concentration in the range from 10 to 95%, in particular from 15 to 90%, very preferably 20 to 85% by weight of the total mixture, preferably these compounds are selected from formulae III-1a to III-1e and III-3a to III-3b especially preferred they comprise
N-PGI-ZI-n-Z-GP-N, preferably N-PGI-ZI-7-Z-GP-N and/or N-PGI-ZI-9-Z-GP-N preferably in concentrations >5%, in particular 10-30%, based on the mixture as a whole,
and/or
F-UIGI-ZI-n-Z-GU-F, preferably F-UIGI-ZI-9-Z-GU-F, preferably in concentrations >5%, in particular 10-30%, based on the mixture as a whole,
and/or
F-PGI-O-n-O—PP—N, preferably F-PGI-O-9-O—PP—, preferably in concentrations of >1%, in particular 1-20%, based on the mixture as a whole,
and/or
N—PP—O-n-O-PG-OT, preferably N—PP—O-7-O-PG-OT, preferably in concentrations of >5%, in particular 5-30%, based on the mixture as a whole,
and/or
N—PP—O-n-O-GU-F, preferably N—PP—O-9-O-GU-F, preferably in concentrations of >1%, in particular 1-20%, based on the mixture as a whole,
and/or
F-PGI-O-n-O-GP-F, preferably F-PGI-O-7-O-GP-F and/or F-PGI-O-9-O-GP-F preferably in concentrations of >1%, in particular 1-20%, based on the mixture as a whole,
and/or
N-GIGIGI-n-GGG-N, in particular N-GIGIGI-9-GGG-N, preferably in concentration >5%, in particular 10-30%, based on the mixture as a whole,
and/or
N-PGI-n-GP-N, preferably N-PGI-9-GP-N, preferably in concentrations >5%, in particular 15-50%, based on the mixture as a whole,
and/or
one or more suitable additives of formula VI in a total concentration in the range from 1 to 20%, in particular from 1 to 15%, very preferably 1 to 10% by weight of the total mixture, preferably are these compounds selected from formula VIa to VIf, especially preferred they comprise
PP-n-N, preferably in concentrations of >1%, in particular 1-20%, based on the mixture as a whole,
and/or
one or more chiral compounds preferably in a total concentration in the range from 1 to 20%, in particular from 1 to 15%, very preferably 1 to 10% by weight of the total mixture, preferably these compounds are selected from formula IV, V, and R-5011 or S-5011, especially preferred they comprise
R-5011, S-5011 or CD-1, preferably in a concentration of >1%, in particular 1-20%, based on the mixture as a whole.

The bimesogenic compounds of formula I and the liquid crystalline media comprising them can be used in liquid crystal displays, such as STN, TN, AMD-TN, temperature compensation, guest-host, phase change or surface stabilized or polymer stabilized cholesteric texture (SSCT, PSCT) displays, in particular in flexoelectric devices, in active and passive optical elements like polarizers, compensators, reflectors, alignment layers, color filters or holographic elements, in adhesives, synthetic resins with anisotropic mechanical properties, cosmetics, diagnostics, liquid crystal pigments, for decorative and security applications, in nonlinear optics, optical information storage or as chiral dopants.

The compounds of formula I and the mixtures obtainable thereof are particularly useful for flexoelectric liquid crystal display. Thus, another object of the present invention is a flexoelectric display comprising one or more compounds of formula I or comprising a liquid crystal medium comprising one or more compounds of formula I.

The inventive bimesogenic compounds of formula I and the mixtures thereof can be aligned in their cholesteric phase into different states of orientation by methods that are known to the expert, such as surface treatment or electric fields. For example, they can be aligned into the planar (Grandjean) state, into the focal conic state or into the homeotropic state. Inventive compounds of formula I comprising polar groups with a strong dipole moment can further be subjected to flexoelectric switching, and can thus be used in electrooptical switches or liquid crystal displays.

The switching between different states of orientation according to a preferred embodiment of the present invention is exemplarily described below in detail for a sample of an inventive compound of formula I.

According to this preferred embodiment, the sample is placed into a cell comprising two plane-parallel glass plates coated with electrode layers, e.g. ITO layers, and aligned in its cholesteric phase into a planar state wherein the axis of the cholesteric helix is oriented normal to the cell walls. This state is also known as Grandjean state, and the texture of the sample, which is observable e.g. in a polarization microscope, as Grandjean texture. Planar alignment can be achieved e.g. by surface treatment of the cell walls, for example by rubbing and/or coating with an alignment layer such as polyimide.

A Grandjean state with a high quality of alignment and only few defects can further be achieved by heating the sample to the isotropic phase, subsequently cooling to the chiral nematic phase at a temperature close to the chiral nematic-isotropic phase transition, and rubbing the cell.

In the planar state, the sample shows selective reflection of incident light, with the central wavelength of reflection depending on the helical pitch and the mean refractive index of the material.

When an electric field is applied to the electrodes, for example with a frequency from 10 Hz to 1 kHz, and an amplitude of up to 12 $V_{rms}$/m, the sample is being switched into a homeotropic state where the helix is unwound and the molecules are oriented parallel to the field, i.e. normal to the plane of the electrodes. In the homeotropic state, the sample is transmissive when viewed in normal daylight, and appears black when being put between crossed polarizers.

Upon reduction or removal of the electric field in the homeotropic state, the sample adopts a focal conic texture, where the molecules exhibit a helically twisted structure with the helical axis being oriented perpendicular to the field, i.e. parallel to the plane of the electrodes. A focal conic state can also be achieved by applying only a weak electric field to a sample in its planar state. In the focal conic state the sample is scattering when viewed in normal daylight and appears bright between crossed polarizers.

A sample of an inventive compound in the different states of orientation exhibits different transmission of light. Therefore, the respective state of orientation, as well as its quality of alignment, can be controlled by measuring the light transmission of the sample depending on the strength of the applied electric field. Thereby it is also possible to determine the electric field strength required to achieve specific states of orientation and transitions between these different states.

In a sample of an inventive compound of formula I, the above described focal conic state consists of many disordered birefringent small domains. By applying an electric field greater than the field for nucleation of the focal conic texture, preferably with additional shearing of the cell, a uniformly aligned texture is achieved where the helical axis is parallel to the plane of the electrodes in large, well-aligned areas. In accordance with the literature on state of the art chiral nematic materials, such as P. Rudquist et al., Liq. Cryst. 23 (4), 503 (1997), this texture is also called uniformly-lying helix (ULH) texture. This texture is required to characterize the flexoelectric properties of the inventive compound.

The sequence of textures typically observed in a sample of an inventive compound of formula I on a rubbed polyimide substrate upon increasing or decreasing electric field is given below:

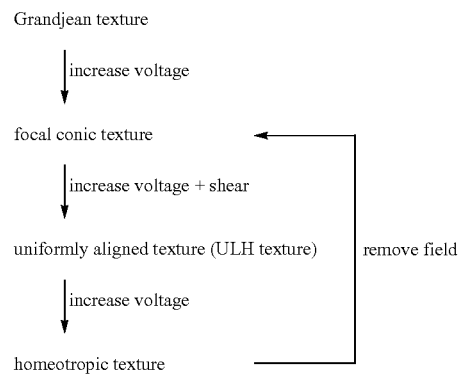

Starting from the ULH texture, the inventive flexoelectric compounds and mixtures can be subjected to flexoelectric switching by application of an electric field. This causes rotation of the optic axis of the material in the plane of the cell substrates, which leads to a change in transmission when placing the material between crossed polarizers. The flexoelectric switching of inventive materials is further described in detail in the introduction above and in the examples.

It is also possible to obtain the ULH texture, starting from the focal conic texture, by applying an electric field with a high frequency, of for example 10 kHz, to the sample whilst cooling slowly from the isotropic phase into the cholesteric phase and shearing the cell. The field frequency may differ for different compounds.

The bimesogenic compounds of formula I are particularly useful in flexoelectric liquid crystal displays as they can easily be aligned into macroscopically uniform orientation, and lead to high values of the elastic constant $k_{11}$ and a high flexoelectric coefficient e in the liquid crystal medium.

The liquid crystal medium preferably exhibits a $k_{11} < 1 \times 10^{-10}$ N, preferably $< 2 \times 10^{-11}$ N, and a flexoelectric coefficient $e > 1 \times 10^{-11}$ C/m, preferably $> 1 \times 10^{-10}$ C/m.

Apart from the use in flexoelectric devices, the inventive bimesogenic compounds as well as mixtures thereof are also suitable for other types of displays and other optical and electrooptical applications, such as optical compensation or polarizing films, color filters, reflective cholesterics, optical rotatory power and optical information storage.

A further aspect of the present invention relates to a display cell wherein the cell walls exhibit hybrid alignment conditions. The term "hybrid alignment" or orientation of a liquid crystal or mesogenic material in a display cell or between two substrates means that the mesogenic groups adjacent to the first cell wall or on the first substrate exhibit homeotropic orientation and the mesogenic groups adjacent to the second cell wall or on the second substrate exhibit planar orientation.

The term "homeotropic alignment" or orientation of a liquid crystal or mesogenic material in a display cell or on a substrate means that the mesogenic groups in the liquid crystal or mesogenic material are oriented substantially perpendicular to the plane of the cell or substrate, respectively.

The term "planar alignment" or orientation of a liquid crystal or mesogenic material in a display cell or on a substrate means that the mesogenic groups in the liquid crystal or mesogenic material are oriented substantially parallel to the plane of the cell or substrate, respectively.

A flexoelectric display according to a preferred embodiment of the present invention comprises two plane parallel substrates, preferably glass plates covered with a transparent conductive layer such as indium tin oxide (ITO) on their inner surfaces, and a flexoelectric liquid crystalline medium provided between the substrates, characterized in that one of the inner substrate surfaces exhibits homeotropic alignment conditions and the opposite inner substrate surface exhibits planar alignment conditions for the liquid crystalline medium.

Planar alignment can be achieved e.g. by means of an alignment layer, for example a layer of rubbed polyimide or sputtered $SiO_x$, that is applied on top of the substrate.

Alternatively it is possible to directly rub the substrate, i.e. without applying an additional alignment layer. For example, rubbing can be achieved by means of a rubbing cloth, such as a velvet cloth, or with a flat bar coated with a rubbing cloth. In a preferred embodiment of the present invention rubbing is achieved by means of a at least one rubbing roller, like e.g. a fast spinning roller that is brushing across the substrate, or by putting the substrate between at least two rollers, wherein in each case at least one of the rollers is optionally covered with a rubbing cloth. In another preferred embodiment of the present invention rubbing is achieved by wrapping the substrate at least partially at a defined angle around a roller that is preferably coated with a rubbing cloth.

Homeotropic alignment can be achieved e.g. by means of an alignment layer coated on top of the substrate. Suitable aligning agents used on glass substrates are for example alkyltrichlorosilane or lecithine, whereas for plastic substrate thin layers of lecithine, silica or high tilt polyimide orientation films as aligning agents may be used. In a preferred embodiment of the invention silica coated plastic film is used as a substrate.

Further suitable methods to achieve planar or homeotropic alignment are described for example in J. Cognard, Mol. Cryst. Liq. Cryst. 78, Supplement 1, 1-77 (1981).

By using a display cell with hybrid alignment conditions, a very high switching angle of flexoelectric switching, fast response times and a good contrast can be achieved.

The flexoelectric display according to present invention may also comprise plastic substrates instead of glass substrates. Plastic film substrates are particularly suitable for rubbing treatment by rubbing rollers as described above.

Another object of the present invention is that compounds of formula I, when added to a nematic liquid crystalline mixture, produce a phase below the nematic.

Accordingly, the bimesogenic compounds of formula I according to the present invention allow the second nematic phase to be induced in nematic mixtures that do not show evidence of this phase normally. Furthermore, varying the amounts of compounds of formula I allow the phase behaviour of the second nematic to be tailored to the required temperature.

Examples for this are given and the mixtures obtainable thereof are particularly useful for flexoelectric liquid crystal display. Thus, another object of the present invention is liquid crystal media comprising one or more compounds of formula I exhibiting a second nematic phase.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

Throughout the present application it is to be understood that the angles of the bonds at a C atom being bound to three adjacent atoms, e.g. in a C=C or C=O double bond or e.g. in a benzene ring, are 120° and that the angles of the bonds at a C atom being bound to two adjacent atoms, e.g. in a C≡C or in a C≡N triple bond or in an allylic position C=C=C are 180°, unless these angles are otherwise restricted, e.g. like being part of small rings, like 3-, 5- or 5-atomic rings, notwithstanding that in some instances in some structural formulae these angles are not represented exactly.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The total concentration of all compounds in the media according to this application is 100%.

In the foregoing and in the following examples, unless otherwise indicated, all temperatures are set forth uncorrected in degrees Celsius and all parts and percentages are by weight.

The following abbreviations are used to illustrate the liquid crystalline phase behavior of the compounds: K=crystalline; N=nematic; N2=second nematic; S or Sm=smectic; Ch=cholesteric; I=isotropic; Tg=glass transition. The numbers between the symbols indicate the phase transition temperatures in ° C.

In the present application and especially in the following examples, the structures of the liquid crystal compounds are represented by abbreviations, which are also called "acronyms". The transformation of the abbreviations into the corresponding structures is straight forward according to the following three tables A to C.

All groups $C_nH_{2n+1}$, $C_mH_{2m+1}$, and $C_lH_{2l+1}$ are preferably straight chain alkyl groups with n, m and l C-atoms, respectively, all groups $C_nH_{2n}$, $C_mH_{2m}$ and $C_lH_{2l}$ are preferably $(CH_2)_n$, $(CH_2)_m$ and $(CH_2)_l$, respectively and —CH=CH— preferably is trans-respectively E vinylene.

Table A lists the symbols used for the ring elements, table B those for the linking groups and table C those for the symbols for the left hand and the right hand end groups of the molecules.

Table D lists exemplary molecular structures together with their respective codes.

TABLE A

| Ring Elements | | | |
|---|---|---|---|
| C | 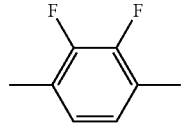 | P | 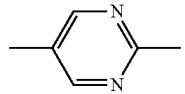 |
| D | 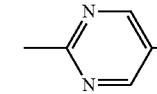 | DI | 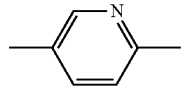 |
| A | 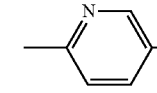 | AI | 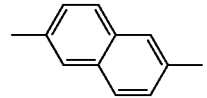 |
| G | 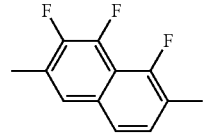 | GI | 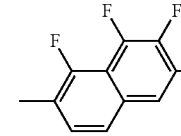 |
| G(Cl) | 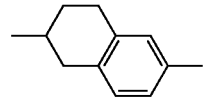 | GI(Cl) | 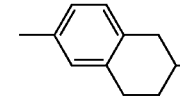 |
| G(1) | 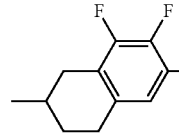 | GI(1) | 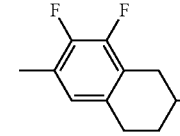 |
| U | 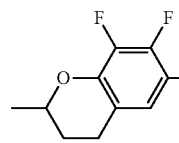 | UI |  |

TABLE A-continued

| Ring Elements | | | |
|---|---|---|---|
| Y | 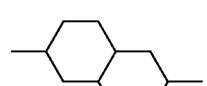 | | |
| M | 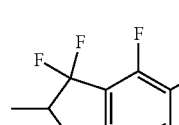 | MI | 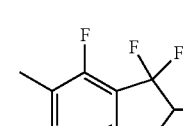 |
| N | 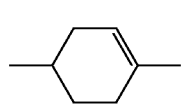 | NI | 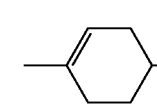 |
| np | 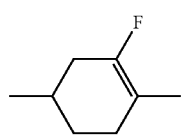 | | |
| n3f | 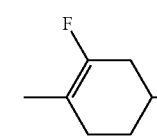 | n3fI |  |
| th |  | thI |  |
| th2f |  | th2fI |  |
| o2f |  | o2fI |  |
| dh |  | | |
| K |  | KI |  |
| L |  | LI |  |
| F |  | FI |  |

TABLE B

| | Linking Groups | |
|---|---|---|
| n | $(-CH_2-)_n$ | "n" is an integer except 0 and 2 |
| E | $-CH_2-CH_2-$ | |
| V | $-CH=CH-$ | |
| T | $-C\equiv C-$ | |
| W | $-CF_2-CF_2-$ | |
| B | $-CF=CF-$ | |
| Z | $-CO-O-$ | |
| ZI | $-O-CO-$ | |
| X | $-CF=CH-$ | |
| XI | $-CH=CF-$ | |
| 1O | $-CH_2-O-$ | |
| O1 | $-O-CH_2-$ | |
| Q | $-CF_2-O-$ | |
| QI | $-O-CF_2-$ | |

TABLE C

| | End Groups |
|---|---|
| | Left hand side, used alone or in combination with others |
| -n- | $C_nH_{2n+1}-$ |
| —nO— | $C_nH_{2n+1}-O-$ |
| —V— | $CH_2=CH-$ |
| —nV— | $C_nH_{2n+1}-CH=CH-$ |
| —Vn— | $CH_2=CH-C_nH_{2n}-$ |
| —nVm— | $C_nH_{2n+1}-CH=CH-C_mH_{2m}-$ |
| —N— | $N\equiv C-$ |
| —S— | $S=C=N-$ |
| —F— | $F-$ |
| —CL— | $Cl-$ |
| —M— | $CFH_2-$ |
| —D— | $CF_2H-$ |
| —T— | $CF_3-$ |
| —MO— | $CFH_2O-$ |
| —DO— | $CF_2HO-$ |
| —TO— | $CF_3O-$ |
| —A— | $H-C\equiv C-$ |
| —nA— | $C_nH_{2n+1}-C\equiv C-$ |
| —NA— | $N\equiv C-C\equiv C-$ |
| | Left hand side, used in combination with others only |
| -...n...- | $(-CH_2-)_n$ |
| —...M...— | $-CFH-$ |

TABLE C-continued

| | End Groups |
|---|---|
| —...D...— | $-CF_2-$ |
| —...V...— | $-CH=CH-$ |
| —...Z...— | $-CO-O-$ |
| —...ZI...— | $-O-CO-$ |
| —...K...— | $-CO-$ |
| —...W...— | $-CF=CF-$ |
| | Right hand side, used alone or in combination with others |
| -n | $-C_nH_{2n+1}$ |
| —nO | $-O-C_nH_{2n+1}$ |
| —V | $-CH=CH_2$ |
| —nV | $-C_nH_{2n}-CH=CH_2$ |
| —Vn | $-CH=CH-C_nH_{2n+1}$ |
| —nVm | $-C_nH_{2n}-CH=CH-C_mH_{2m+1}$ |
| —N | $-C\equiv N$ |
| —S | $-N=C=S$ |
| —F | $-F$ |
| —CL | $-Cl$ |
| —M | $-CFH_2$ |
| —D | $-CF_2H$ |
| —T | $-CF_3$ |
| —OM | $-OCFH_2$ |
| —OD | $-OCF_2H$ |
| —OT | $-OCF_3$ |
| —A | $-C\equiv C-H$ |
| —An | $-C\equiv C-C_nH_{2n+1}$ |
| —AN | $-C\equiv C-C\equiv N$ |
| | Right hand side, used in combination with others only |
| -...n... | $(-CH_2-)_n$ |
| —...M... | $-CFH-$ |
| —...D... | $-CF_2-$ |
| —...V... | $-CH=CH-$ |
| —...Z... | $-CO-O-$ |
| —...ZI... | $-O-CO-$ |
| —...K... | $-CO-$ |
| —...W... | $-CF=CF-$ | wherein n and m each are integers and three points "..." indicate a space for other symbols of this table.

Preferably the liquid crystalline media according to the present invention comprise, besides the compound(s) of formula I one or more compounds selected from the group of compounds of the formulae of the following table.

TABLE D

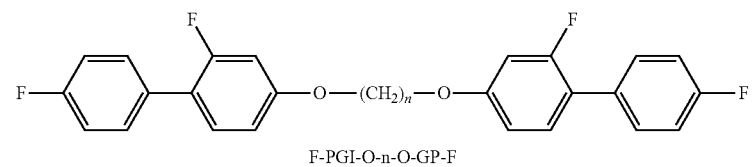

F-PGI-O-n-O-GP-F

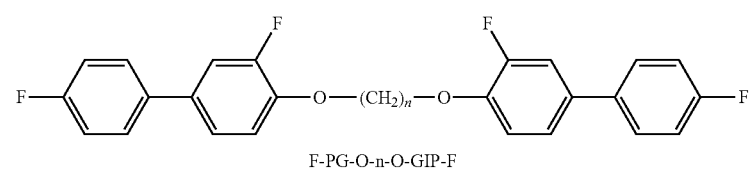

F-PG-O-n-O-GIP-F

TABLE D-continued
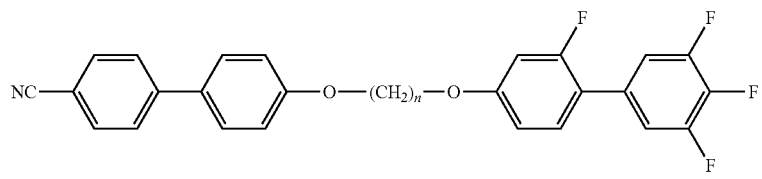
N-PP-O-n-O-GU-F
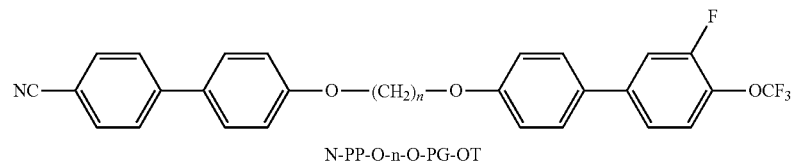
N-PP-O-n-O-PG-OT
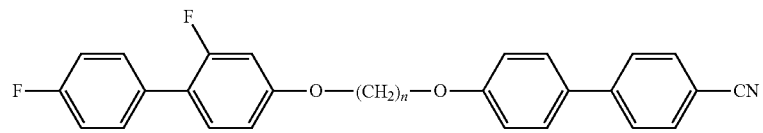
F-PGI-O-n-O-PP-N
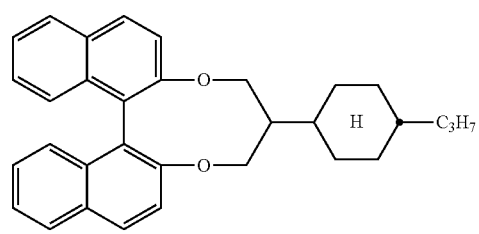
R-5011 respectively S-5011
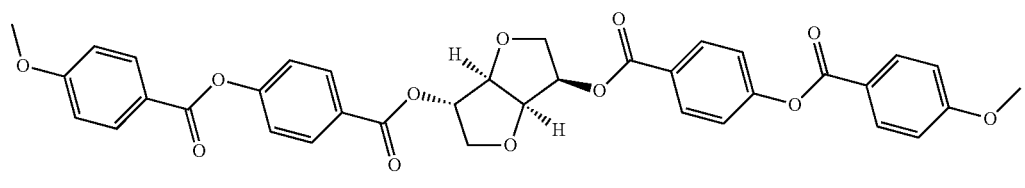
CD-1
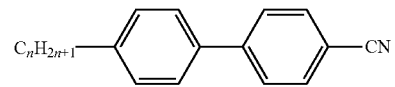
PP-n-N
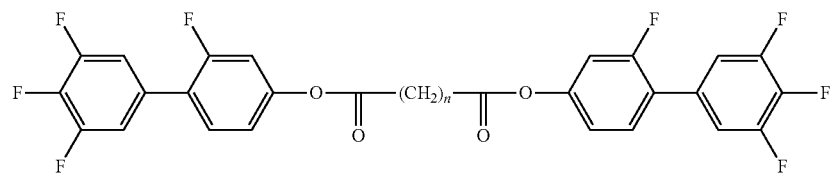
F-UIGI-ZI-n-Z-GU-F
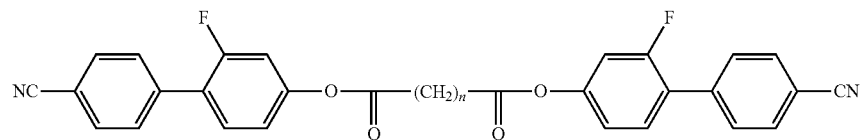
N-PGI-ZI-n-Z-GP-N TABLE D-continued
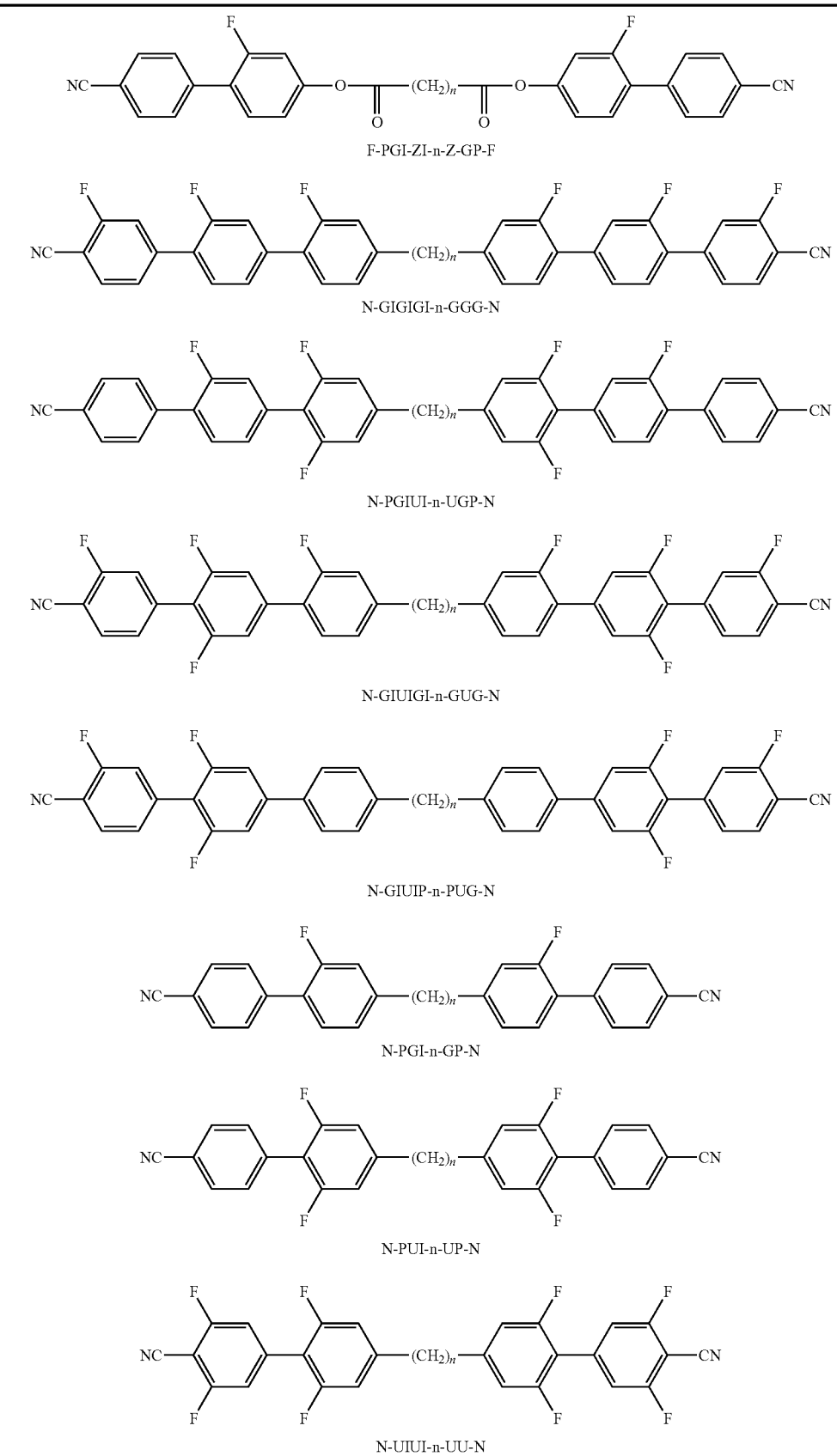

TABLE D-continued
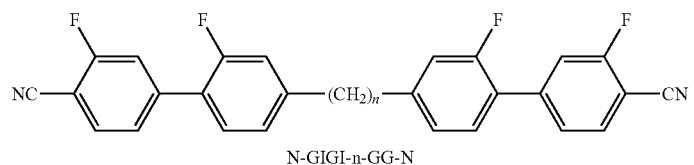
N-GIGI-n-GG-N
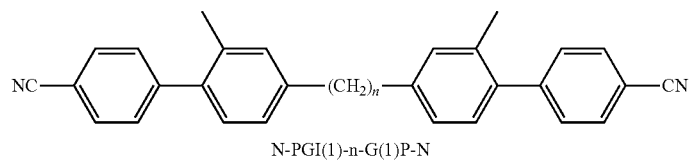
N-PGI(1)-n-G(1)P-N
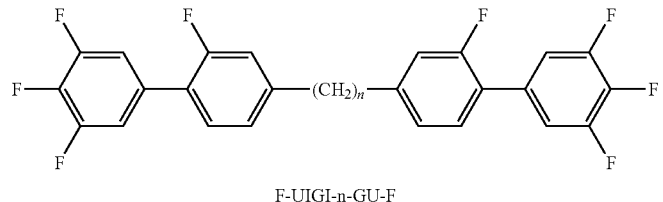
F-UIGI-n-GU-F
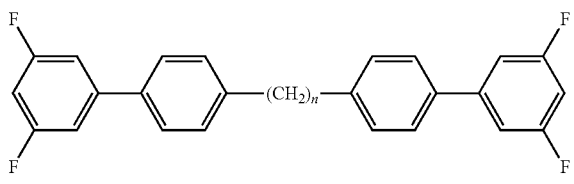
UIP-n-PU
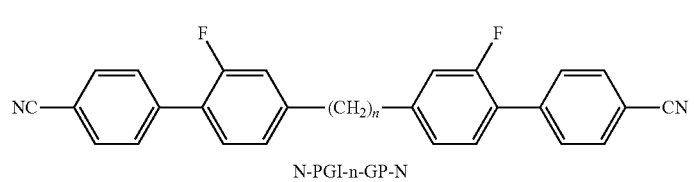
N-PGI-n-GP-N
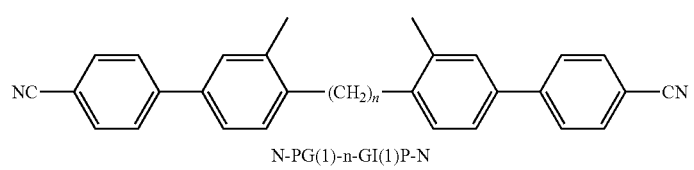
N-PG(1)-n-GI(1)P-N
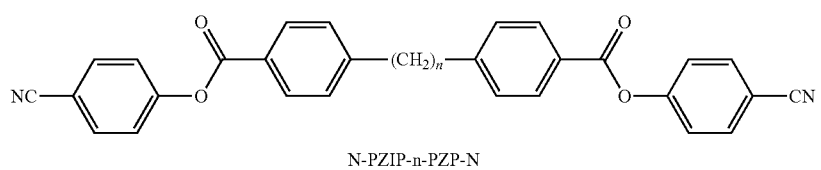
N-PZIP-n-PZP-N
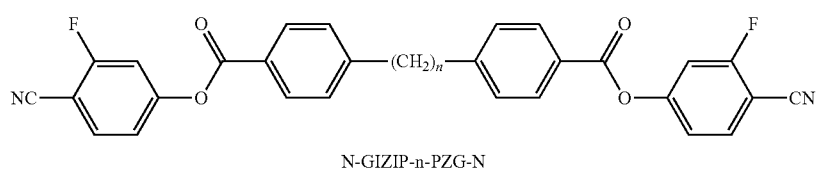
N-GIZIP-n-PZG-N TABLE D-continued
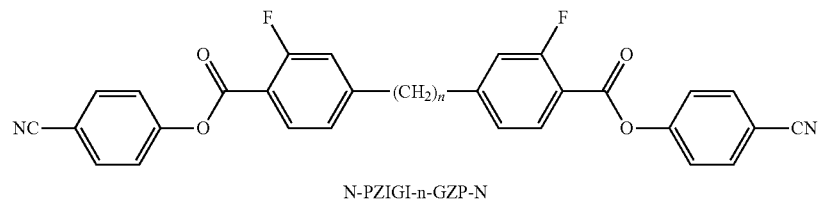
N-PZIGI-n-GZP-N
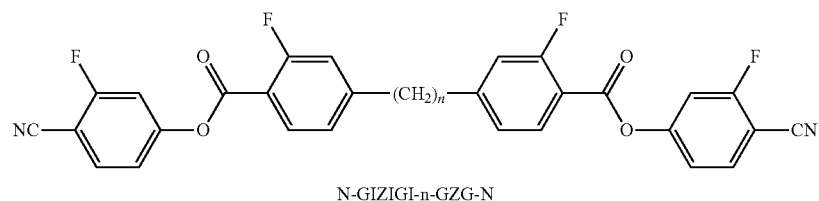
N-GIZIGI-n-GZG-N
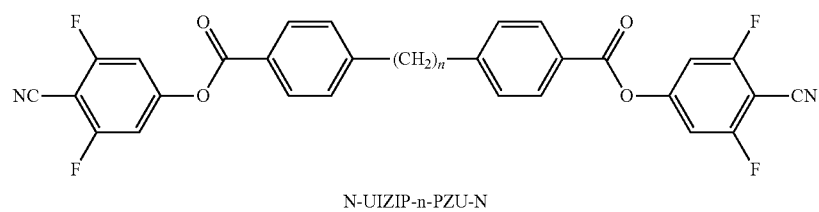
N-UIZIP-n-PZU-N
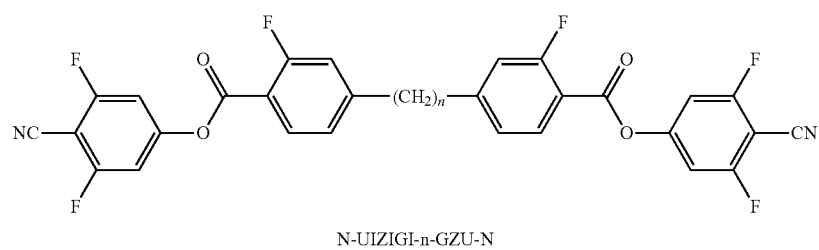
N-UIZIGI-n-GZU-N
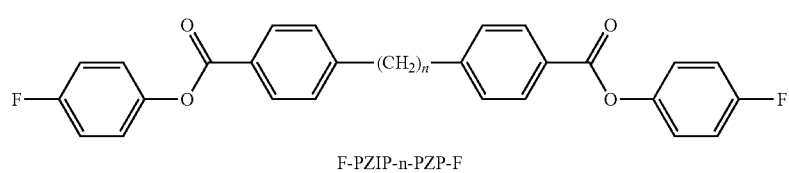
F-PZIP-n-PZP-F
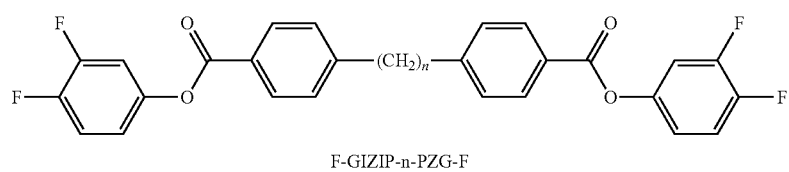
F-GIZIP-n-PZG-F
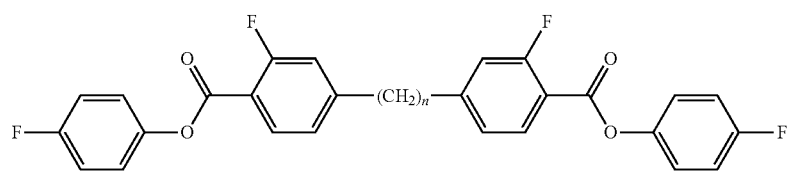
F-PZIGI-n-GZP-F TABLE D-continued
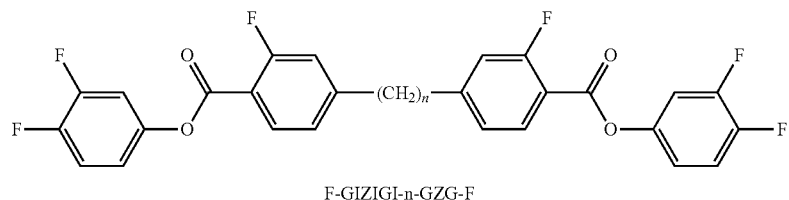
F-GIZIGI-n-GZG-F
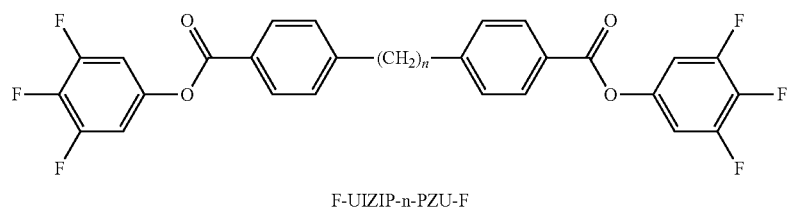
F-UIZIP-n-PZU-F
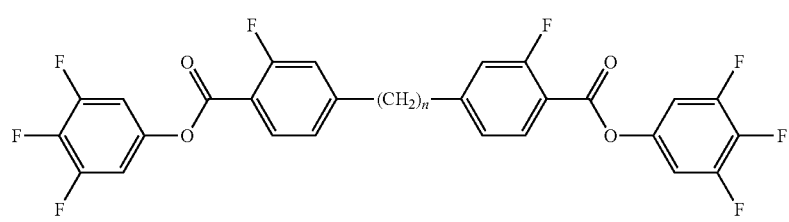
F-UIZIGI-n-GZU-F
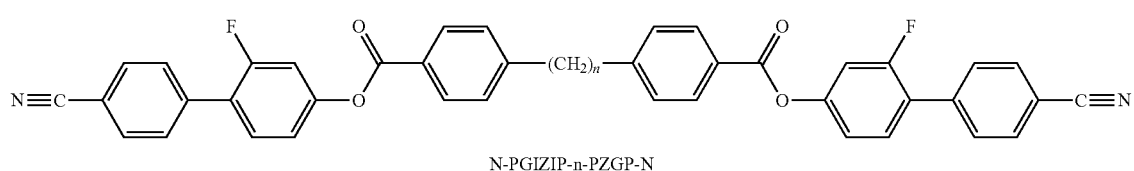
N-PGIZIP-n-PZGP-N
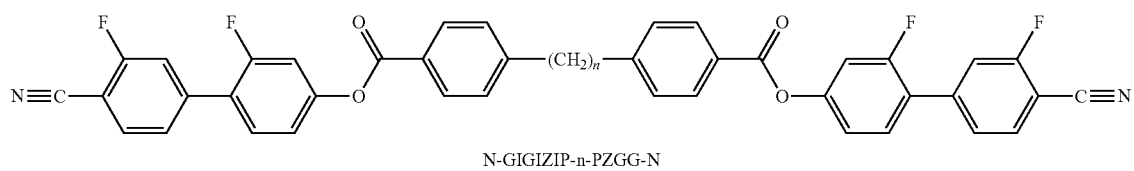
N-GIGIZIP-n-PZGG-N
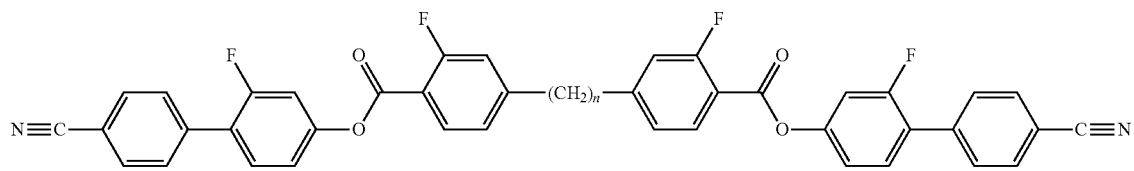
N-PGIZIGI-n-GZGP-N
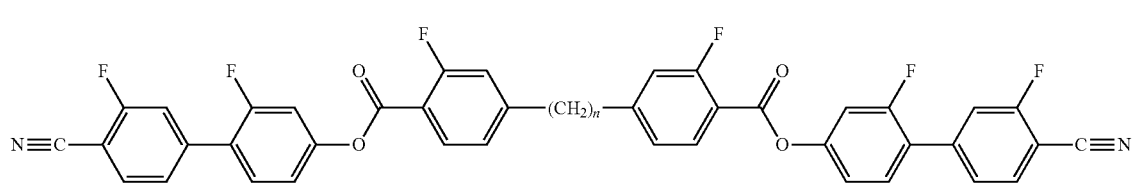
N-GIGIZIGI-n-GZGG-N TABLE D-continued
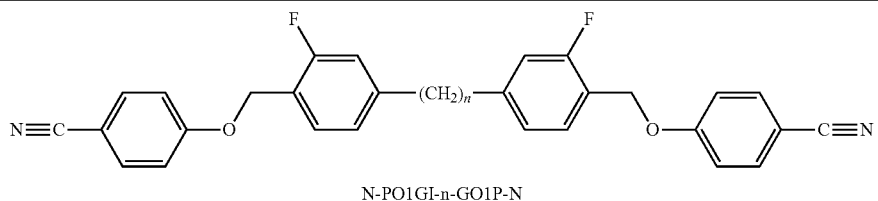
N-PO1GI-n-GO1P-N
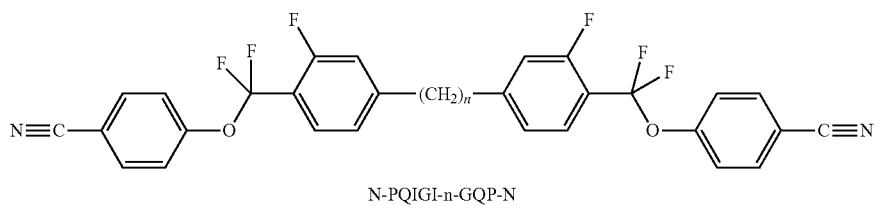
N-PQIGI-n-GQP-N
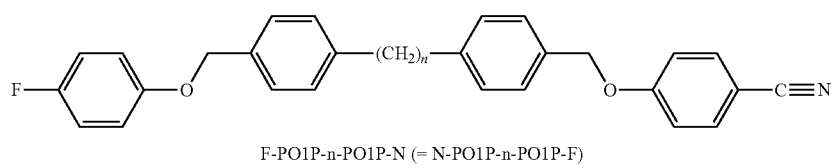
F-PO1P-n-PO1P-N (= N-PO1P-n-PO1P-F)
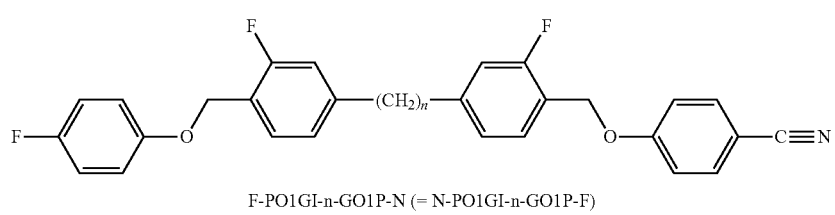
F-PO1GI-n-GO1P-N (= N-PO1GI-n-GO1P-F)
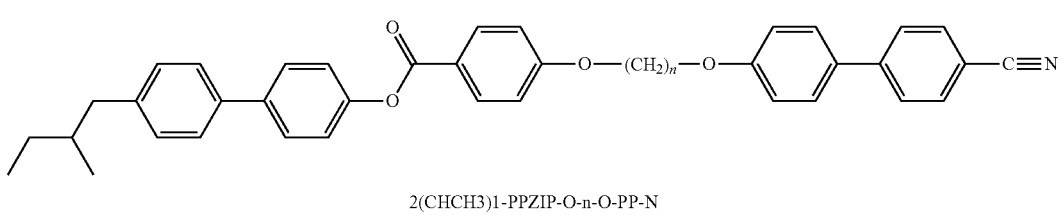
2(CHCH3)1-PPZIP-O-n-O-PP-N
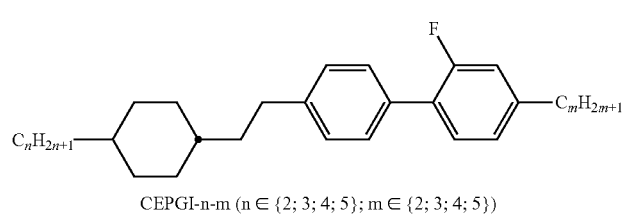
CEPGI-n-m (n ∈ {2; 3; 4; 5}; m ∈ {2; 3; 4; 5})
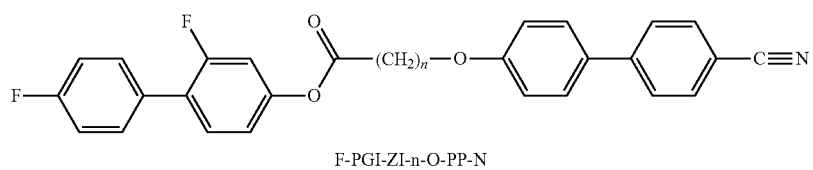
F-PGI-ZI-n-O-PP-N
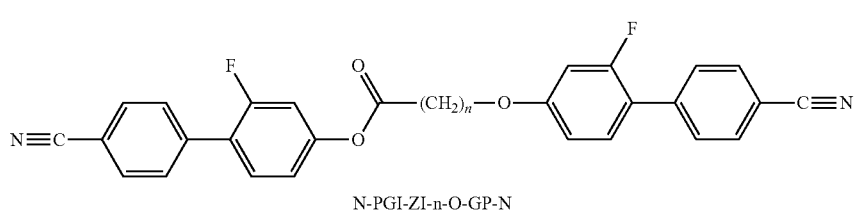
N-PGI-ZI-n-O-GP-N TABLE D-continued
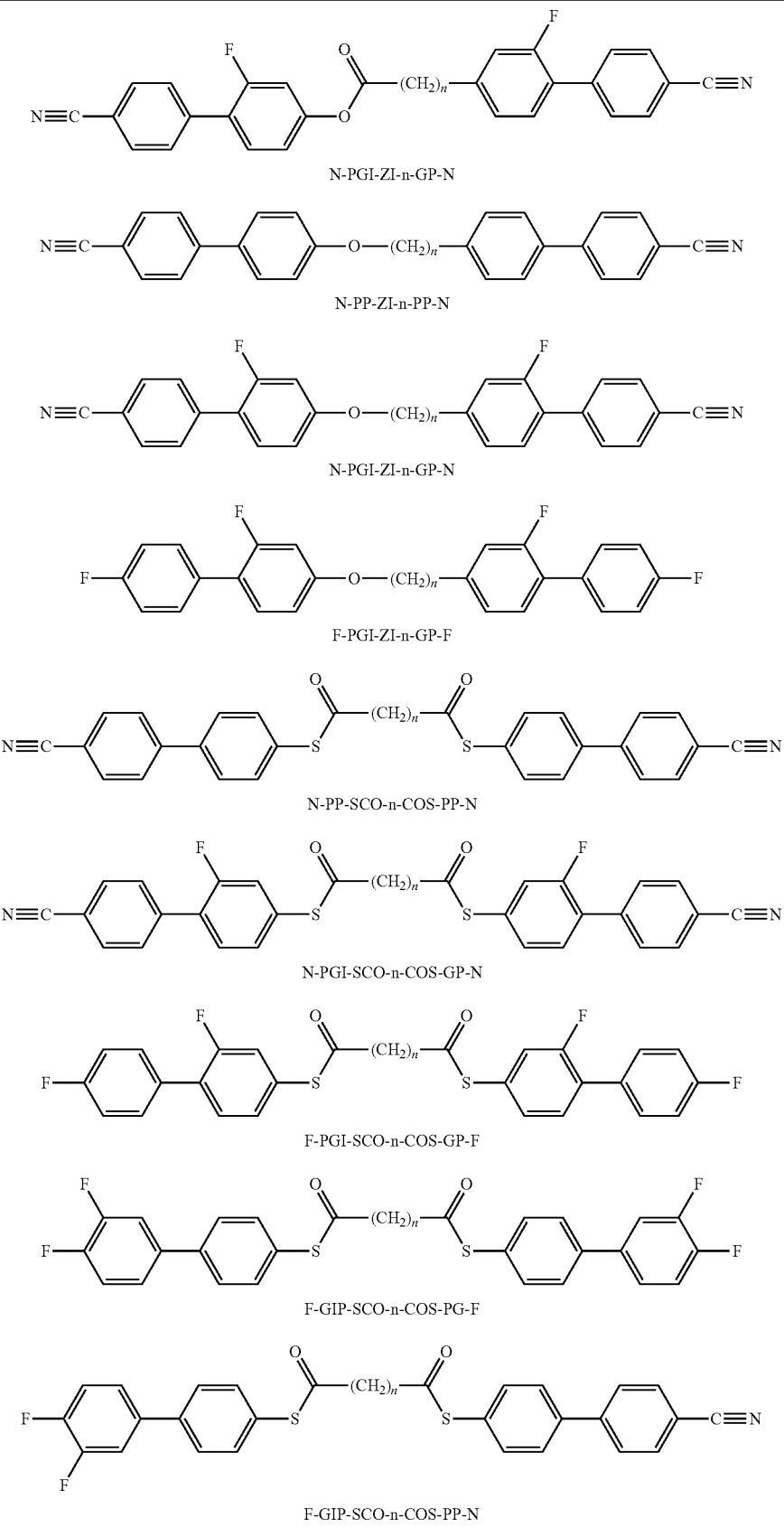

TABLE D-continued
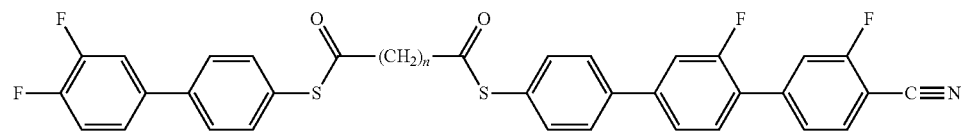
F-GIP-SCO-n-COS-PGG-N
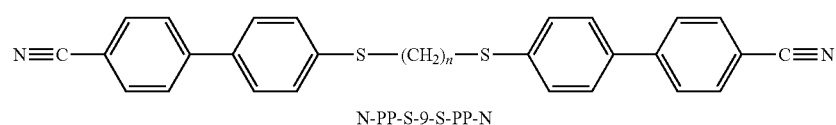
N-PP-S-9-S-PP-N
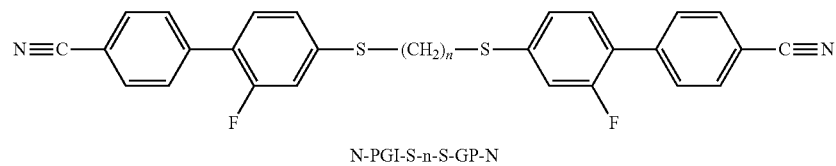
N-PGI-S-n-S-GP-N
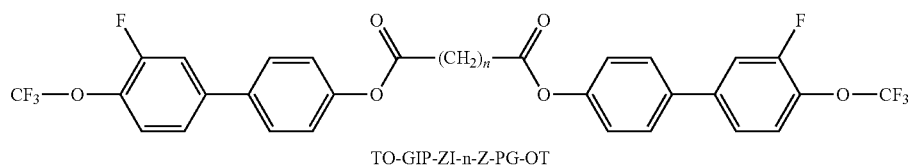
TO-GIP-ZI-n-Z-PG-OT
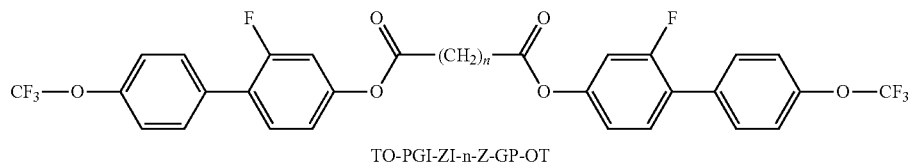
TO-PGI-ZI-n-Z-GP-OT
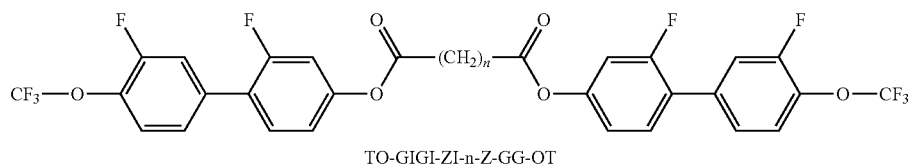
TO-GIGI-ZI-n-Z-GG-OT
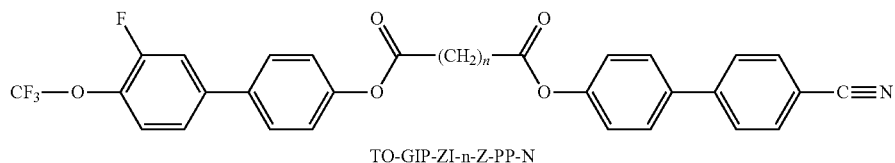
TO-GIP-ZI-n-Z-PP-N
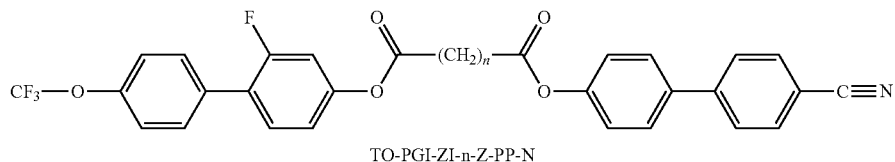
TO-PGI-ZI-n-Z-PP-N
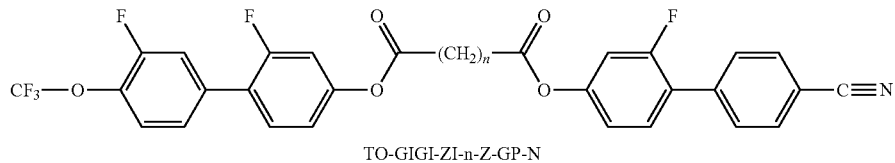
TO-GIGI-ZI-n-Z-GP-N TABLE D-continued
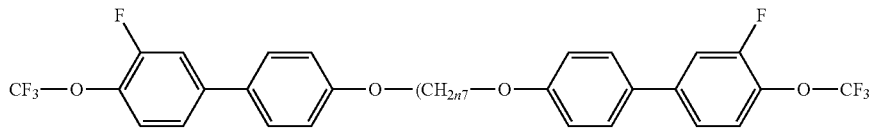
TO-GIP-O-n-O-PG-OT
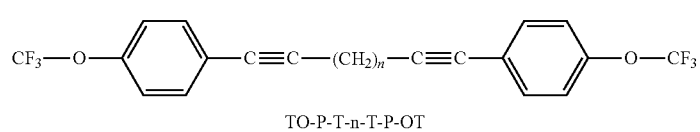
TO-P-T-n-T-P-OT
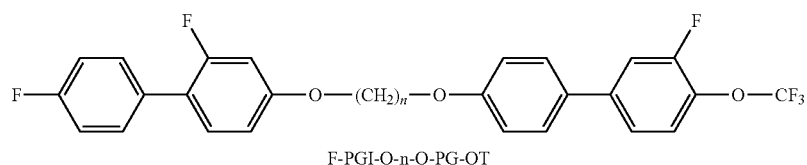
F-PGI-O-n-O-PG-OT
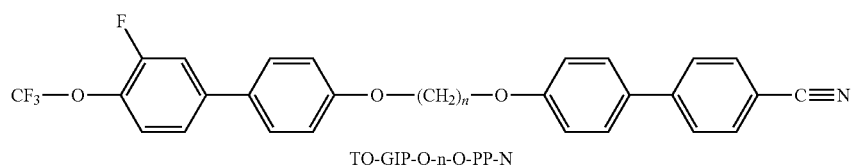
TO-GIP-O-n-O-PP-N
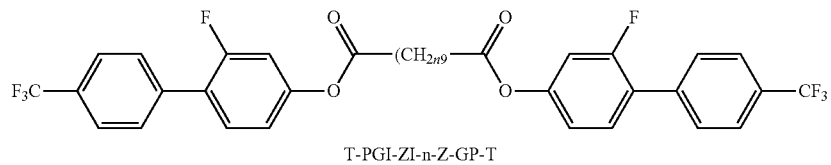
T-PGI-ZI-n-Z-GP-T
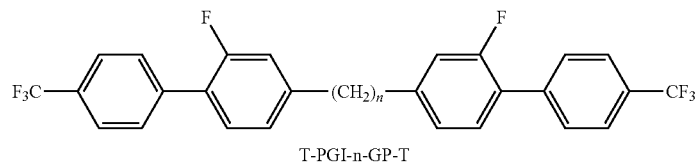
T-PGI-n-GP-T
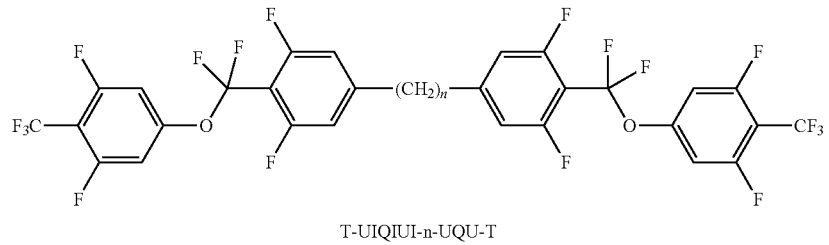
T-UIQIUI-n-UQU-T
In this table n is an integer selected from 3 and 5 to 15, preferably from 3, 5, 7 and 9, unless explicitly defined otherwise.

COMPOUND AND SYNTHESIS EXAMPLES

Synthesis Example 1: Preparation of TO-GIP-ZI-7-Z-PG-OT

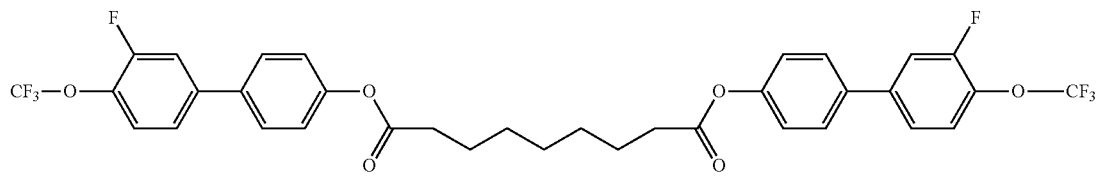

Step 1.1

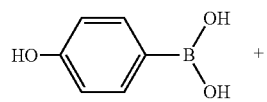

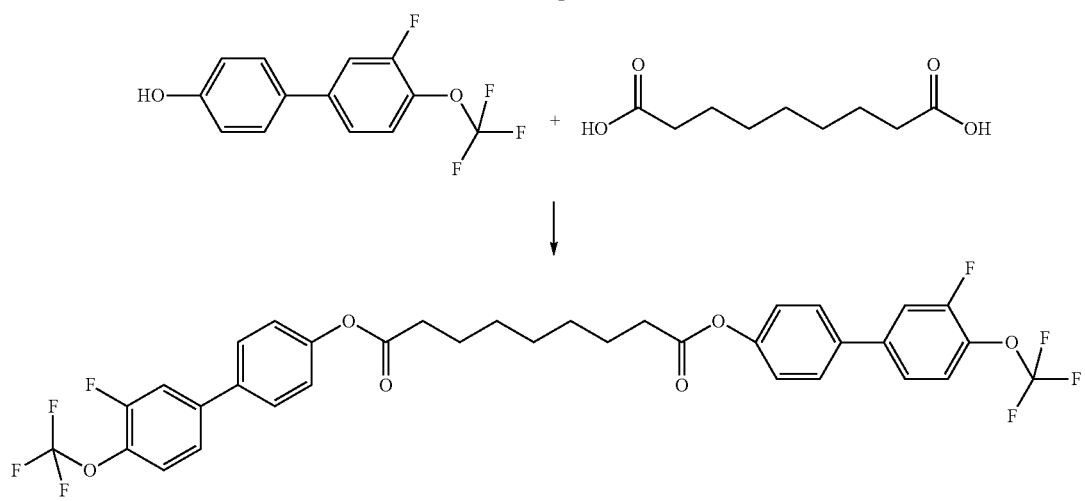

4-bromo-2-fluoro(trifluoromethoxy)benzene (25.0 g, 96.5 mmol) and 4-hydroxy benzeneboronic acid (13.3 g, 96.5 mmol) are added into a flask and dissolved in dioxane (330 ml). The flask is evacuated and filled with nitrogen. A solution of sodium carbonate (21.4 g, 202 mmol) in water (100 ml) is added and the flask is once more evacuated and again filled with nitrogen. [Bis(diphenylphosphino)ferrocene]dichloropalladium(II) (0.71 g, 0.965 mmol) is added as catalyst, before heating the reaction mixture at a temperature of 80° C. for 16 h. After cooling to room temperature, brine (100 ml) and dichloromethane (100 ml) are added and the layers are separated. The reaction mixture is extracted twice more with dichloromethane, the combined organic phases are dried over anhydrous magnesium sulphate. After filtering and removal of the solvent in vacuo, the product is collected as a black solid material. A sample of 5 g is removed for further use in the next synthesis step without further purification.

Step 1.2

Azelaic acid (2.32 g, 12.34 mmol) is added into a flask with dichloromethane (50 ml) and concentrated to dryness to remove traces of water. The resultant solid is re-dissolved with dichloromethane (25 ml) and the flask evacuated and filled with nitrogen. The flask is evacuated again and this time filled with Argon. A solution of dicyclohexylcarbodiimide (5.84 g, 28.3 mmol) in dichloromethane (25 ml) is added to the reaction mixture, followed by a solution of dimethylaminopyridine (3.45 g, 28.3 mmol) in dichloromethane (25 ml). A solution of the phenol from step 1.1 (7.0 g, 25.72 mmol) in dichloromethane (25 ml) is added and the flask is evacuated again and again filled with Argon. The reaction mixture is stirred for two hours before filtering off the precipitates. After washing the filter pad with dichloromethane, the filtrate is concentrated to yield the crude product. The product is purified by column chromatography through silica gel, eluting with a mixture of petroleum ether/dichloromethane (40-60) to yield a white solid. This is re-crystallised from a mixture of petrol (6 volumes), toluene (1 volume) and acetone (4 volumes) to yield the product.

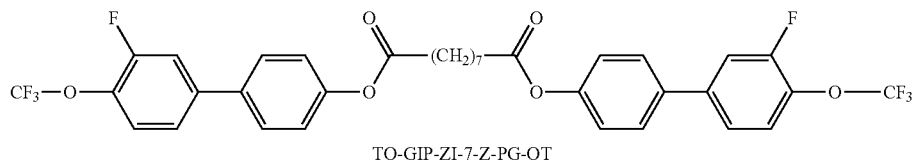

TO-GIP-ZI-7-Z-PG-OT

The product has the following phase range: K 130 I and an e/K of 1.75 Cm$^{-1}$N$^{-1}$. The e/K has been determined for mixture M-1 as specified below.

Synthesis Example 2: Synthesis of TO-CIP-ZI-9-PP—Z—N

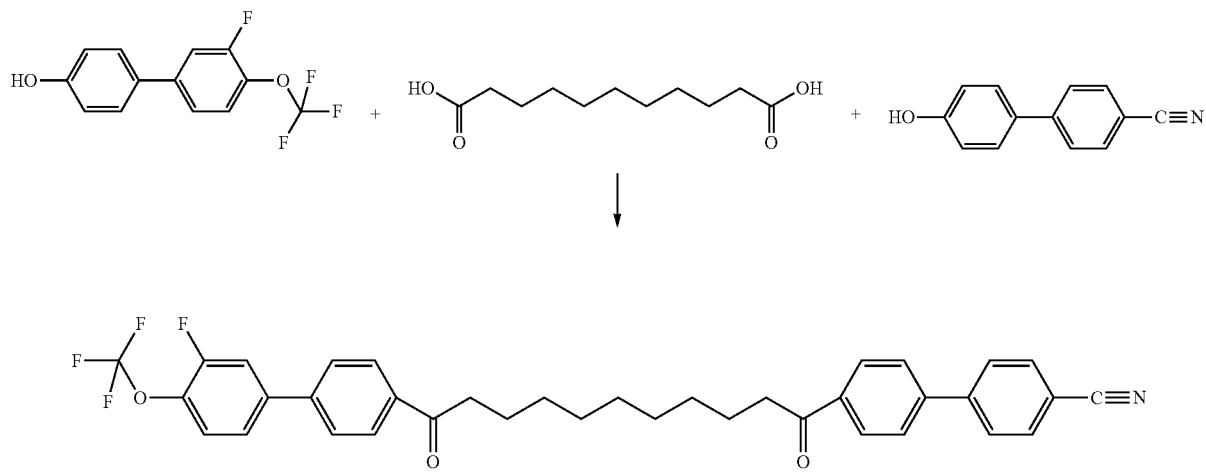

Undecandioic acid (3.24 g, 14.98 mmol), dicyclohexylcarbodiimide (3.09 g, 14.98 mmol) and dimethylaminopyridine (1.83 g, 14.98 mmol) are suspended in dichloromethane (25 ml) and cooled in an ice bath. The reaction mixture is stirred at a temperature of approximately 5° C. before 4'-hydroxybiphenylcarbonitrile (2.9 g, 14.98 mmol) are added over a time of 30 minutes. After the addition is complete, the resultant mixture is brought to ambient temperature and stirred for 16 h. Throughout this application ambient "temperature" is used for a temperature of approximately 22° C. Addition of 4'-hydroxy-3-fluoro-4-(trifluoromethoxy)biphenyl (5.1 g, 15 mmol) from step 1.1 of Example and dicyclohexylcarbodiimide (5.84 g, 28.3 mmol) is carried out before stirring the reaction mixture at room temperature for 16 h. The reaction mixture is then filtered under vacuum and the filter pad is washed with dichloromethane (50 ml). After concentrating the filtrate in vacuo, the crude product (16 g, 165%) is purified by column chromatography through silica gel, eluting with a petroleum ether/dichloromethane mixture (40-60) to yield a white solid. After re-crystallization from a mixture of petrol (6 volumes), toluene (1 volume) and acetone (4 volumes) the product is isolated.

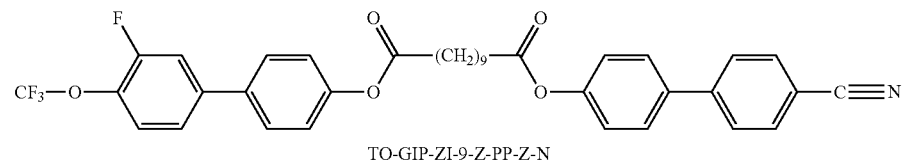

TO-GIP-ZI-9-Z-PP-Z-N

The product has the following phase range: K 109.7 N 114 I.

Synthesis Example 3: Production of T-PGI-ZI-7-Z-GP-T

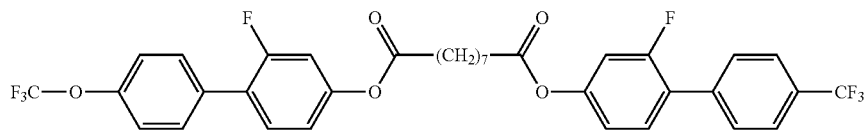

Step 3.1

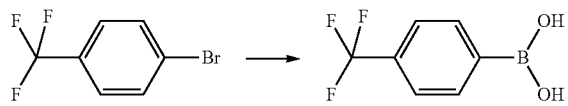 [SMILES: FC(F)(F)c1ccc(Br)cc1 ; OB(O)c1ccc(C(F)(F)F)cc1]

Magnesium turnings (2.97 g, 122 mmol) are added into a flask with tetrahydrofuran (50 ml) and heated under reflux for 10 minutes. The volume of the tetrahydrofuran is reduced via distillation to 20 ml. A crystal of iodine is added to the reaction vessel along with approximately 20 ml of 4-bromo(trifluoromethyl)benzene (25.0 g, 110 mmol) in tetrahydrofuran (150 ml) without stirring. On initiation of the reaction the reaction mixture is stirred and the remainder of the starting bromide solution added dropwise. The reaction mixture is heated under to reflux for 1 hour before being cooled to a temperature of 0° C. A solution of trimethyl borate (13.88 ml, 122 mmol) in tetrahydrofuran (100 ml) is added dropwise at a temperature of 0° C. and the reaction mixture stirred at ambient temperature for 16 h. A solution of hydrochloric acid (27 ml, 278 mmol) in 100 ml water is added and the reaction mixture is stirred for 10 minutes before separating the phases and extracting the aqueous phase with ethyl acetate. The combined organic layers are dried using anhydrous sodium sulphate, filtered and concentrated in vacuo. The crude solid product is purified by column chromatography through silica gel, eluting with a mixture of petroleum ether/dichlormethane It is increased to methanol to elute the product.

Step 3.2

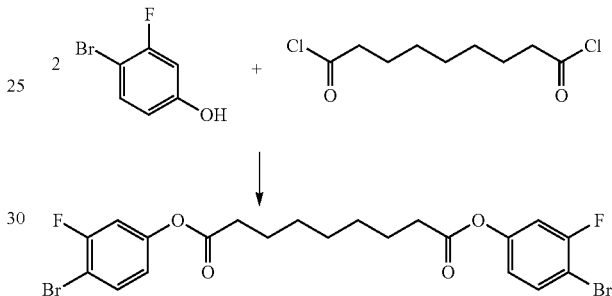

3-Fluoro-4-bromophenol (21.2 g, 0.11 mol) is added into a flask with azelaic acid chloride (25.0 g, 0.11 mol) and dichloromethane (465 g). The mixture is cooled to a temperature of 0° C. before triethylamine (38.1 ml, 275 mmol) is added dropwise, keeping the temperature below 5° C. at all times. After the addition, the reaction mixture is stirred over night at 35° C. before being cooled to room temperature. The mixture is poured onto ice and the resulting phases are separated. The aqueous phase is extracted with dichloromethane three times and the combined organic phases are washed with water until the pH is neutral. The organic solution is dried over anhydrous sodium sulphate, filtered and concentrated in vacuo to yield the crude product. The material is purified by column chromatography through silica gel, eluting with a mixture of petroleum ether/dichloromethane (40-60) to yield a white solid.

Step 3.3

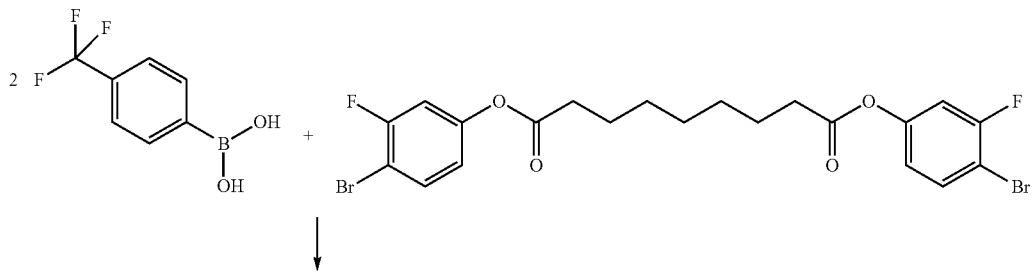

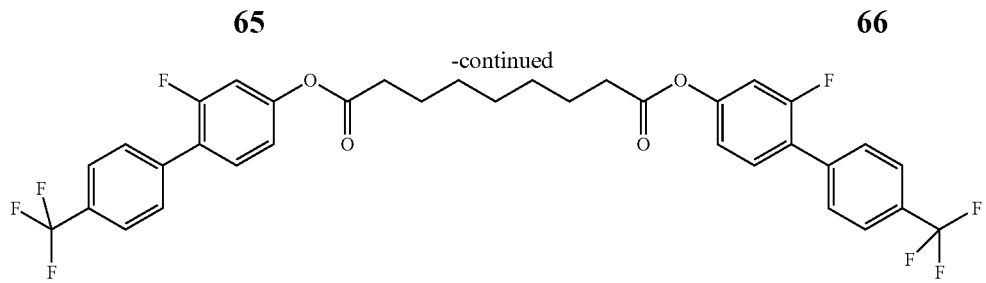

The Intermediates from step 3.1 (7.87 g, 41 mmol) and from step 3.2 (11.06 g, 21 mmol) are added into a reaction flask with tetrahydrofuran (300 ml). A solution of sodium metaborate octahydrate (17.9 g, 64.9 mmol) in water (70 ml) is added. Then the flask is evacuated three times and subsequently filled with nitrogen each time, then treated in an ultrasonic bath to degas the reaction mixture, a procedure, which is shortly referred to as "ultrasonication" in this application, for 10 min. Bis(triphenylphosphine) palladium (II) dichloride (1.22 g, 2 mmol) is added and the reaction mixture is heating to 80° C. for 16 h. After cooling to room temperature water (100 ml) is added and the resulting phases are separated. The aqueous phase is extracted with ethyl acetate three times and the combined organic phases are washed with water. The organic solution is dried over anhydrous sodium sulphate, filtered and concentrated in vacuo to yield the crude product, which is purified by column chromatography through silica gel. Subsequent re-crystallizations from petroleum ether and three re-crystallizations from acetonitrile lead to the pure product.

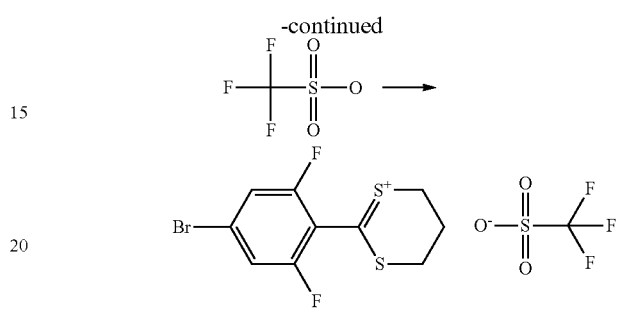

4-bromo-2,5-difluorobenzoic acid (50 g, 207 mmol) is added to a flask with toluene (40 ml) and isooctane (50 ml). Propandithiol (29.3 g, 500 mmol) is added to the flask before stirring the suspension and heating to a temperature of 60° C. Trifluoromethanesulphonic acid (50 g, 325 mmol) is added and the mixture is heated to a temperature of 120° C.

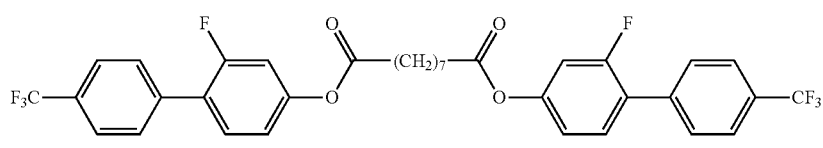

T-PGI-ZI-7-Z-GP-T

The product has the following phase range: K 106.2 I and an e/K of 1.68 Cm$^{-1}$N$^{-1}$.

Synthesis Example 4: Production of T-UIQIUI-9-UQU-T before the then clear orange mixture is cooled to ambient temperature. Then it is treated with diethyl ether (120 ml). This solution is added to a flask of vigorously stirred methyl tert-butyl ether (250 ml) and pre-cooled to a temperature of 0° C. Within 30 minutes fine crystals appear in the stirred mixture. The solid is isolated by filtration under vacuum and washed with ether to give a pale yellow powder which is used immediately in the next step.

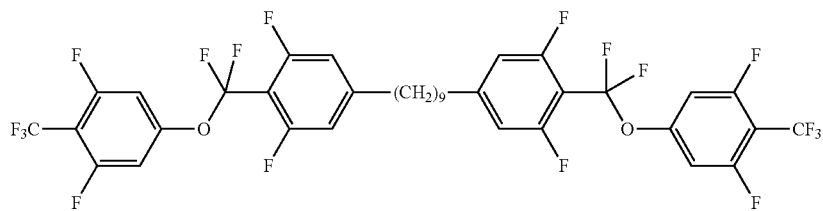

Step 4.1

Step 4.2

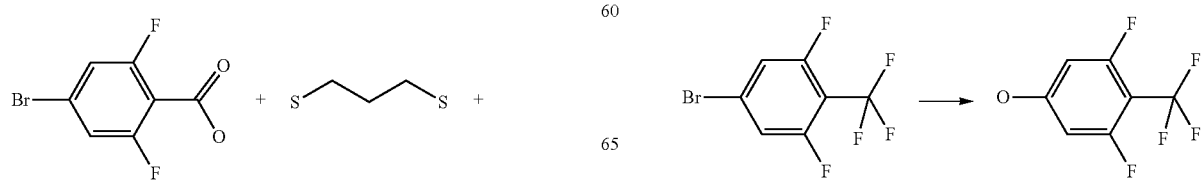

4-bromo-2,5-difluoro-(trifluoromethyl)benzene (142 g, 0.083 mol) is added to a flask with diethyl ether (420 ml). After cooling the reaction mixture to a temperature of −70° C., n-BuLi (365 ml, 0.131 mol) is slowly added over a time span of 30 minutes and the reaction mixture stirred further for another 2 h at −70° C. The reaction mixture is allowed to warm to ambient temperature and stirred for a further 24 h. Acetic acid (62 ml, 0.131 mol) is added and the reaction mixture is stirred before 35% hydrogen peroxide (140 ml, 0.20 mol) is added slowly keeping the temperature always below 35° C. After stirring for 5 h, the reaction mixture is acidified with hydrochloric acid before separating the layers. The aqueous phase is extracted twice with methyl tert-butyl ether and the combined organic phases are washed with ammonium sulphate solution and then with water until the pH is neutral. The product is dried over sodium sulphate, filtered and concentrated in vacuo. The crude product is purified by column chromatography over silica gel, eluting with dichloromethane.

Step 4.3

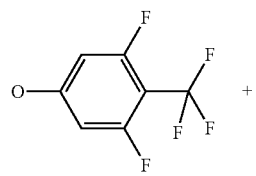

-continued

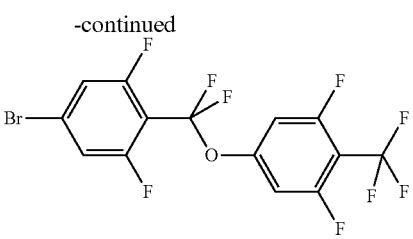

The intermediate product from step 4.1 (25.6 g, 51 mmol) is added to a flask with dichloromethane (250 ml) and then cooled to a temperature of −70° C. A mixture of the intermediate product from step 4.2 (8 g, 40.5 mmol), dichloromethane (40 ml) and triethylamine (45.2 ml, 240 mmol) is added dropwise, keeping the temperature always below −65° C. After 30 minutes further stirring triethylaminehydrogen fluoride (45 ml, 140 mmol) is added dropwise. After stirring for a further hour bromine (14.5 ml, 240 mmol) in dichloromethane (60 ml) is added dropwise. The reaction mixture is stirre for 60 minutes at −70° C. and then warmed to ambient temperature before stirring for a further 2 h. The reaction mixture then is carefully poured into a solution of sodium hydroxide (100 ml, 0.8 mol) in iced water (500 ml) and the phases are separated. The organic phase is washed with water, dried over sodium sulphate and concentrated in vacuo. The crude product is purified by flash chromatography, eluting with a solution of 20% methyl tert-butylether in petroleum ether. Final purification is carried out by re-crystallization from petroleum ether at a temperature of −20° C. to yield the desired product.

Step 4.4

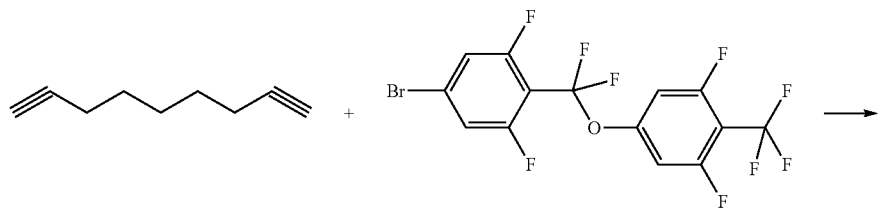

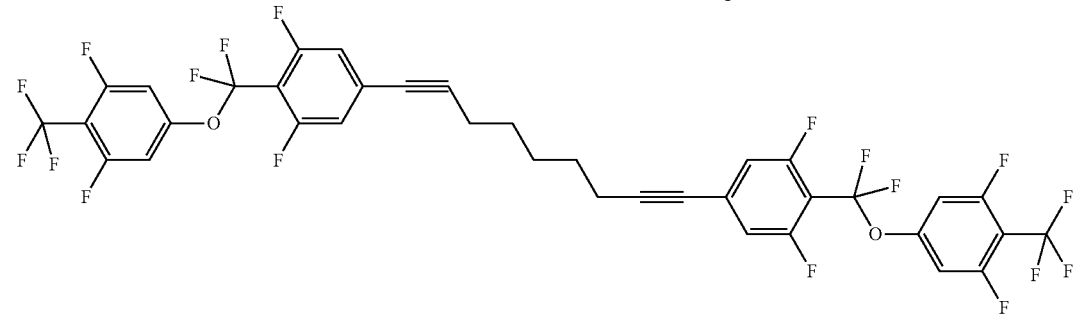

-continued

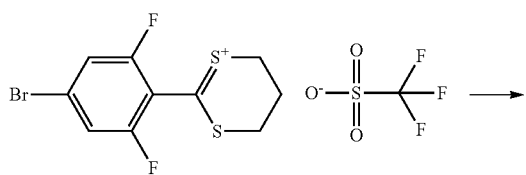

The bromide from step 2 (11.9 g, 27 mmol) is added to a flask together with triethylamine (40 ml, 0.39 mol), tetrahydrofuran (40 ml, 1.1 mol) and bis(triphenylphosphine)palladium(II) chloride (0.10 g, 0.15 mmol). The reaction mixture is heated to a temperature of 40° C., then 1,8-nonadiyne (1.62 g, 13.5 mmol) as a solution in tetrahydrofuran (40 ml, 1.1 mol) is added over a time span of 30 minutes. The reaction mixture is heated for a further 72 h at a temperature of 40° C. before it is heated to a temperature of 60° C. for 16 h to complete conversion. The reaction mixture is then cooled to ambient temperature and filtered under vacuum. The filter pad is washed with dichloromethane and the organic phase is concentrated under vacuum.

The crude product is purified by column chromatography through silica gel, eluting with dichloromethane. Final purification is carried out by two re-crystallizations from petroleum ether. The product is obtained as a white solid.

Step 4.5

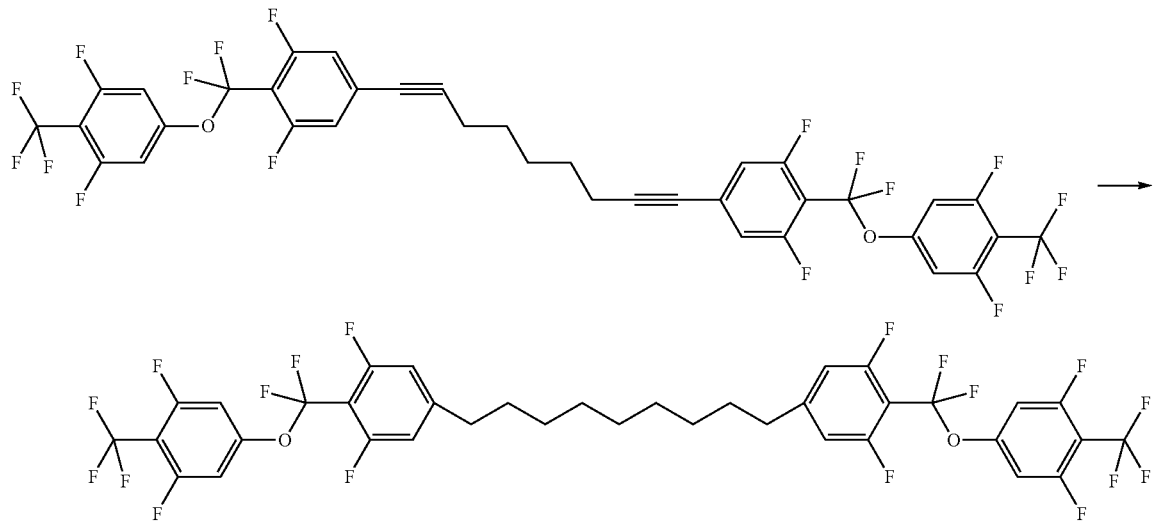

The intermediate product from step 4.4 (5.80 g, 6.93 mmol) is dissolved in tetrahydrofurane (150 ml) and passed through the H-Cube hydrogenator. The catalyst used is palladium/carbon (5%). The pressure is increased until the reaction is to completed. The resultant solution is concentrated under reduced pressure yielding a solid product, which is purified by column chromatography through silica gel, eluting with ethyl acetate/petrol (1:9). The fractions high in product concentration are combined and re-crystallized from acetonitrile to give a white solid product.

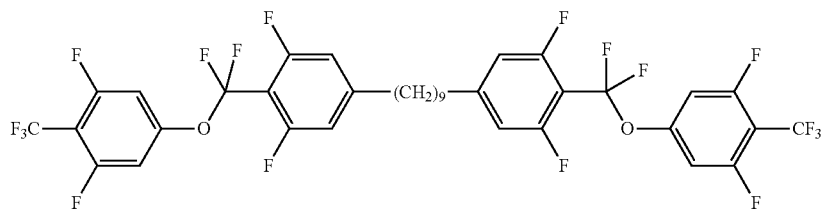

Phase sequence: K 51.4 I.

Compound Examples 5 and Following

The following compounds of formula I are prepared analogously.

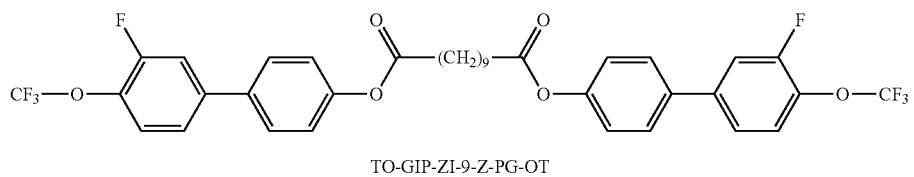

TO-GIP-ZI-9-Z-PG-OT

Phase Sequence: K 124.5 I; e/K=1.93 Cm$^{-1}$N$^{-1}$.

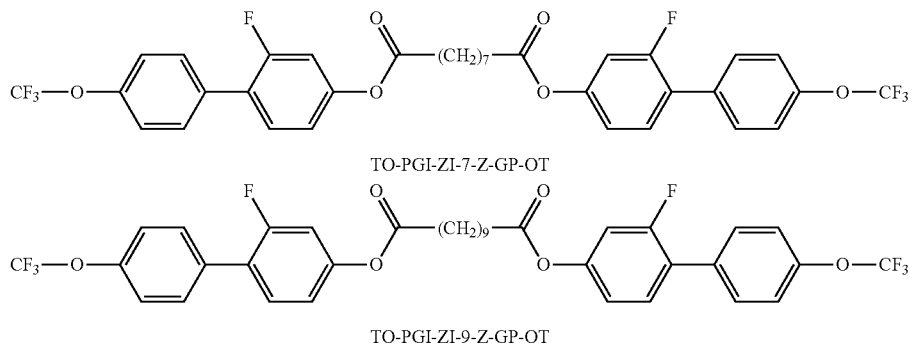
Phase Sequence: K (80 SmA) 84 l; e/K=2.0 Cm$^{-1}$N$^{-1}$.
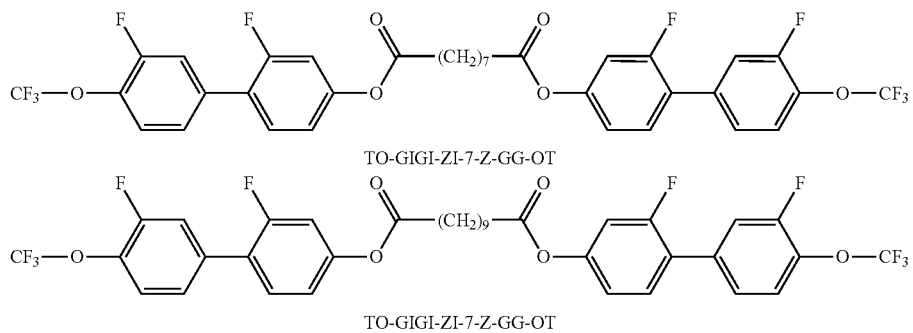
Phase Sequence: K 106 l.
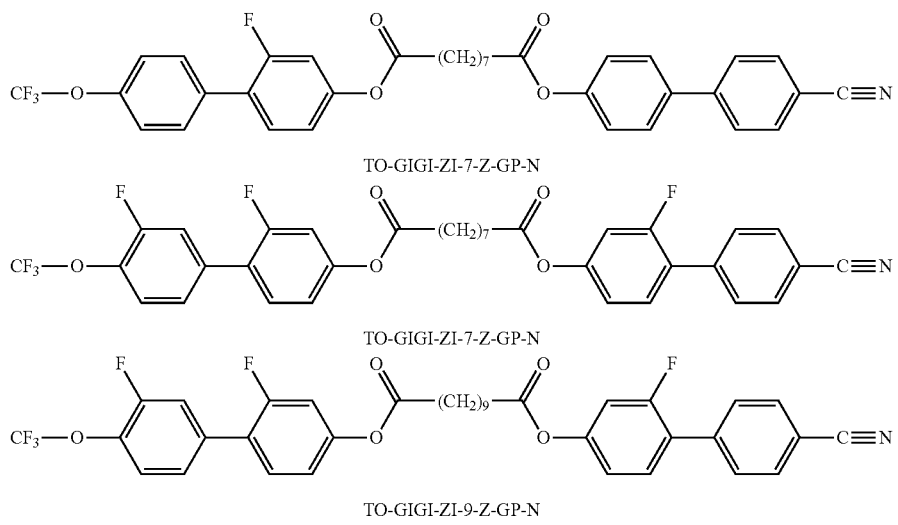
Phase Sequence: K 72 N 82 l; e/K=2.01 Cm$^{-1}$N$^{-1}$.
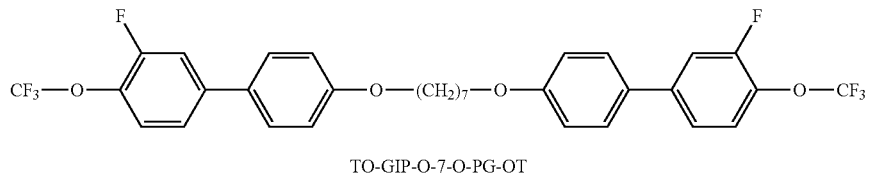
Phase Sequence: K 96 l.

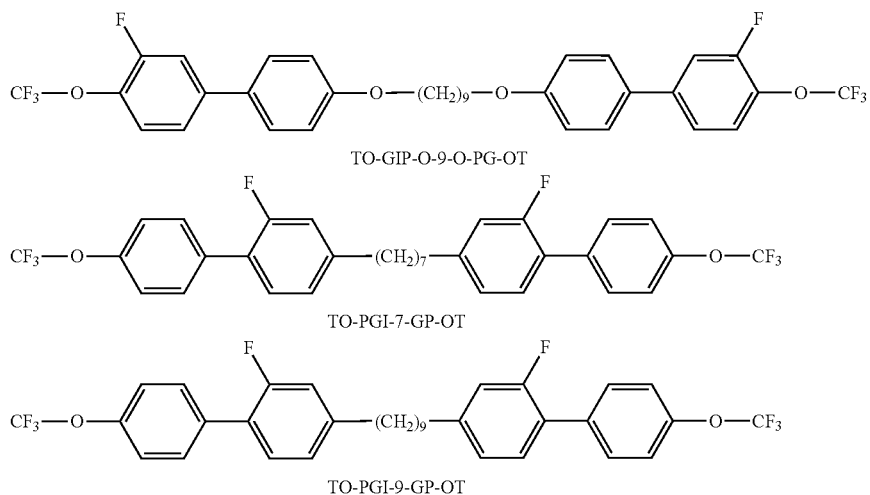
Phase Sequence: K 32.3 I; e/K=1.87 Cm$^{-1}$N$^{-1}$.
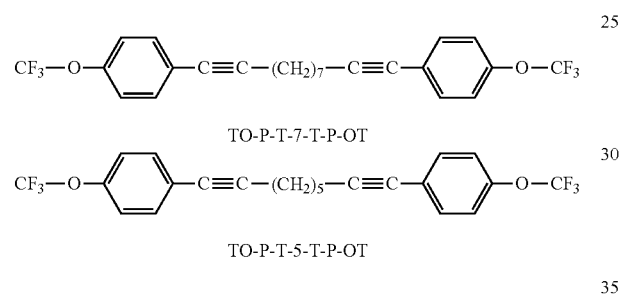
Phase Sequence: K 0.0 I.
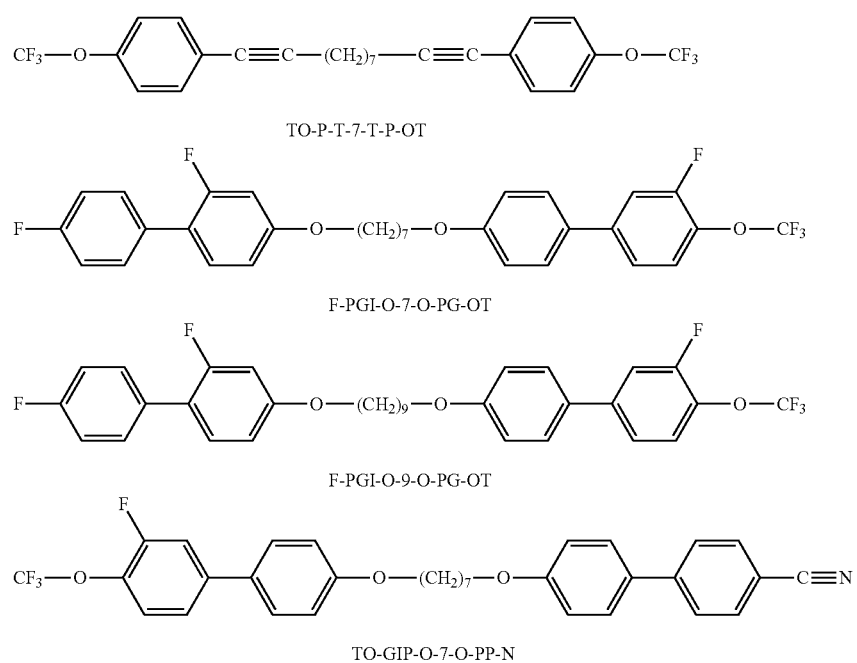
Phase Sequence: K 78 N 101 I.

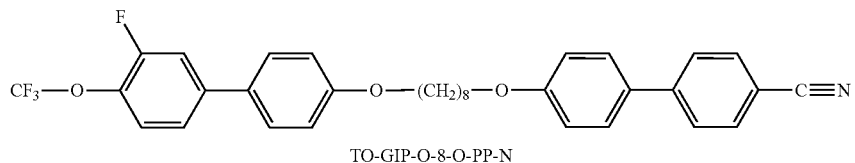
TO-GIP-O-8-O-PP-N
Phase Sequence: K 89.1 I.
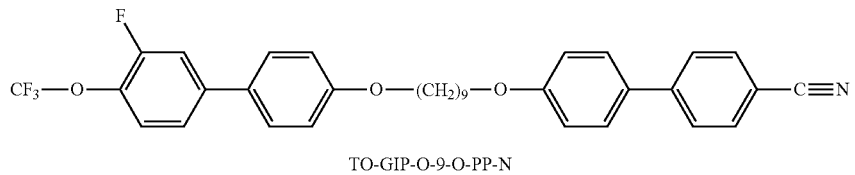
TO-GIP-O-9-O-PP-N
Phase Sequence: K 81 N 103 I.
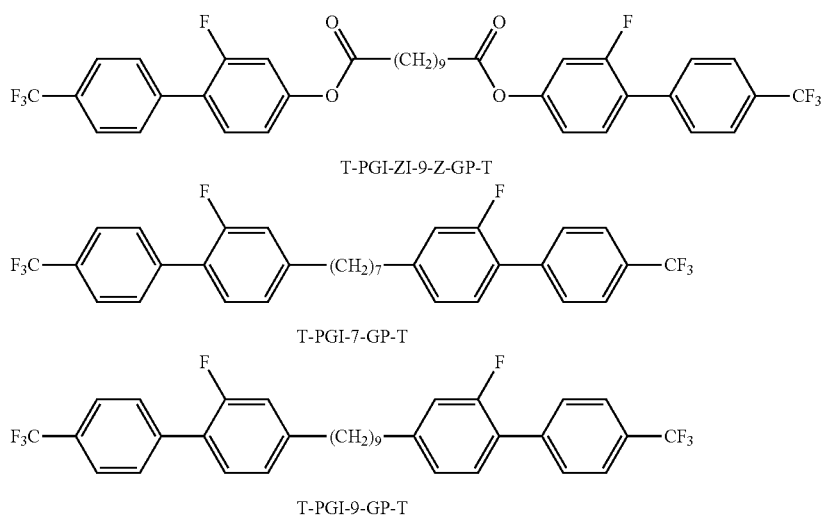
T-PGI-ZI-9-Z-GP-T
T-PGI-7-GP-T
T-PGI-9-GP-T
Phase Sequence: K 50.3 I; e/K=1.68 Cm$^{-1}$N$^{-1}$.
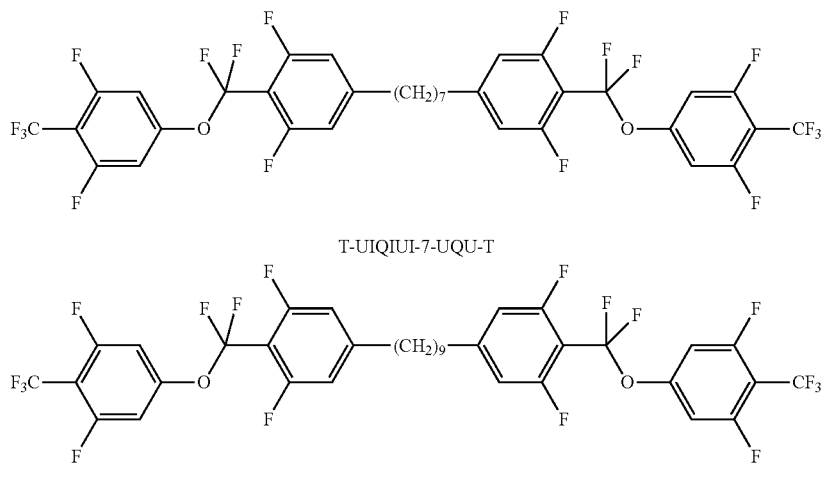
T-UIQIUI-7-UQU-T
T-UIQIUI-9-UQU-T
Phase Sequence: K 51.4 I.

The materials in the above table generally showed increased performance in the screening mixtures, as compared to known, more conventional bimesogenic compounds as e.g. those shown in the table below.

Comparative Compound Examples

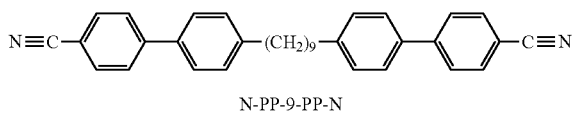

N-PP-9-PP-N

Phase Sequence: K 84.1 SmC 105.7 N 122 I.

N-PGI-9-GP-N

Phase Sequence: K 97.7 (N 82.5) I.

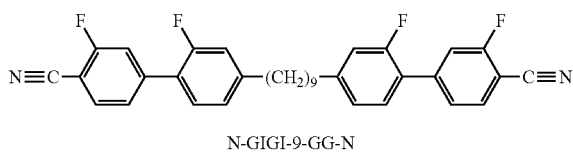

N-GIGI-9-GG-N

Phase Sequence: K 86.3 I.

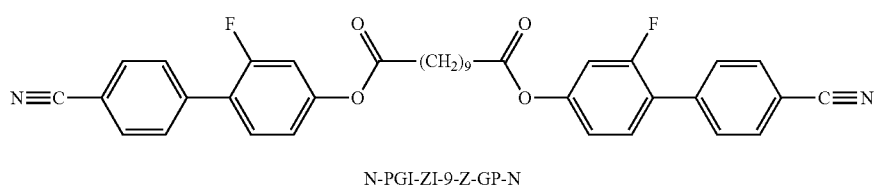

N-PGI-ZI-9-Z-GP-N

Phase Sequence: K 128.5 N 138.7 I.

Use Examples, Mixture Examples

Typically a 5.6 μm thick cell, having an anti-parallel rubbed PI alignment layer, is filled on a hotplate at a temperature at which the flexoelectric mixture in the isotropic phase.

After the cell has been filled phase transitions, including clearing point, are measured using Differential Scanning calorimetry (DSC) and verified by optical inspection. For optical phase transition measurements, a Mettler FP90 hot-stage controller connected to a FP82 hot-stage is used to control the temperature of the cell. The temperature is increased from ambient temperature at a rate of 5 degrees C. per minute, until the onset of the isotropic phase is observed. The texture change is observed through crossed polarizers using an Olympus BX51 microscope and the respective temperature noted.

Wires are then attached to the ITO electrodes of the cell using indium metal. The cell is secured in a Linkam THMS600 hot-stage connected to a Linkam TMS93 hot-stage controller. The hot-stage is secured to a rotation stage in an Olympus BX51 microscope.

The cell is heated until the liquid crystal is completely isotropic. The cell is then cooled under an applied electric field until the sample is completely nematic. The driving waveform is supplied by a Tektronix AFG3021B arbitrary function generator, which is sent through a Newtons 4th LPA400 power amplifier before being applied to the cell. The cell response is monitored with a Thorlabs PDA55 photodiode. Both input waveforms and optical response are measured using a Tektronix TDS 2024B digital oscilloscope.

In order to measure the flexoelastic response of the material, the change in the size of the tilt of the optic axis is measured as a function of increasing voltage. This is achieved by using the equation:

$$\tan\varphi = \frac{P_0}{2\pi}\frac{e}{K}E$$

wherein φ is the tilt in the optic axis from the original position (i.e. when E=0), E is the applied field, K is the elastic constant (average of $K_1$ and $K_3$) and e is the flexoelectric coefficient (where $e=e_1+e_3$). The applied field is monitored using a HP 34401A multimeter. The tilt angle is measured using the aforementioned microscope and oscilloscope. The undisturbed cholesteric pitch, $P_0$, is measured using an Ocean Optics USB4000 spectrometer attached to a computer. The selective reflection band is obtained and pitch determined from the spectral data.

The mixtures shown in the following examples are well suitable for use in USH-displays. To that end an appropriate concentration of the chiral dopant or dopants used has to be applied in order to achieve a cholesteric pitch of 200 nm or less.

Comparative Mixture Example 1

Host Mixture H-0

The host mixture H-0 is prepared and investigated.

| No. | Composition Compound Abbreviation | Conc./% |
|---|---|---|
| 1 | F-PGI-O-9-O-GP-F | 25.0 |
| 2 | F-PGI-O-9-O-PP-N | 25.0 |
| 3 | F-PGI-ZI-9-Z-GP-F | 25.0 |
| 4 | F-PGI-ZI-9-Z-PP-N | 25.0 |
| Σ | | 100.0 |

2% of the chiral dopant R-5011 are added to the mixture H-0 leading to the mixture H-1, which is investigated for its properties.

| Composition Compound | | |
|---|---|---|
| No. | Abbreviation | Conc./% |
| 1 | R-5011 | 2.0 |
| 2 | F-PGI-O-9-O-GP-F | 24.5 |
| 3 | F-PGI-O-9-O-PP-N | 24.5 |
| 4 | F-PGI-ZI-9-Z-GP-F | 24.5 |
| 5 | F-PGI-ZI-9-Z-PP-N | 24.5 |
| Σ | | 100.0 |

The mixture H-1 may be used for the ULH-mode. It has a clearing point of 82° C. and a lower transition temperature of 33° C. It has a cholesteric pitch of 291 nm at 25° C. The e/K of this mixture is 1.80 $Cm^{-1}N^{-1}$ at a temperature of 0.9T(N,I).

Mixture Examples 1.1 to 1.4

2% of the chiral dopant R-5011 and 10% of the compound of synthesis example 1 are added to the mixture H-0 leading to the mixture M-1.1, which is investigated for its properties.

| Composition Compound | | |
|---|---|---|
| No. | Abbreviation | Conc./% |
| 1 | R-5011 | 2.0 |
| 2 | F-PGI-O-9-O-GP-F | 22.0 |
| 3 | F-PGI-O-9-O-PP-N | 22.0 |
| 4 | F-PGI-ZI-9-Z-GP-F | 22.0 |
| 5 | F-PGI-ZI-9-Z-PP-N | 22.0 |
| 6 | TO-GIP-ZI-7-Z-PG-OT | 10.0 |
| Σ | | 100.0 |

This mixture (M-1.1) is well suitable for the ULH-mode. It has a clearing point of 87° C. and a lower transition temperature of 28.5° C. It has a cholesteric pitch of 291 nm at a temperature of 0.9T(N,I). The e/K of this mixture is 1.75 $Cm^{-1}N^{-1}$ at a temperature of 0.9T(N,I).

The investigation described above is performed with 10% each of several compounds of formula I instead of that of synthesis example 1 used in host mixture H-0, together with 2% R-5011. The results are shown in the following table.

| Ex. | Mixture | Compound | T(N,I)/ °C. | $T_{low}$/ °C. | P/ nm | e/K/ $V^{-1}$ |
|---|---|---|---|---|---|---|
| C1.1 | H-1.0 | None | 82 | 33 | 291 | 1.80 |
| C1.2 | H-1.1 | N-PP-9-PP-N | t.b.d. | 42 | t.b.d. | t.b.d. |
| C1.3 | H-1.2 | F-PGI-O-7-O-GP-F | 108 | 26.5 | 332 | 1.70 |
| E1.1 | M-1.1 | TO-GIP-ZI-7-Z-PG-OT | 87 | 28.5 | 291 | 1.75 |
| E1.2 | M.1.2 | TO-GIP-ZI-9-Z-PG-OT | 78.2 | t.b.d. | 272 | 1.95 |
| E1.3 | M-1.3 | TO-PGI-ZI-9-Z-GP-OT | 80 | 28 | 292 | 2.00 |
| E1.4 | M-1.4 | TO-PGI-9-GP-OT | 70 | 30 | 300 | 2.27 |

Remarks: t.b.d.: to be determined
the cholesteric pitch (P) is given at 0.9T(N,I) and e/K is given $V^{-1}$ (i.e. $Cm^{-1}N^{-1}$) at 0.9T(N,I).

Comparative Mixture Example 1.2: Mixture H-1.1

The following mixture (Mixture H-1.1) is prepared and investigated.

| Composition Compound | | |
|---|---|---|
| No. | Abbreviation | Conc./% |
| 1 | R-5011 | 2.0 |
| 2 | F-PGI-O-9-O-GP-F | 22.0 |
| 3 | F-PGI-O-9-O-PP-N | 22.0 |
| 4 | F-PGI-ZI-9-Z-GP-F | 22.0 |
| 5 | F-PGI-ZI-9-Z-PP-N | 22.0 |
| 6 | N-PP-9-PP-N | 10.0 |
| Σ | | 100.0 |

This mixture, mixture H-1.1, shows an N to N2 transition at 42° C.

Comparative Mixture Example 1.3: Mixture H-1.2

The following mixture is prepared (Mixture H-1.2) and investigated.

| Composition Compound | | |
|---|---|---|
| No. | Abbreviation | Conc./% |
| 1 | R-5011 | 2.0 |
| 2 | F-PGI-O-9-O-GP-F | 22.0 |
| 3 | F-PGI-O-9-O-PP-N | 22.0 |
| 4 | F-PGI-ZI-9-Z-GP-F | 22.0 |
| 5 | F-PGI-ZI-9-Z-PP-N | 22.0 |
| 6 | F-PGI-O-7-O-GP-F | 10.0 |
| Σ | | 100.0 |

This mixture, mixture C-1.2, has a clearing point of 108° C. and shows an to N2 transition at 26.5° C. It has a cholesteric pitch of 332 nm at 0.9T(N,I). The e/K of this mixture is 1.70 $Cm^{-1}N^{-1}$ at 0.9T(N,I), i.e. at a temperature of 70° C.

Mixture Example 2: Mixture M-2

The following mixture (Mixture M-2) is prepared and investigated.

| Composition Compound | | |
|---|---|---|
| No. | Abbreviation | Conc./% |
| 1 | R-5011 | 2.0 |
| 2 | N-PGI-ZI-7-Z-GP-N | 2.8 |
| 3 | N-PGI-ZI-9-Z-GP-N | 9.2 |
| 4 | F-PGI-ZI-7-Z-PP-N | 13.5 |
| 5 | F-PGI-ZI-9-Z-PUU-N | 7.5 |
| 6 | N-GIGI-9-GG-N | 16.4 |
| 7 | N-PUI-9-UP-N | 1.8 |
| 8 | N-UIUI-9-UU-N | 20.0 |
| 9 | TO-PGI-ZI-9-Z-GP-OT | 11.4 |
| 10 | CEPGI-3-2 | 7.5 |
| 11 | CEPGI-5-2 | 7.5 |
| Σ | | 100.0 |

This mixture, mixture M-2, has a transition from the crystalline phase to the second nematic phase [T(C,N2)] at 20° C. and a clearing point [T(N,I)] at 61° C. This mixture (M-2) is well suitable for the ULH-mode. It has a cholesteric pitch of 302 nm at 35° C. The e/K of this mixture is 3.86 $Cm^{-1}N^{-1}$ at a temperature of 35° C.

TABLE

Response times of Mixture M-2

| $U_{rms}/V$ | $E/V/\mu m$ | $\tau_{on}/ms$ | $\tau_{off}/ms$ |
|---|---|---|---|
| 5.0 | 0.89 | t.b.d. | t.b.d. |
| 7.0 | 1.25 | 2.19 | 3.14 |
| 9.0 | 1.60 | 1.95 | 3.02 |
| 15.0 | 2.67 | 1.04 | 3.20 |

Mixture Example 3: Mixture M-3

The following mixture (Mixture M-3), which, besides the chiral dopant, consists entirely of compounds of formula I according to the present application, is prepared and investigated.

| No. | Composition Compound Abbreviation | Conc./% |
|---|---|---|
| 1 | R-5011 | 1.8 |
| 2 | TO-PGI-ZI-9-Z-GP-OT | 24.2 |
| 3 | TO-GIP-ZI-9-Z-PG-OT | 5.1 |
| 4 | TO-PGI-9-GP-OT | 10.2 |
| 5 | TO-PGI-ZI-9-Z-PP-N | 8.6 |
| 6 | TO-GIGI-ZI-9-Z-GP-N | 29.9 |
| 7 | TO-GIP-O-9-O-PP-N | 20.2 |
| Σ | | 100.0 |

This mixture, mixture M-3, is very well suitable for the ULH-mode. In particular the response times of this mixture are excellent and it has a relatively broad temperature range for the liquid crystalline phase.

It has a clearing point of 68° C. and a transition from the second nematic phase to the nematic phase [T(N2,N)] at 23.5° C. It has a cholesteric pitch of 275 nm at 35° C. The e/K of this mixture is 2.5 $Cm^{-1}N^{-1}$ at a temperature of 35° C.

TABLE

Response times of Mixture M-3

| $U_{rms}/V$ | $E/V/\mu m$ | $\tau_{on}/ms$ | $\tau_{off}/ms$ |
|---|---|---|---|
| 5.0 | 0.88 | 1.78 | 1.95 |
| 9.0 | 1.58 | 1.77 | 1.96 |
| 15.0 | 2.64 | 1.50 | 2.03 |

Mixture Example 4: Mixture M-4

The following mixture (Mixture M-4) is prepared and investigated.

| No. | Composition Compound Abbreviation | Conc./% |
|---|---|---|
| 1 | R-5011 | 2.0 |
| 2 | F-PGI-ZI-9-Z-GP-F | 20.0 |
| 3 | F-PGI-ZI-7-Z-PP-N | 30.0 |
| 4 | F-PGI-ZI-9-Z-PP-N | 6.0 |
| 5 | F-PGI-ZI-9-Z-PUU-N | 17.0 |
| 6 | TO-PGI-ZI-9-Z-GP-OT | 25.0 |
| Σ | | 100.0 |

This mixture, mixture M-4, is very well suitable for the ULH-mode. In particular the response times of this mixture are excellent and it has a relatively broad temperature range for the liquid crystalline phase.

It has a clearing point [T(N,I)] of 90° C. and a a transition from the second nematic phase to the nematic phase [T(N2,N)] at 25° C. It has a cholesteric pitch of 300 nm at 35° C. The e/K of this mixture is 2.8 $Cm^{-1}N^{-1}$ at a temperature of 35° C.

Mixture Example 5: Mixture M-5

The following mixture (Mixture M-5) is prepared and investigated.

| No. | Composition Compound Abbreviation | Conc./% |
|---|---|---|
| 1 | R-5011 | 2.0 |
| 2 | F-PGI-ZI-7-Z-PP-N | 19.4 |
| 3 | F-PGI-ZI-9-Z-PP-N | 11.1 |
| 4 | F-PGI-ZI-9-Z-PU-N | 12.0 |
| 5 | F-UIGI-ZI-9-Z-GP-N | 17.2 |
| 6 | TO-GIP-ZI-9-Z-PP-N | 5.7 |
| 7 | TO-GIGI-ZI-9-Z-GP-N | 32.6 |
| Σ | | 100.0 |

This mixture, mixture M-5, is very well suitable for the ULH-mode. In particular the response times of this mixture are excellent and it has a relatively broad temperature range for the liquid crystalline phase.

It has a clearing point of 85° C. and a a transition from the second nematic phase to the nematic phase [T(N2,N)] at 25° C. It has a cholesteric pitch of 300 nm at 35° C. The e/K of this mixture is 3.75 $Cm^{-1}N^{-1}$ at a temperature of 35° C.

With an appropriate adjustment of the concentration of the chiral dopant, e.g. to achieve a cholesteric pitch of 200 nm or less, the mixtures of the examples of this application are suitable for use in the USH (uniformly standing helix) mode, and not only in the ULH (uniformly lying helix) mode.

The invention claimed is:

1. A bimesogenic compound of formula I

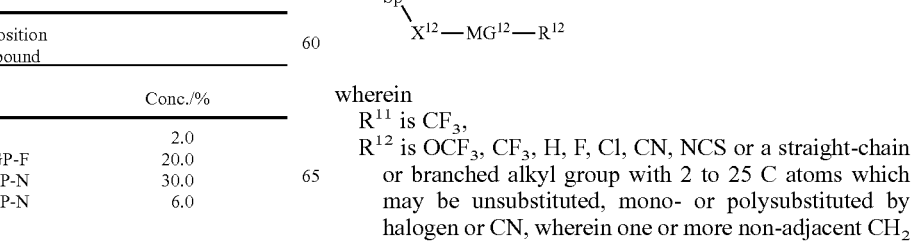

wherein
$R^{11}$ is $CF_3$,
$R^{12}$ is $OCF_3$, $CF_3$, H, F, Cl, CN, NCS or a straight-chain or branched alkyl group with 2 to 25 C atoms which may be unsubstituted, mono- or polysubstituted by halogen or CN, wherein one or more non-adjacent $CH_2$ groups are each optionally replaced, in each occurrence independently from one another, by —O—, —S—, —NH—, —N(CH$_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another, MG$^{11}$ and MG$^{12}$ are each independently a mesogenic group and at least one of MG$^{11}$ and MG$^{12}$ comprises one, two or more 6-atomic rings, and Sp$^1$ is a spacer group comprising 1, 3 or 5 to 40 C atoms, wherein one or more non-adjacent and non-terminal CH$_2$ groups are each optionally replaced by —O—, —S—, —NH—, —N(CH$_3$)—, —CO—, —O—CO—, —S—CO—, —O—COO—, —CO—S—, —CO—O—, —CH(halogen)-, —CH(CN)—, —CH=CH— or —C≡C—, however in such a way that no two O-atoms are adjacent to one another, no two —CH=CH— groups are adjacent to each other, and no two groups selected from —O—CO—, —S—CO—, —O—COO—, —CO—S—, —CO—O— and —CH=CH— are adjacent to each other, X$^{11}$ and X$^{12}$ are independently from one another a linking group selected from —CO—O—, —O—CO—, —CH=CH—, —C≡C—, and —S—, under the condition that in —X$^{11}$-Sp$^1$-X$^{12}$— no two O atoms are adjacent to one another, no two —CH=CH— groups are adjacent to each other, and no two groups selected from —O—CO—, —S—CO—, —O—COO—, —CO—S—, —CO—O— and —CH=CH— are adjacent to each other.

2. A bimesogenic compound according to claim 1, wherein MG$^{11}$ and MG$^{12}$ are independently of each other selected from partial formula II $$-A^{11}-(Z^{11}-A^{12})_k- \qquad II$$

wherein

Z$^{11}$ are, independently of each other in each occurrence, a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—, optionally substituted with one or more of F, S and/or Si, A$^{11}$ and A$^{12}$ are each independently in each occurrence 1,4-phenylene, wherein in addition one or more CH groups are each optionally replaced by N, trans-1,4-cyclo-hexylene in which, in addition, one or two non-adjacent CH$_2$ groups are each optionally replaced by O or S, 1,4-cyclohexenylene, 1,4-bicyclo-(2,2,2)-octylene, piperidine-1,4-diyl, naphthalene-2,6-diyl, deca-hydro-naphthalene-2,6-diyl, 1,2,3,4-tetrahydro-naphthalene-2,6-diyl, cyclobutane-1,3-diyl, spiro[3.3]heptane-2,6-diyl or dispiro[3.1.3.1] decane-2,8-diyl, it being possible for all these groups to be unsubstituted, mono-, di-, tri- or tetrasubstituted with F, Cl, CN or alkyl, alkoxy, alkylcarbonyl or alkoxycarbonyl groups with 1 to 7 C atoms, wherein one or more H atoms are each optionally replaced by F or Cl, and k is 0, 1, 2, 3 or 4.

3. A bimesogenic compound according to claim 2, wherein MG$^{11}$ and MG$^{12}$ are independently of one another selected from the group of formulae II-1 to II-26

| | |
|---|---|
| -Phe-Z-Phe- | II-1 |
| -Phe-Z-Cyc- | II-2 |
| -Cyc-Z-Cyc- | II-3 |
| -Phe-Z-PheL- | II-4 |
| -PheL-Z-Phe- | II-5 |
| -PheL-Z-Cyc- | II-6 |
| -PheL-Z-PheL- | II-7 |
| -Phe-Z-Phe-Z-Phe- | II-8 |
| -Phe-Z-Phe-Z-Cyc- | II-9 |
| -Phe-Z-Cyc-Z-Phe- | II-10 |
| -Cyc-Z-Phe-Z-Cyc- | II-11 |
| -Phe-Z-Cyc-Z-Cyc- | II-12 |
| -Cyc-Z-Cyc-Z-Cyc- | II-13 |
| -Phe-Z-Phe-Z-PheL- | II-14 |
| -Phe-Z-PheL-Z-Phe- | II-15 |
| -PheL-Z-Phe-Z-Phe- | II-16 |
| -PheL-Z-Phe-Z-PheL- | II-17 |
| -PheL-Z-PheL-Z-Phe- | II-18 |
| -PheL-Z-PheL-Z-PheL- | II-19 |
| -Phe-Z-PheL-Z-Cyc- | II-29 |
| -Phe-Z-Cyc-Z-PheL- | II-21 |
| -Cyc-Z-Phe-Z-PheL- | II-22 |
| -PheL-Z-Cyc-Z-PheL- | II-23 |
| -PheL-Z-PheL-Z-Cyc- | II-24 |
| -PheL-Z-Cyc-Z-Cyc- | II-25 |
| -Cyc-Z-PheL-Z-Cyc- | II-26 | wherein

Cyc is 1,4-cyclohexlene, preferably trans-1,4-cyclohexlene,

Phe is 1,4-phenylene,

PheL is 1,4-phenylene, which is substituted by one, two or three fluorine atoms, by one or two Cl atoms or by one Cl atom and one F atom, and Z is a single bond, —COO—, —OCO—, —O—CO—O—, —OCH$_2$—, —CH$_2$O—, —OCF$_2$—, —CF$_2$O—, —CH$_2$CH$_2$—, —(CH$_2$)$_4$—, —CF$_2$CF$_2$—, —CH=CH—, —CF=CF—, —CH=CH—COO—, —OCO—CH=CH— or —C≡C—, optionally substituted with one or more of F, S and/or Si.

4. A bimesogenic compound according claim 1, wherein R$^{12}$ is OCF$_3$, CF$_3$, F, Cl or CN.

5. A bimesogenic compound according to claim 1, wherein Sp$^1$ is —(CH$_2$)$_o$— and o is 1, 3 or an integer from 5 to 15.

6. A liquid-crystalline medium comprising one or more bimesogenic compounds according to claim 1.

7. The liquid-crystalline medium according to claim 6, wherein said medium further comprises one or more compounds selected from formulae III $$R^{31}\text{-}MG^{31}\text{-}X^{31}\text{-}Sp^3\text{-}X^{32}\text{-}MG^{32}\text{-}R^{32}$$  III wherein
- $R^{31}$ and $R^{32}$ are each independently H, F, Cl, CN, NCS or a straight-chain or branched alkyl group with 1 to 25 C atoms which may be unsubstituted, mono- or polysubstituted by halogen or CN, wherein one or more non-adjacent $CH_2$ groups are each optionally replaced, in each case independently from one another, by —O—, —S—, —NH—, —N($CH_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another,
- $MG^{31}$ and $MG^{32}$ are each independently a mesogenic group,
- $Sp^3$ is a spacer group comprising 5 to 40 C atoms, wherein one or more non-adjacent $CH_2$ groups are each optionally replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—, and
- $X^{31}$ and $X^{32}$ are each independently —O—, —S—, —CO—, —COO—, —OCO—, —O—CO—O—, —CO—NH—, —NH—CO—, —$CH_2CH_2$—, —$OCH_2$—, —$CH_2O$—, —$SCH_2$—, —$CH_2S$—, —CH=CH—, —CH=CH—COO—, —OCO—CH=CH—, —C≡C— or a single bond, and with the condition that compounds of formula I are excluded.

8. A liquid crystal device comprising a liquid crystalline medium comprising two or more components, one or more of which is a bimesogenic compound according to claim 1.

9. The liquid crystal device according to claim 8, wherein said device is a flexoelectric device.

10. A bimesogenic compound according claim 1, wherein —$X^{11}$-$Sp^1$-$X^{12}$— is —O—CO-$Sp^1$-O—CO— or —C≡C-$Sp^1$-C≡C—,
- $Sp^1$ is —$(CH_2)_n$—, and
- n is 1, 3 or an integer from 5 to 15,
  wherein one or more H atoms in —$(CH_2)_n$— are each optionally be replaced by F or $CH_3$.

11. A bimesogenic compound according to claim 3, wherein $MG^{11}$ and $MG^{12}$ are independently of one another selected from formulae II-1, II-4, II-5, II-7, II-8, II-14, II-15, II-16, II-17, II-18 and II-19.

12. A bimesogenic compound according to claim 3, wherein one of Z is —COO—, —OCO—, —$CH_2$—O—, —O—$CH_2$—, —$CF_2$—O— or —O—$CF_2$—, and the others of Z, if present, are each a single bond.

13. A bimesogenic compound according to claim 2, wherein $MG^{11}$ and $MG^{12}$ are independently of one another selected from the following formulae and their mirror images:

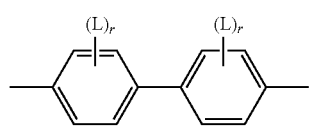

IIa

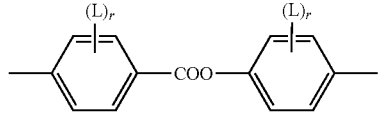

IIb

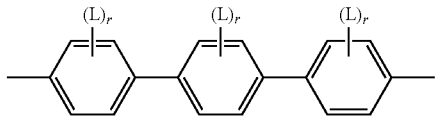

IIc

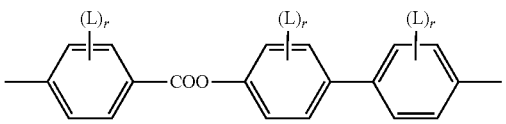

IId

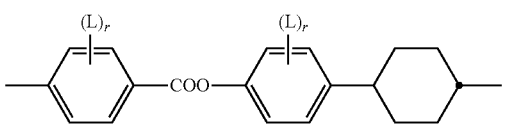

IIe

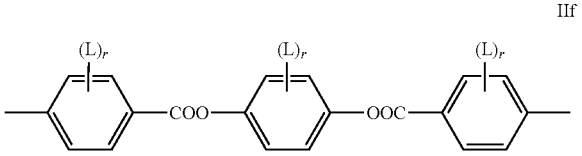

IIf

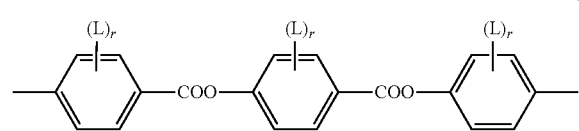

IIg

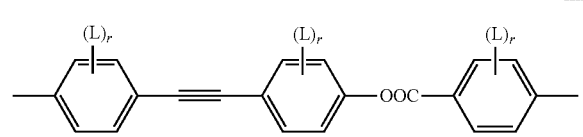

IIh

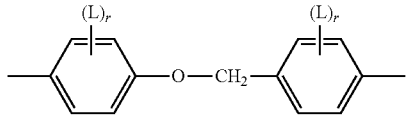

IIi

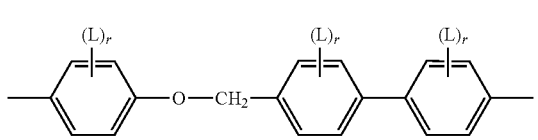

IIj

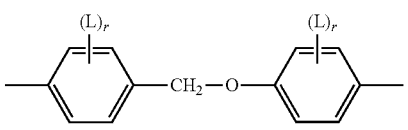

IIk

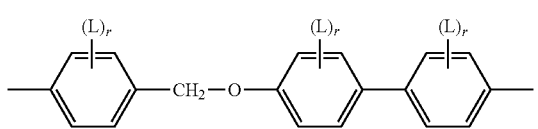

III

-continued

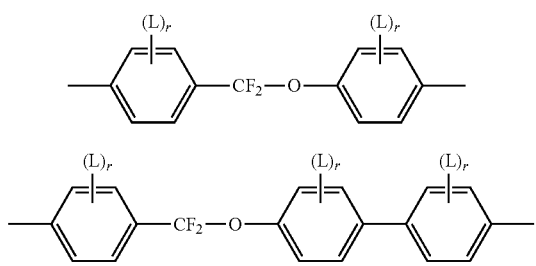

wherein
L is in each occurrence independently of each other F or Cl, and
r is in each occurrence independently of each other 0, 1, 2 or 3.

14. A bimesogenic compound according claim 1, wherein $R^{12}$ is H, F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, or $OC_2F_5$.

15. A bimesogenic compound according claim 1, wherein $Sp^1$ is a linear or branched alkylene group having 1, 3 or 5 to 40 C atoms, in which, in addition, one or more non-adjacent and non-terminal $CH_2$ groups are each optionally replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

16. A bimesogenic compound according claim 1, wherein said compound is selected from the following formulae:

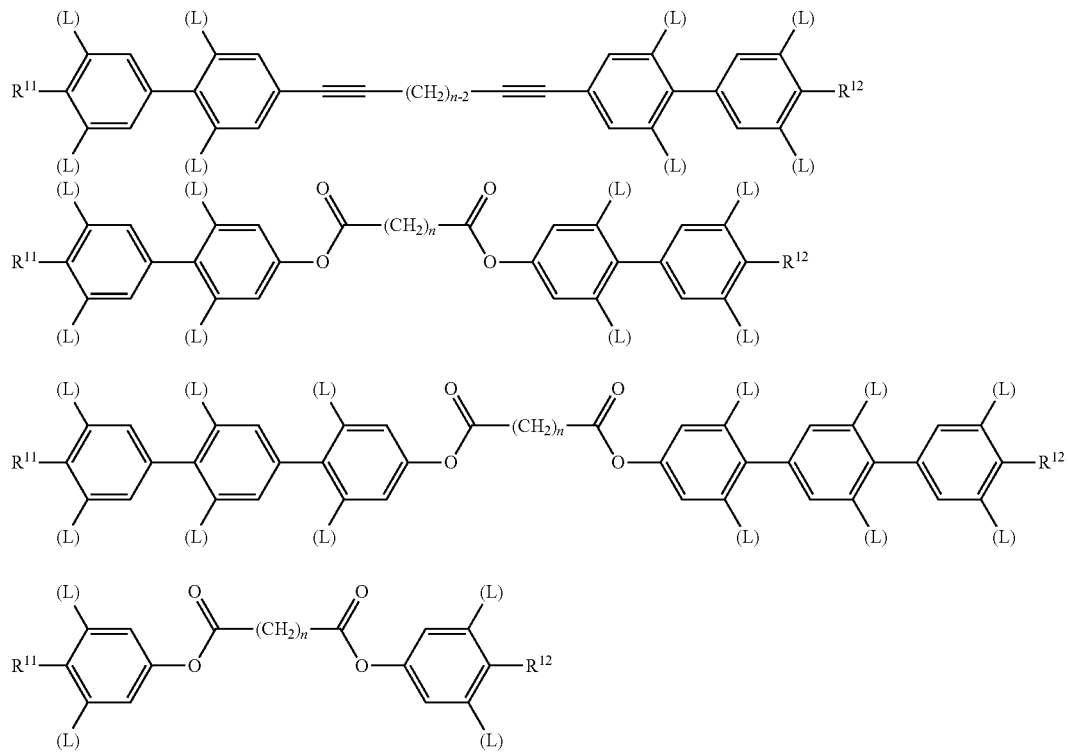

wherein n is 1, 3 or an integer from 5 to 15, and $R^{11}$ and $R^{12}$ are as defined in claim 1.

17. A bimesogenic compound according claim 1, wherein $R^{12}$ is $OCF_3$, F or CN.

18. A bimesogenic compound of formula I

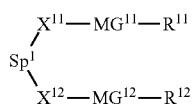

wherein
$R^{11}$ is $OCF_3$ or $CF_3$,
$R^{12}$ is $OCF_3$, $CF_3$, H, F, Cl, CN, NCS or a straight-chain or branched alkyl group with 2 to 25 C atoms which may be unsubstituted, mono- or polysubstituted by halogen or CN, wherein one or more non-adjacent $CH_2$ groups are each optionally replaced, in each occurrence independently from one another, by —O—, —S—, —NH—, —N($CH_3$)—, —CO—, —COO—, —OCO—, —O—CO—O—, —S—CO—, —CO—S—, —CH=CH—, —CH=CF—, —CF=CF— or —C≡C— in such a manner that oxygen atoms are not linked directly to one another,
$MG^{11}$ and $MG^{12}$ are each independently a mesogenic group and
at least one of
$MG^{11}$ and $MG^{12}$ comprises one, two or more 6-atomic rings, and
$Sp^1$ is a spacer group comprising 1, 3 or 5 to 40 C atoms, wherein one or more non-adjacent and non-terminal $CH_2$ groups are each optionally replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—, however in such a way that no two O-atoms are adjacent to one another, no two —CH=CH— groups are adjacent to each other, and no two groups selected from —O—CO—, —S—CO—, —O—COO—, —CO—S—, —CO—O— and —CH=CH— are adjacent to each other, $X^{11}$ and $X^{12}$ are independently from one another a linking group selected from —CO—O—, —O—CO—, —CH=CH—, —C≡C—, and —S—, under the condition that in —$X^{11}$—$Sp^1$—$X^{12}$ no two O atoms are adjacent to one another, no two —CH=CH— groups are adjacent to each other, and no two groups selected from —O—CO—, —S—CO—, —O—COO—, —CO—S—, —CO—O— and —CH=CH— are adjacent to each other.

19. A bimesogenic compound according claim 18, wherein —$X^{11}$—$Sp^1$-$X^{12}$— is —O—CO-$Sp^1$-O—CO— Previously Presented or —C≡C-$Sp^1$-C≡C—, $Sp^1$ is —$(CH_2)_n$—, and n is 1, 3 or an integer from 5 to 15, wherein one or more H atoms in —$(CH_2)_n$— are each optionally be replaced by F or $CH_3$.

20. A bimesogenic compound according claim 18, wherein said compound is selected from the following formulae:

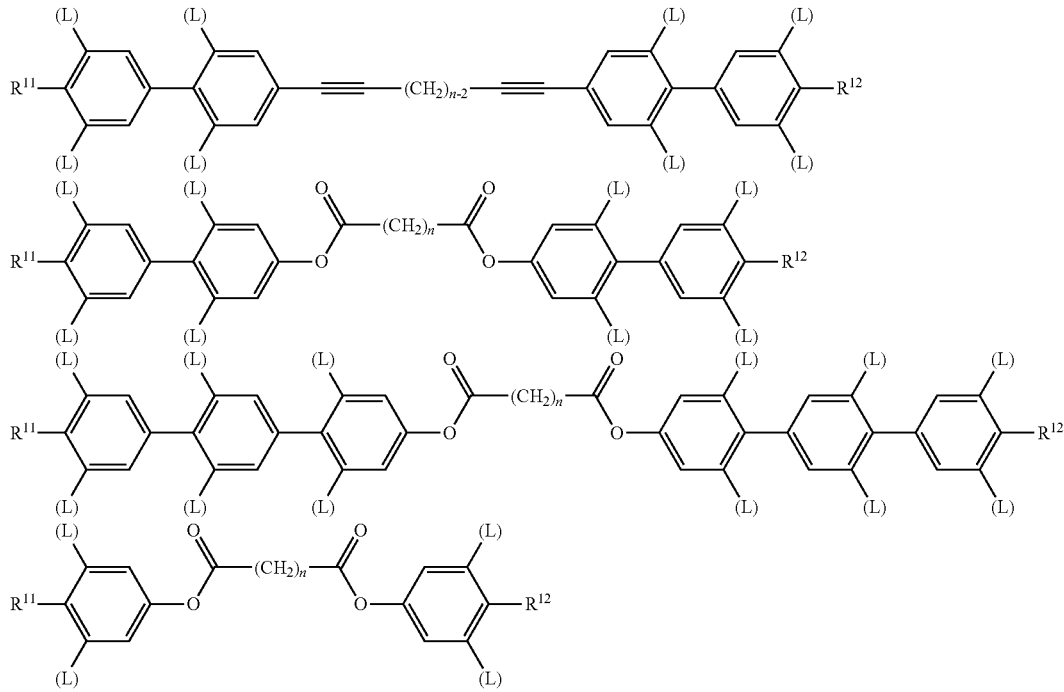

wherein n is 1, 3 or an integer from 5 to 15, and $R^{11}$ and $R^{12}$ are as defined in claim 18.

21. A bimesogenic compound according claim 18, wherein $R^{11}$ is $OCF_3$ and $R^{12}$ is $OCF_3$, F or CN.

22. A bimesogenic compound according to claim 18, wherein said compound is selected from the following compounds:

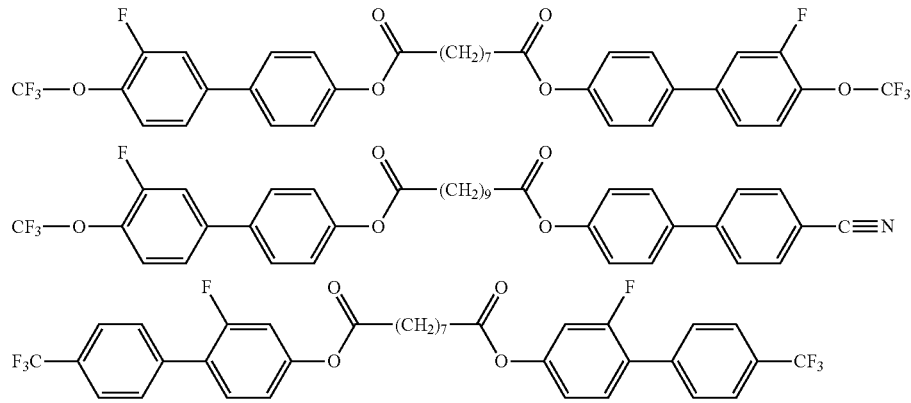

-continued
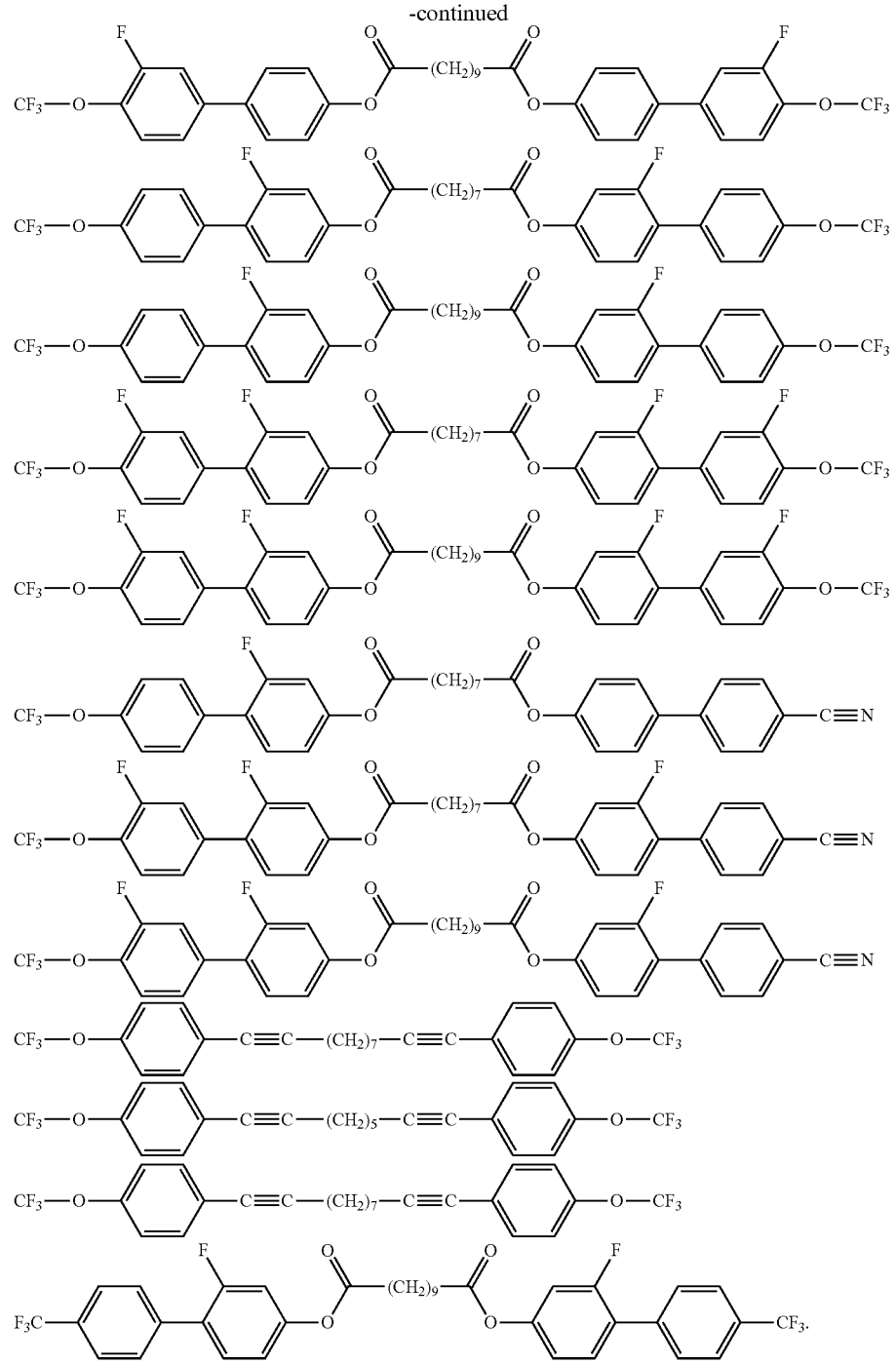
* * * * *